(12) United States Patent
Floeder et al.

(10) Patent No.: US 8,935,104 B2
(45) Date of Patent: *Jan. 13, 2015

(54) APPLICATION-SPECIFIC REPEAT DEFECT DETECTION IN WEB MANUFACTURING PROCESSES

(75) Inventors: Steven P. Floeder, Shoreview, MN (US); James A. Masterman, Lake Elmo, MN (US); Steven R. Dreger, Maplewood, MN (US); Carl J. Skeps, Lakeville, MN (US); Steven R. Wageman, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 450 days.

This patent is subject to a terminal disclaimer.

(21) Appl. No.: 13/040,313

(22) Filed: Mar. 4, 2011

(65) Prior Publication Data

US 2011/0224918 A1     Sep. 15, 2011

Related U.S. Application Data

(60) Provisional application No. 61/312,598, filed on Mar. 10, 2010.

(51) Int. Cl.
*D06H 3/08* (2006.01)
*G01N 21/89* (2006.01)
*G06K 9/82* (2006.01)

(52) U.S. Cl.
CPC ........ *G01N 21/89* (2013.01); *G01N 2021/8917* (2013.01); *G01N 2021/8918* (2013.01); *G01N 21/8915* (2013.01); *D06H 3/08* (2013.01)
USPC ................................ 702/35; 702/81; 702/167

(58) Field of Classification Search
USPC ................. 702/35, 167, 58, 81, 82, 183, 185; 382/111, 144, 194
See application file for complete search history.

(56) References Cited

U.S. PATENT DOCUMENTS

| | | | |
|---|---|---|---|
| 4,134,684 A | 1/1979 | Jette | |
| 4,982,600 A | 1/1991 | Kiso et al. | |
| 6,665,432 B1 * | 12/2003 | Evans et al. | 382/141 |
| 6,665,498 B1 | 12/2003 | Jiang et al. | |
| 6,950,547 B2 * | 9/2005 | Floeder et al. | 382/143 |
| 7,027,934 B2 * | 4/2006 | Skeps et al. | 702/35 |

(Continued)

FOREIGN PATENT DOCUMENTS

| | | |
|---|---|---|
| CN | 101173905 | 5/2008 |
| EP | 1 914 540 A2 | 4/2008 |

(Continued)

*Primary Examiner* — Michael Nghiem
*Assistant Examiner* — Ivan Rabovianski
(74) *Attorney, Agent, or Firm* — Steven A. Bern

(57) ABSTRACT

Techniques are described for inspecting a web and controlling subsequent conversion of the web into one or more products. A system, for example, comprises an imaging device, an analysis computer and a conversion control system. The imaging device images the web to provide digital information. The analysis computer processes the digital information to identify regions on the web containing anomalies. The conversion control system subsequently analyzes the digital information to determine which anomalies represent actual defects for a plurality of different products. The web inspection system may preferentially apply different application-specific defect detection recipes depending on whether a given anomaly is a repeating or random anomaly.

28 Claims, 30 Drawing Sheets

(56) References Cited

U.S. PATENT DOCUMENTS

| | | |
|---|---|---|
| 7,187,995 B2 | 3/2007 | Floeder et al. |
| 7,623,699 B2 * | 11/2009 | Floeder et al. ............ 382/149 |
| 7,797,133 B2 | 9/2010 | Floeder et al. |
| 8,023,720 B2 | 9/2011 | Reunanen |
| 8,175,739 B2 * | 5/2012 | Floeder et al. ............ 700/122 |
| 2005/0075801 A1 * | 4/2005 | Skeps et al. ............ 702/35 |
| 2009/0028416 A1 * | 1/2009 | Floeder et al. ............ 382/141 |
| 2009/0028417 A1 * | 1/2009 | Floeder et al. ............ 382/141 |
| 2009/0030544 A1 | 1/2009 | Floeder et al. |
| 2010/0063750 A1 | 3/2010 | Floeder et al. |

FOREIGN PATENT DOCUMENTS

| | | |
|---|---|---|
| WO | WO 2009/014818 A1 | 1/2009 |
| WO | WO 2010/030483 A1 | 3/2010 |

* cited by examiner

APPLICATION-SPECIFIC REPEAT DEFECT DETECTION IN WEB MANUFACTURING PROCESSES

CROSS REFERENCE TO RELATED APPLICATION

This application claims the benefit of U.S. Provisional Patent Application No. 61/312,598, filed Mar. 10, 2010, the disclosure of which is incorporated by reference herein in its entirety.

This application incorporates by reference patent application "Multi-Roller Registered Repeat Defect Detection of a Web Process Line" to Floeder et al., Ser. No. 12/207,582, filed Sep. 10, 2008, Granted as U.S. Pat. No. 7,797,133 on Sep. 14, 2010, assigned to the assignee of the present application, the entire contents of which are hereby incorporated by reference.

TECHNICAL FIELD

The invention relates to automated inspection systems, and more particularly, to systems for inspecting of moving webs.

BACKGROUND

Inspection systems for the analysis of moving web materials have proven critical to modern manufacturing operations. Industries as varied as metal fabrication, paper, nonwoven materials, and films rely on these inspection systems for both product certification and online process monitoring.

Products created on web process lines are subject to anomalies or defects from many sources. One particular concern is web line-induced anomalies, such as those created by continuously rotating equipment contacting the web in a regular, repeating pattern. Such equipment can generally be described as a "roll." Typical rolls utilized within a web manufacturing line include but are not limited to casting wheels, pull rolls, nip rolls, microreplicating rolls, web cleaning components, and idlers.

For example, the surface of a roll may be damaged (e.g., scratched) or a may have a contaminant (e.g., dirt or other particle) that induces an anomaly or defect in the moving web carried by the roll. Moreover, the roll can cause so-called "repeating anomalies" in that a new anomaly may be imparted into the moving web with each rotation of the roll. On the resulting web product, these anomalies repeat at a distance equal to the roll's circumference in the same cross-direction or "cross-web" position. Web process lines may have hundreds of rolls, many of which may have similar diameters. Identifying the specific offending roll that induced a repeating anomaly or defect within the web can be difficult with conventional inspection systems.

For example, commercially available web inspection systems provide identification of repeating defects, including cross-web position and down-web repeat distance. However, these systems typically require a priori knowledge of existing roll diameters on a given process line in order to extract repeating defect information from the entire data stream. Moreover, in many cases there may be many idlers or other rolls within a given web process line with circumferences that are near a given repeat distance of a repeating anomaly, making defect-causing roll identification difficult. As one example, a length orienter on a film making line may have numerous rolls (e.g., twelve or more), all of nominally the same eight-inch diameter. It is often difficult to determine the unique defect-causing roll using traditional methods due in part to slight variations in diameter of each of these rolls. In addition, conventional systems are often unable to account for any spatial distortion (e.g., stretching) of the web between the defect-causing roll and the web inspection system. Further, undocumented roll changes to a web process line can also occur. For example, a six-inch diameter roll may be replaced by a five-inch diameter roll and may begin introducing repeat defects. Process operators using conventional web inspection systems might not check the changed roll as the source of anomalies or defects due to the change not being documented and the assumed diameter of the roll being incorrect.

SUMMARY

In general, this application describes techniques for the automated inspection of moving webs. An inspection system, for example, acquires anomaly information for a web using an optical acquisition device, and performs preliminary examination with a first, typically less sophisticated algorithm. Image information about the regions of the web containing anomalies is stored for subsequent processing, accepting the likelihood that although some of the anomalies may ultimately be identified as defects, many could be "false positives," i.e., anomalies that are not defects. Moreover, some anomaly areas in the web may be ultimately classified as defective if the web were converted to a particular product application, but not defective if the web were to be used in another.

The original anomaly information can be reconsidered and fully analyzed at a convenient time, even after the inspected web has been wound onto a roll and is unavailable. As a result, the speed of the moving web during the inspection can be much greater than is possible when the entire surface of the web is subjected to a sophisticated analysis.

For example, conversion decisions can be made offline, and can be based on many factors. A conversion control system subsequently reconsiders the original image information, and subjects the image information to at least one of a variety of more sophisticated image processing and defect extraction algorithms (collectively referred to herein as "application-specific defect detection recipes" or simply "recipes") to effectively separate actual defects from anomalies based on potential uses of the web. The conversion control system utilizes the defect information to determine and control the manner in which a web is ultimately converted to the products based on one or more product selection parameters.

Specifically, the conversion control system applies the image processing and defect extraction algorithms to generate defect information for a number of potential web-based products, i.e., products into which the web could be converted. The conversion control system then identifies which product best achieves the selected parameters, such as a maximum utilization of the web. Other examples of product selection parameters that may be used to influence the conversion selection process include unit product produced, estimated revenue or profit from the produced product, process time required to convert the web, current machine capacity for each process line, current demand for the different products or other parameters.

In addition, the techniques described herein enable the automated inspection system to distinguish between anomalies that occur repeatedly and random anomalies for which a source may not be determinable. Certain elements of a web manufacturing line may introduce repeated anomalies or defects into the web. For example, idler rollers, generally referred to herein as "rolls," that support the web as it traverses the system may introduce repeated anomalies into the web at regular intervals. In accordance with the techniques described herein, the automated inspection system may identify these repeated anomalies within the web and may even determine the source of the anomalies. This may permit operators of the manufacturing line to locate the anomaly-causing element to repair or replace the offending element.

In some embodiments, the web inspection system may preferentially apply different application-specific defect detection recipes depending on whether a given anomaly is a repeating or random anomaly. For example, the techniques recognize that it may be advantageous to apply different defect sensitivity to repeating anomalies as opposed to non-repeating or random anomalies in the same web. In other words, when determining which anomalies in a web qualify as defects for a given potential end use, the web inspection system may apply a first set of one or more application-specific defect detection recipes to the repeating anomalies and a second set of application-specific defect detection recipes to random anomalies. The defect detection recipes of the sets may differ in terms of algorithm and anomaly characteristics considered or may consider the same characteristics and differ only in terms of sensitivity. For example, in some situations, a more stringent recipe for classifying repeat anomalies as defects may be preferred as a customer may be more sensitive to repeat defects in the final product. In this case, application of a more stringent application-specific defect detection recipe applied only to the repeating anomalies may result in an improved level of customer satisfaction. Further, a more stringent recipe for classifying repeat defects may provide for increased process control by allowing offending manufacturing elements, e.g., rollers to be more readily identified and repaired.

Moreover, in some cases the sensitivity of the different sets of application defect detection recipes may be tuned to achieve substantially the same level of customer satisfaction yet realize an increase in conversion yield for the web. For example, a less stringent application-specific defect detection recipe applied only to random (non-repeating) anomalies without increasing, or only moderately increasing, the sensitivity for repeating anomalies may ultimately achieve an increased conversion yield yet maintain substantially the same level of customer satisfaction as would be otherwise achieved without differentiating between repeating and non-repeating anomalies. Further, the sensitivity of the different sets of defect detection recipes may be tuned on a per-product basis in view of perceived customer satisfaction or tolerance of repeat anomalies.

Further, the web inspection system may identify positions of anomalies or defects within the web and then correlate those positions with roll synchronization signals that were received during the manufacturing of the web. For example, each roll of interest for a web manufacturing process is equipped with a synchronization mark. During manufacturing of the web, the web inspection system receives a roll synchronization signal from each of the rolls indicating that the respective roll has completed a full rotation. The web inspection system records the position of each occurrence of these synchronization marks with respect to its downweb positional coordinate system. The web inspection system then correlates positional data of the roll synchronization signals with positional data for the anomalies or defects.

In one embodiment, the invention is directed to a method comprising receiving roll synchronization signals from a plurality of sensors of a web manufacturing system, wherein each of the sensors corresponds to a different roller of the web manufacturing system, and wherein each of the roll synchronization signals indicates that the corresponding roller has completed a full rotation during manufacturing of a web of material. The method further comprises receiving anomaly data from a web inspection system that identifies positions of anomalies on the web. The method further comprises identifying a set of two or more of the anomalies as repeated, identifying which of the rollers caused the repeated anomalies by correlating the positions of the repeated anomalies with the roll synchronization signals, and outputting an identification of the offending one of the rollers.

In another embodiment, the invention is directed to a system comprising a plurality of rollers in contact with a web of material, wherein two or more of the rollers each include a synchronization mark to indicate when the corresponding roller has completed a full rotation. The system includes a plurality of synchronization mark readers that read the synchronization marks of the plurality of rollers and output roll synchronization signals. Each of the roll synchronization signals indicates that the corresponding roller has completed a full rotation during manufacturing of the web. The system also includes an encoder on at least one of the rollers that outputs a position signal indicative of a down-web distance of the web, and an inspection system that inspects the web and outputs anomaly data identifying positions of anomalies on the web. A synchronization unit receives the position signal from the encoder and the plurality of roll synchronization signals from the synchronization mark readers, and converts the occurrence of each of the roll synchronization signals into down-web positions within a coordinate system associated with web process line. An analysis computer processes the anomaly data to identify a set of two or more of the anomalies as repeated anomalies. The analysis computer outputs an indication of which of the rollers caused the repeated anomalies by correlating the positions of the repeated anomalies with the down-web positions of the roll synchronization signals.

In another embodiment, the invention is directed to a computer-readable storage medium containing software instructions. The instructions cause a programmable processor of a computer to execute the software instructions and perform at least some of the functions set forth herein.

The techniques described herein may provide several advantages. For example, the techniques may achieve significant accuracy improvement over conventional systems. For example, the techniques can be used to easily differentiate roll sizes that differ less than 25 μm. This allows an offending roll to be identified from a group of rolls of similar diameters, thereby enabling simpler and more robust manufacturing process maintenance. Further, the techniques allow repeated anomalies or defects on a web to be detected even amidst a large number of random defects. In addition, the techniques allow the system to measure the exact crossweb and circumferential position of the defect producing area of a roll, and even differentiate between multiple repeating defects at the same crossweb position.

The details of one or more embodiments of the invention are set forth in the accompanying drawings and the description below. Other features, objects, and advantages of the invention will be apparent from the description and drawings, and from the claims.

DEFINITIONS

For purposes of the present invention, the following terms used in this application are defined as follows:

"web" means a sheet of material having a fixed dimension in one direction and either a predetermined or indeterminate length in the orthogonal direction;

"sequential" means that an image is formed by a succession of single lines, or areas of the web that optically map to a single row of sensor elements (pixels);

"pixel" means a picture element represented by one or more digital values;

"blob" means a connected set of pixels in a binary image;

"defect" means an undesirable occurrence in a particular product;

"anomaly" or "anomalies" mean a deviation in the web that may or may not be a defect in a given product, depending on its characteristics and severity of the anomaly.

"gray scale" means pixels having a multitude of possible values, e.g. 256 digital values;

"binarization" is an operation for transforming a pixel into a binary value;

"filter" is a mathematical transformation of an input image to a desired output image, filters are typically used to enhance contrast of a desired property within an image;

"application-specific" means defining requirements, e.g., grade levels, based on the intended use for the web;

"yield" represents a utilization of a web expressed in percentage of material, unit number of products or some other manner;

"recipes" are application-specific algorithms that can be applied to the anomaly information to determine any actual defects based on a variety of factors;

"products" are the individual sheets (also referred to as component) produced from a web, e.g., a rectangular sheet of film for a cell phone display or a television screen; and "conversion" the process of physically cutting a web into products.

DETAILED DESCRIPTION

Figure 1:
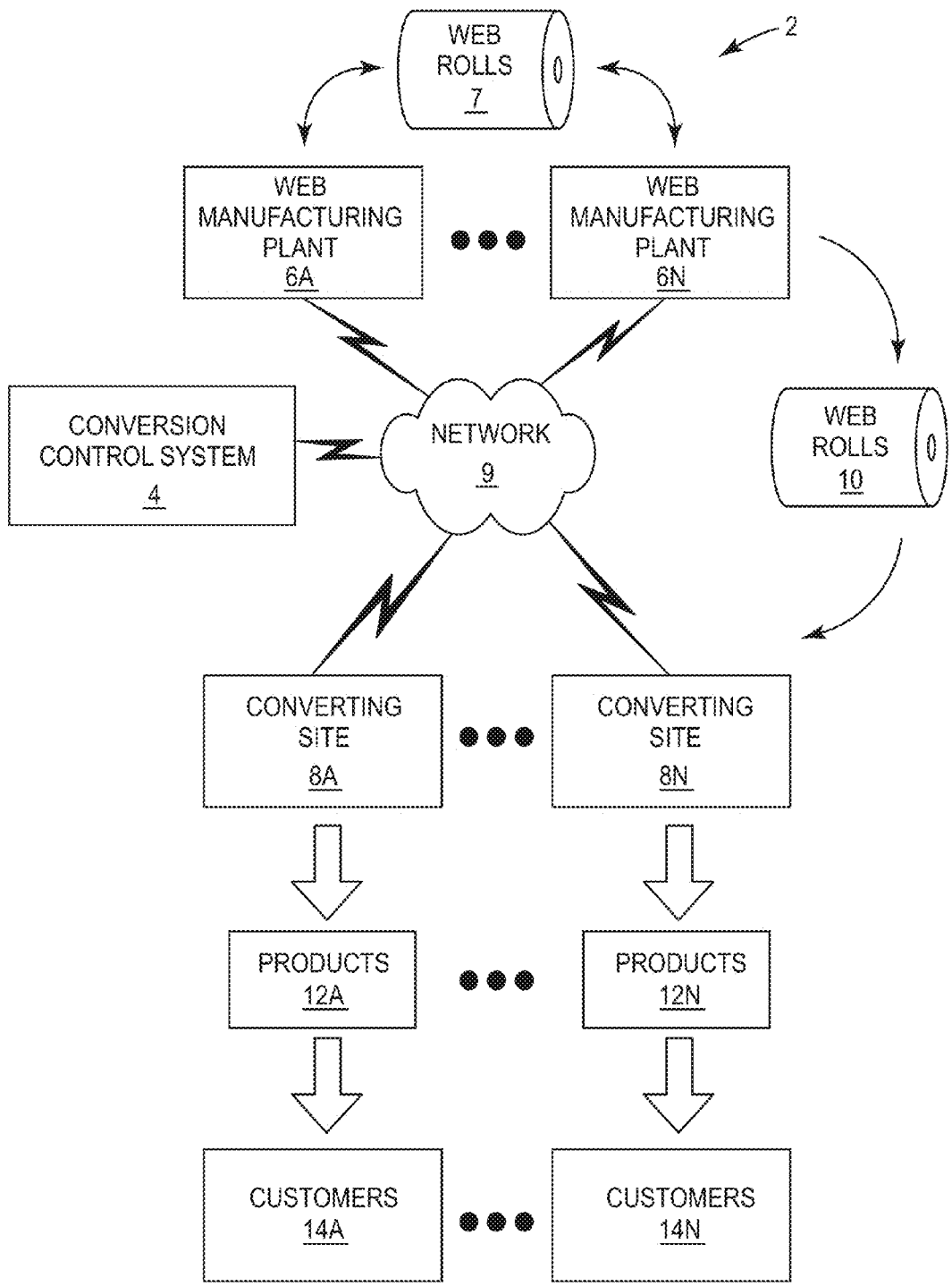
FIG. 1 is a block diagram illustrating a global network environment in which a conversion control system controls conversion of web material.

FIG. 1 is a block diagram illustrating a global network environment 2 in which conversion control system 4 controls conversion of web material. More specifically, web manufacturing plants 6A-6M (web manufacturing plants 6) represent manufacturing sites that produce and ship web material in the form of web rolls 7 between each other and ship finished web rolls 10 to converting sites 8A-8N (converting sites 8). Web manufacturing plants 6 may be geographically distributed, and each of the web manufacturing plants may include one or more manufacturing process lines. Converting sites 8 may be part of the same entity as web manufacturing plants 6. However, in some embodiments, converting sites 8 are consumers of finished web rolls 10. Converting sites 8 may purchase finished web rolls 10 from web manufacturing plants 6 and convert finished web rolls 10 into individual sheets for incorporation into products 12 based on grade levels. That is, the selection process of which sheets should be incorporated into which of products 12 may be based on which of the grade levels each sheet satisfies. In accordance with the techniques described herein, converting sites 8 may also receive data regarding anomalies, i.e. potential defects, in the finished web rolls 10. Ultimately, converting sites 8 may convert finished web rolls 10 into individual sheets which may be incorporated into products 12 for sale to customers 14A-14N (customers 14).

In general, web rolls 7, 10 may contain manufactured web material that may be any sheet-like material having a fixed dimension in one direction and either a predetermined or indeterminate length in the orthogonal direction. Examples of web materials include, but are not limited to, metals, paper, wovens, non-wovens, glass, polymeric films, flexible circuits or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

In order to produce a finished web roll 10 that is ready for conversion into individual sheets for incorporation into products 12, unfinished web rolls 7 may need to undergo processing from multiple process lines either within one web manufacturing plant, for instance, web manufacturing plant 6A, or within multiple manufacturing plants. For each process, a web roll is typically used as a source roll from which the web is fed into the manufacturing process. After each process, the web is typically collected again into a web roll 7 and moved to a different product line or shipped to a different manufacturing plant, where it is then unrolled, processed, and again collected into a roll. This process is repeated until ultimately a finished web roll 10 is produced.

An anomaly introduced into a web roll 7 by one plant, for example, web manufacturing plant 6A, may be detectable once plant 6A has finished its processes on web roll 7, but the anomaly may later become undetectable after another web manufacturing plant, such as web manufacturing plant 6B, has performed its manufacturing processes on web roll 7.

For many applications, the web materials for each of web rolls 7 may have numerous coatings applied at one or more production lines of one or more web manufacturing plants 6. The coating is generally applied to an exposed surface of either a base web material, in the case of the first manufacturing process, or a previously applied coating in the case of a subsequent manufacturing process. Examples of coatings include adhesives, hardcoats, low adhesion backside coatings, metalized coatings, neutral density coatings, electrically conductive or nonconductive coatings, or combinations thereof. A given coating may be applied to only a portion of the web material or may fully cover the exposed surface of the web material. Further, the web materials may be patterned or unpatterned.

Figure 2:
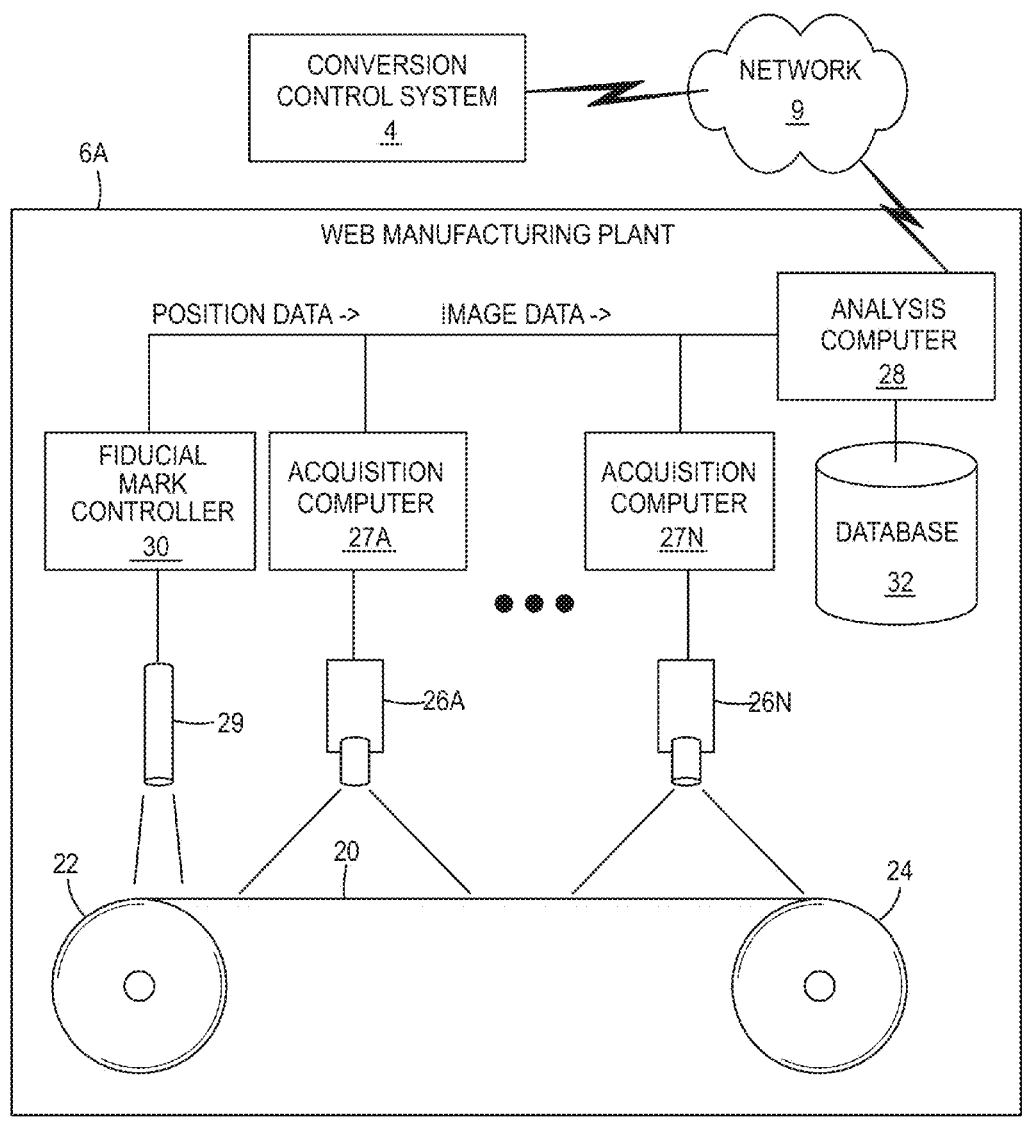
FIG. 2 is a block diagram illustrating an exemplary embodiment of an inspection system in an exemplary web manufacturing plant.

During each manufacturing process for a given one of web rolls 7, one or more inspection systems acquire anomaly information for the web. For example, as illustrated in FIG. 2, an inspection system for a production line may include one or more image acquisition devices positioned in close proximity to the continuously moving web as the web is processed, e.g., as one or more coatings are applied to the web. The image acquisition devices scan sequential portions of the continuously moving web to obtain digital image data. The inspection systems may analyze the image data with one or more algorithms to produce so called "local" anomaly information. The anomaly information may include a plurality of anomaly objects that represent distinct areas of the web and define a plurality of characteristics for the physical deviations of the web at the corresponding area. An anomaly object may define characteristics such as, for example, a deviation in width of the anomalous area of the web or a deviation in length of an anomalous area of the web. Thus the length and width may represent a physical deviation from predefined characteristics that define, for example, various grade levels. In one exemplary embodiment, image data may be acquired and processed to identify anomalies and to form anomaly objects as data structures representing each anomaly. Information regarding the acquisition and registration of anomaly information is detailed in co-pending U.S. patent application "Multi-Unit Process Spatial Synchronization" to Floeder et al., Ser. No. 11/828,369 (now U.S. Pat. No. 8,175,739 B2), filed Jul. 26, 2007, assigned to the assignee of the present application, the entire contents of which are hereby incorporated by reference.

In general, conversion control system 4 applies one or more defect detection algorithms ("recipes") that may be application-specific, i.e., specific to products 12, to select and generate a conversion plan for each web roll 10. A certain anomaly may result in a defect in one product, for instance product 12A, whereas the anomaly may not cause a defect in a different product, for instance, product 12B. In some embodiments, conversion control system 4 may apply different application-specific defect detection recipes to the identified anomalies of the web roll 10 depending on whether a given anomaly is a determined to be a repeating anomaly or a random, i.e., non-repeating, anomaly. Each conversion plan represents defined instructions for processing a corresponding finished web roll 10 for creating products 12, which may ultimately be sold to customers 14. For example, a web roll 10 may be converted into final products, e.g., sheets of a certain size, for application to displays of notebook converters. As another example, the same web roll 10 may instead be converted into final products for application to displays of cell phones. Conversion control system 4 may identify which product best achieves certain parameters, such as a maximum utilization of the web, in view of the different defect detection algorithms that may be applied to the repeating and non-repeating anomalies. Moreover, an operator may adjust certain constraints of the different defect detection algorithms, such as a difference in sensitivity to be applied to repeating and non-repeating anomalies, to view an impact on any of the parameters, such as utilization of the web. Other examples of product selection parameters that may be used to influence the conversion selection process include unit product produced, estimated revenue or profit from the produced product, process time required to convert the web, current machine capacity for each process line, current demand for the different products or other parameters. Further details with respect to the product selection process are described in U.S. Pat. No. 7,187,995 entitled "MAXIMIZATION OF YIELD FOR WEB-BASED ARTICLES," to Floeder et al., issued Mar. 6, 2007, the entire contents of which are incorporated herein by reference.

Certain elements of the process lines within web manufacturing plants 6 may introduce repeated anomalies or defects into the web. For example, "rolls" that engage the web as it traverses the process line may introduce repeated anomalies into the web at regular intervals. Example rolls utilized within a web process line include casting wheels, pull rolls, nip rolls, microreplicating rolls, web cleaning components, and idler rollers. In accordance with the techniques described herein, automated inspection systems, either located within manufacturing plants 6 or remote, identify these repeated anomalies within the web and determine the source roll that induced the repeated anomalies. This permits operators to locate the anomaly-causing element of the system and to repair or replace the offending element.

As described in further detail below, the web inspection system may identify positions of anomalies (or anomalies classified as defects) within the web and correlate those positions with roll synchronization signals that were received during the manufacturing of the web. For example, each roll of interest for a given web manufacturing process of manufacturing plants 6 may be equipped with a synchronization mark. During manufacturing of the web, the web inspection system receives a roll synchronization signal from each of the rolls indicating that the respective roll has completed a full rotation. The web inspection system records the occurrence of these synchronization marks. The web inspection system then converts the occurrence of each of the roll synchronization signals into the spatial domain of the inspection system for correlation with positional data for the anomalies or defects.

The techniques described herein may provide several advantages. For example, the techniques may achieve significant accuracy improvement over conventional systems. For example, the techniques can be used to easily differentiate roll sizes that differ less than 25 μm. This allows an offending roll to be identified from a group of rolls of similar diameters. Further, the techniques allow repeated anomalies or defects on a web to be detected even amidst a large number of random defects. In addition, the techniques allow the system to measure the exact crossweb and circumferential position of the defect producing area of a roll, and even differentiate between multiple repeating defects on the same roll or at the same crossweb position.

Further, in some cases anomalies often appear the same to conventional inspection systems regardless of whether the anomaly occurs on the top side of a web or on the bottom side of a web. However, it is often desirous to know on which side of the web defects occur because, for example, anomalies on the one side of the web, say the bottom, may be healed by coatings on subsequent processes, but anomalies on the top side will still be visible after the final manufacturing operation. Thus, by determining the causal roll for a particular repeating anomaly, the inspection system can determine which side of the web an anomaly is on by storing data specifying the side (i.e., top or bottom) on which each roller is located and correlating each repeated anomaly to an individual roller in an automated manner. Data can be output indicating the side of the roller causing the anomaly by displaying and indication to a user, storing the data in a database or communicating the data to other electronic systems or devices.

The inspection system described herein may be further configured to automatically disregard repeated anomalies on the bottom side of the web without alerting the operator, while immediately alerting for defects on the top side. Alternatively, such anomalies on the bottom of the web may be designated as at a lower alert or warning level. Thus another potential advantage of the techniques described herein may be efficiently detecting and reporting of anomalies of varying degrees of importance.

FIG. 2 is a block diagram illustrating an exemplary embodiment of an inspection system located within a portion of a web process line in exemplary web manufacturing plant 6A of FIG. 1. In the exemplary embodiment, a segment of a web 20 is positioned between two support rolls 22, 24. Image acquisition devices 26A-26N (image acquisition devices 26) are positioned in close proximity to the continuously moving web 20. Image acquisition devices 26 scan sequential portions of the continuously moving web 20 to obtain image data. Acquisition computers 27 collect image data from image acquisition devices 26, and transmit the image data to analysis computer 28 for preliminary analysis.

Image acquisition devices 26 may be conventional imaging devices that are capable of reading a sequential portion of the moving web 20 and providing output in the form of a digital data stream. As shown in FIG. 2, imaging devices 26 may be cameras that directly provide a digital data stream or an analog camera with an additional analog to digital converter. Other sensors, such as, for example, laser scanners, may be utilized as the imaging acquisition device. A sequential portion of the web indicates that the data is acquired by a succession of single lines. Single lines comprise an area of the continuously moving web that maps to a single row of sensor elements or pixels. Examples of devices suitable for acquiring the image include linescan cameras such as Piranha Models from Dalsa (Waterloo, Ontario, Canada), or Model Aviiva SC2 CL from Atmel (San Jose, Calif.). Additional examples include laser scanners from Surface Inspection Systems GmbH (Munich, Germany) in conjunction with an analog to digital converter.

The image may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light, for example, is often suitable for the detection of defects caused by web surface deformations, such as surface scratches.

In some embodiments, fiducial mark controller 30 controls fiducial mark reader 29 to collect roll and position information from web 20. For example, fiducial mark controller 30 may include one or more photo-optic sensors for reading bar codes or other indicia from web 20. In addition, fiducial mark controller 30 may receive position signals from one or more high-precision encoders engaged with web 20 and/or rollers 22, 24. Based on the position signals, fiducial mark controller 30 determines position information for each detected fiducial mark. Fiducial mark controller 30 communicates the roll and position information to analysis computer 28, which may use the position information associated with the acquired image data of the web to determine which anomalies are repeating anomalies and which are random anomalies and apply appropriate recipes based thereon. Analysis computer 28 may further correlate the positions of any repeating anomalies with roll synchronization signals that were received during the manufacturing of the web to identify the offending element(s). Techniques for applying and using fiducial marks to identify specific locations on a web are described in co-pending patent application "Apparatus and Method for the Automated Marking on Webs of Material" to Floeder et al., assigned to the assignee of the present application, Ser. No. 10/826,995 (now U.S. Pat. No. 7,623,699 B2), filed Apr. 19, 2004, the entire contents of which are hereby incorporated by reference. Although discussed with respect to fiducial marks and a fiducial mark controller 30 and reader 29, fiducial marks may not be necessary in all embodiments to effect the techniques described herein. In other embodiments, other means may be used to determine locations of anomalies and other information on a web without departing from the techniques described herein.

Analysis computer 28 processes image streams from acquisition computers 27. Analysis computer 28 processes the digital information with one or more initial algorithms to generate local anomaly information that identifies any regions of web 20 containing anomalies that may ultimately qualify as defects. For each identified anomaly, analysis computer 28 extracts from the image data an anomaly image that contains pixel data encompassing the anomaly and possibly a surrounding portion of web 20. Analysis computer 28 may classify an anomaly into different defect classes if necessary. For instance, there may be unique defect classes to distinguish between spots, scratches, and oil drips. Other classes may distinguish between further types of defects. In accordance with the techniques described herein, analysis computer 28 may further determine in which of products 12 an anomaly may cause a defect.

Based on the position data produced by fiducial mark controller 30, analysis computer 28 determines the spatial position of each anomaly within the coordinate system of the process line. That is, based on the position data from fiducial mark controller 30, analysis computer 28 determines the x, y, and possibly z position for each anomaly within the coordinate system used by the current process line. For example, a coordinate system may be defined such that the x dimension represents a distance across web 20, a y dimension represents a distance along a length of the web, an the z dimension represents a height of the web, which may be based on the number of coatings, materials or other layers previously applied to the web. Moreover, an origin for the x, y, z coordinate system may be defined at a physical location within the process line, and is typically associated with an initial feed placement of the web 20.

In any case, analysis computer 28 records in database 32 the spatial location of each anomaly with respect to the coordinate system of the process line, this information being referred to herein as local anomaly information. That is, analysis computer 28 stores the local anomaly information for web 20, including roll information for the web 20 and position information for each anomaly, within database 32. Analysis computer 28 may also record, for each anomaly, those products of products 12 for which the anomaly may cause a defect. Database 32 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (OR-DBMS) database management system. As one example, database 32 is implemented as a relational database provided by SQL Server™ from Microsoft Corporation.

Once the process has ended, analysis computer 28 transmits the data collected in database 32 to conversion control system 4 via network 9. Specifically, analysis computer 28 communicates the roll information as well as the local anomaly information and respective sub-images to conversion control system 4 for subsequent, offline, detailed analysis. For example, the information may be communicated by way of database synchronization between database 32 and conversion control system 4. In some embodiments, conversion control system 4 may determine those products of products 12 for which each anomaly may cause a defect, rather than analysis computer 28. Once data for the finished web roll 10 has been collected in database 32, the data may be used to mark anomalies on the web roll, either directly on the surface of the web with a removable or washable mark, or on a cover sheet that may be applied to the web before or during marking of anomalies on the web.

Figure 3:
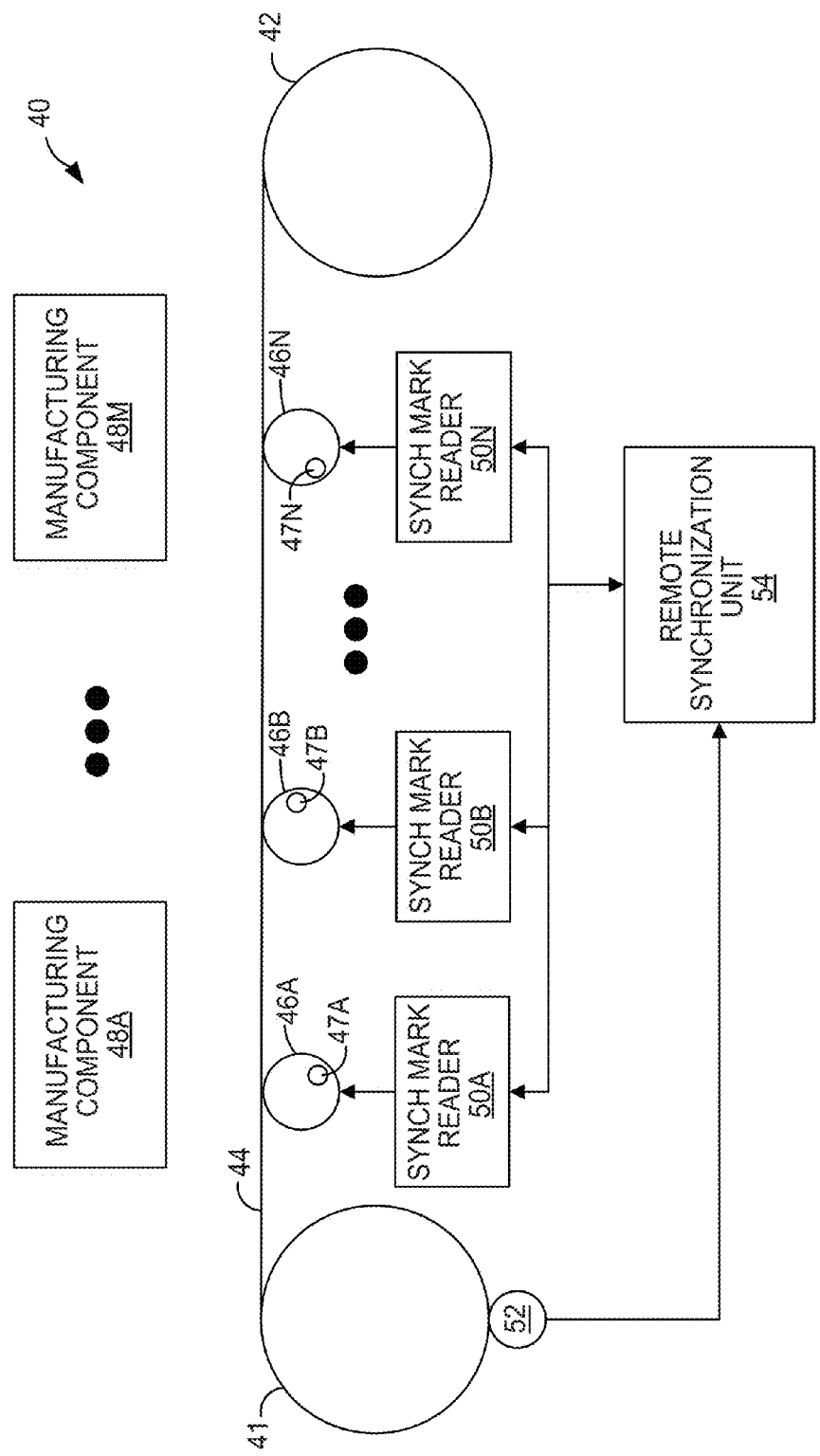
FIG. 3 is a block diagram illustrating an exemplary embodiment of a web manufacturing system in an exemplary embodiment of a web manufacturing plant.

FIG. 3 is a block diagram illustrating further details of an exemplary web process line 40 in an exemplary web manufacturing plant, e.g. web manufacturing plant 6A of FIG. 1. That is, FIG. 3 shows a typical web process line having various rolls. For example, although for simplicity FIG. 2 shows only idler rollers 46A-46N, process line 40 may have numerous types of rollers including idlers, pull rolls, length orienters, coating rolls, and the like. In some cases, web process line may have well over one hundred or more rolls along the entire traversal path of web 40. Manufacturing system 40 may be part of the same manufacturing line as the inspection system of FIG. 2, or manufacturing system 40 may be part of a different manufacturing line than the inspection system of FIG. 2.

Manufacturing system 40 produces web 44, typically by pulling a substrate from lead roller 41 through manufacturing components 48A-48M (manufacturing components 48) to produce web 44 that is collected onto web roller 42. Accordingly, web 44 may traverse web manufacturing components 48, which may manufacture web 44 in various ways. For example, one of manufacturing components 48, e.g. manufacturing component 48A, may apply a coating to web 44.

Idler rollers 46A-46N (idler rollers 46) provide support for web 44 as web 44 traverses web manufacturing system 40. That is, web 44 may rest upon idler rollers 46 while undergoing manufacturing from manufacturing components 48. Although idler rollers 46 may be necessary to properly position web 44, idler rollers 46 may impart anomalies or defects into web 44. For example, one or more of idler rollers 46 may scratch the bottom side of web 44. Although discussed with respect to idler rollers 46, other types of roll, such as casting wheels, pull rolls, nip rolls, microreplicating rolls, or web cleaning components, may be present in web manufacturing system 40, in addition to or in lieu of idler rollers 46. Thus the techniques described herein are not limited to use with idler rollers, but can be applied to any roll of interest within the web process line. The use of idler rollers is merely exemplary for the purpose of demonstration.

The techniques explained herein identify positions of anomalies or defects within the web and correlate those positions with roll synchronization signals. For example, each roll of interest for a web manufacturing process 40 may be equipped with a respective synchronization mark 47A-47N. Further, synchronization mark readers 50A-50N (synchronization mark readers 50) are associated with each one of the rolls of interest (each one of idler rollers 46 in this example) for sensing the respective synchronization mark. Each of synchronization mark readers 50 may detect when the corresponding one of idler rollers 46 has made a full rotation and then emit a roll synchronization signal in the form of a trigger pulse, which remote synchronization unit 54 detects. That is, each of synchronization mark readers 50 may output a short pulse upon a complete rotation of the respective one of rollers 46, and the leading edge of each short pulse may indicate the complete rotation has been detected. In one embodiment, each of synchronization mark readers 50 may be a photo-optic sensor. For example, readers 50 may be from the D10 Family of sensors from Banner Engineering Corp. In general, readers 50 detect corresponding synchronization marks 47 as the marks rotate past the reader. In the example embodiment, synchronization marks 47 may be a target such as a retro-reflecting material or a machined section of the roll. Upon detecting reference point synchronization marks 47 on a corresponding one of rollers 46, the one of readers 50 outputs the synchronization mark signal. Therefore, each of readers 50 outputs a discrete signal for each rotation of the corresponding one of rollers 46.

To aid converting the roll synchronization signals into a spatial domain of a coordinate system associated with web process line 40, a rotational encoder is affixed to one or more rolls along the process line. In this example, rotational encoder 52 is affixed to web roller 41. In other embodiments, an encoder may be used with one or more of rollers 46 in lieu of, or in addition to, encoder 52. Encoder 52, in one embodiment, may be a sine encoder based position sensor. Other embodiments may utilize other types of position sensors or encoders. In general, encoder 52 outputs an electrical pulse train that is directly synchronized to the physical movement of web roller 41. For example, encoder 52 may emit a series of pulses for each rotation of web roller 41. In one embodiment, for example, encoder 52 may emit four million pulses per rotation, thus providing a high degree of positional accuracy.

Remote synchronization unit 54 receives the positional pulses from encoder 52 and the roll synchronization signals from synchronization mark readers 50 and generates a logical map that identifies various sections of web 44 that align with each of idler rollers 46. For example, for each of the rollers, remote synchronization unit 54 divides the spatial domain of the web into a series of sections, each of the sections being as long as the circumference of respective roller. Each web section corresponding to idler roller 46A, for example, is 18.85 inches, i.e. 6.00 inches*π. Each web section corresponding to idler roller 46B is 18.91 inches, and a web section that corresponds to idler roller 46C is 18.79 inches. In this way, remote synchronization unit 54 uses the positional data from encoder 52 as well as roll synchronization signals from synchronization mark readers 50 to convert the roll synchronization signals into the spatial domain of the coordinate system for process 40 for determining web sections within the spatial domain for each or the rollers of interest. As a result, remote synchronization unit 54 need not require a priori data regarding the exact diameter of each of rollers 46 in order to determine the web sections and ultimate detect repeated defects.

In some cases, some or all of the rolls of interest may have approximately the same diameter. For example, a subset or all of idler rollers 46 may have approximately the same diameter of six inches. However, this subset of idler rollers 46 typically does not have exactly the same diameter due to manufacturing variability. For example, the diameter of idler roller 46A may be 6.01 inches, the diameter of idler roller 46B may be 6.02 inches, and the diameter of idler roller 46C may be 5.98 inches. The techniques described leverages averaging captured by calculating variations in the relative offset between a repeated defect and the corresponding roll synchronization signal for a given roller. This provides precise accuracy that allows for repeat defect detection even in manufacturing lines having substantially similar sized rollers but for manufacturing variability in the rollers themselves.

In order to associate an anomaly with one of idler rollers 46, an inspection system may first collect data regarding web 44. Using the pulses from encoder 52 and the roll synchronization signals from synchronization mark readers 50 that has been collected and correlated by remote synchronization unit 54, the inspection system analyzes the anomaly data for the identified web sections for each of the rollers. The inspection system may average the results of the data over many instances of these web sections. For example, in one embodiment, the inspection system may collect 100 instances of web segment data for a given roller. The inspection system then analyzes the data to attempt to distinguish between repeated anomalies and random anomalies. The inspection system may determine that an anomaly is a repeated anomaly, caused by one of idler rollers 46 for example, if an anomaly occurs in a majority of the instances of analyzed web sections for a given roller at or relatively near the same position in those instances in which the anomaly occurs. For example, if idler roller 46A causes an anomaly in web 44, the anomaly will probably be repeated, and the instances of the repeated anomaly should occur approximately 18.85 inches apart, given a diameter of roller 46A of 6.00 inches.

In some arrangements, at least some of the anomalies imparted to web 44 by idler rollers 46 may be healed, i.e. corrected, by the time web 44 is ready to be converted into sheets. In other words, although idler rollers 46 may impart an anomaly into web 44, the anomaly may not cause a defect because the anomaly may be corrected through other manufacturing processes before web 44 is ready to be converted. For example, anomalies imparted to web 44 by idler rollers 46 will be on the bottom side of web 44. Anomalies occurring on the top of web 44 may not be healed or corrected in web 44. That is, anomalies occurring on the top surface of web 44 may cause defects in products 12 if a web segment or individual sheet containing such anomalies is converted into one of products 12. In accordance with the techniques described herein, an inspection system may be able to determine whether an anomaly occurred on the top side or bottom side of web 44. Moreover, the inspection system may be able to trace the source of anomalies occurring on the top side to a particular one of idler rollers 46, for example, idler roller 46A. Accordingly, an operator of manufacturing system 40 may locate the portion of idler roller 46A that caused the anomalies and repair idler roller 46A.

Figure 4:
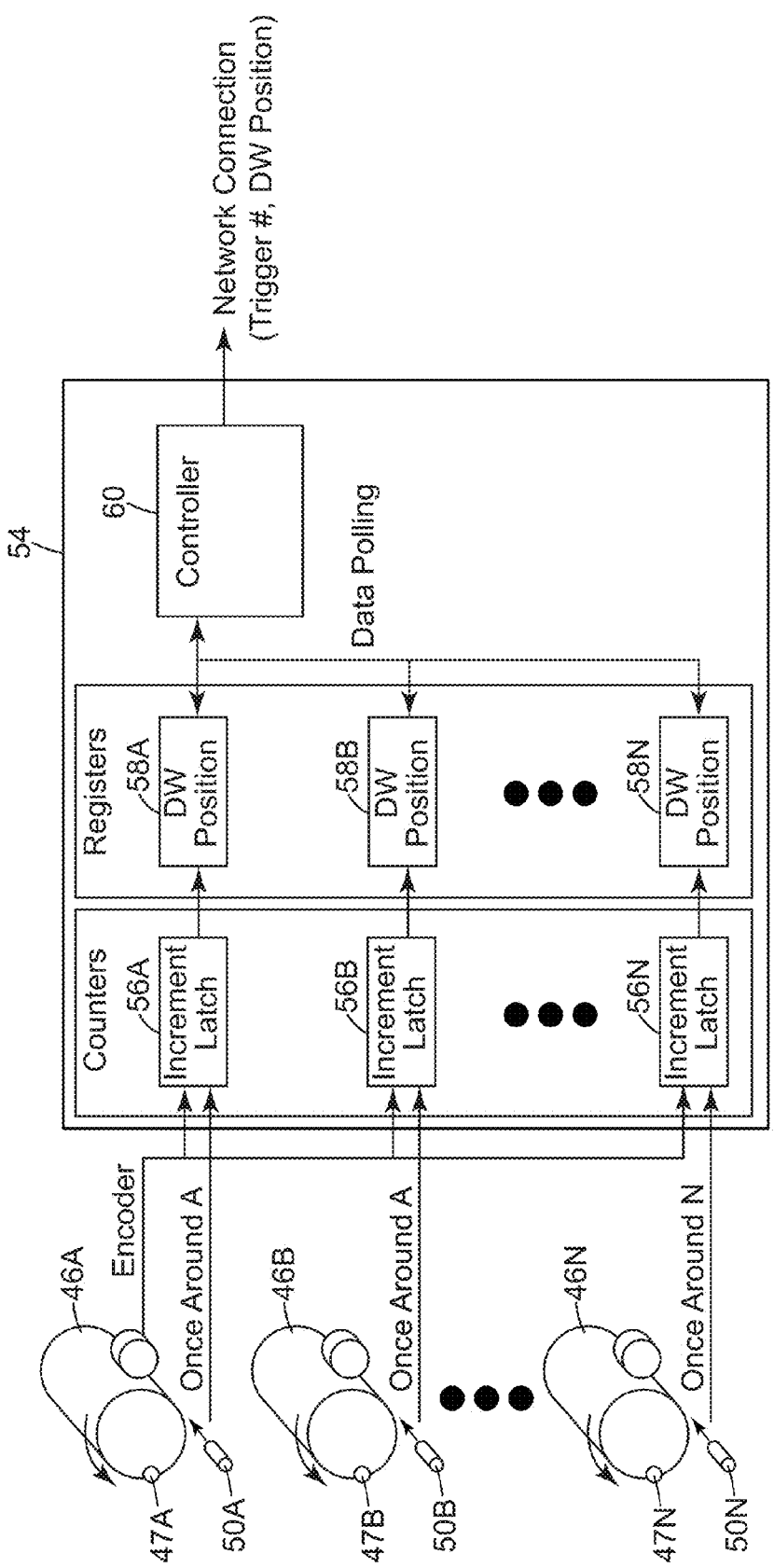
FIG. 4 is a block diagram illustrating an exemplary embodiment of a remote synchronization unit in greater detail.

FIG. 4 is a block diagram illustrating an exemplary embodiment of remote synchronization unit 54 in greater detail. As illustrated in FIG. 3, remote synchronization unit 54 may be electrically coupled to encoder 52 and synchronization mark readers 50 to receive signals therefrom.

In general, example remote synchronization unit 54 senses the occurrence of each roll synchronization signal (illustrated in FIG. 4 as "Once Around" signals A, B-N) is received and converts the signals to a spatial domain relative to the position data from encoder 52. Moreover, synchronization unit 54 outputs positional data identifying the position of synchronization signals that corresponds to one rotation of that respective roller.

In the example embodiment, remote synchronization unit 54 includes counters 56A-56N ("counters 56") and registers 58A-58N ("registers 58"). Each of synchronization mark readers 50 is associated with one of counters 56, which is in turn associated with one of registers 58. The pulse signal from encoder 52 is used as a global increment driving counters 56. That is, as encoder 52 detects web movement, encoder 52 sends a series of pulses that are used to simultaneously increment each of counters 56. In the exemplary embodiment of FIG. 4, roller 46A may include a series of holes around the outer edge of the roller through which a light may shine. Each time encoder 52 detects light through one of the holes, encoder 52 may transmit a signal to each of counters 56. Counters 56, in turn, may receive the pulse train of the encoder signal in parallel and concurrently increment their respective counters.

The roll synchronization signals from each of the rollers are used as triggers for recording the value within the rollers' respective counters. Specifically, during a full rotation of any of rollers 46, the corresponding synchronization mark 47 of that roller will pass the associated synchronization mark reader 50. For example, for each rotation of roller 46A, synchronization mark reader 50A will detect synchronization mark 47A. Upon detecting mark 47A, synchronization mark reader 50A outputs a roll synchronization signal to remote synchronization unit 54 in the form of a short pulse. In response to this pulse, remote synchronization unit 54 latches the current value of the corresponding counter, in this case, counter 56A, into the corresponding data register, register 58A.

Figure 5:
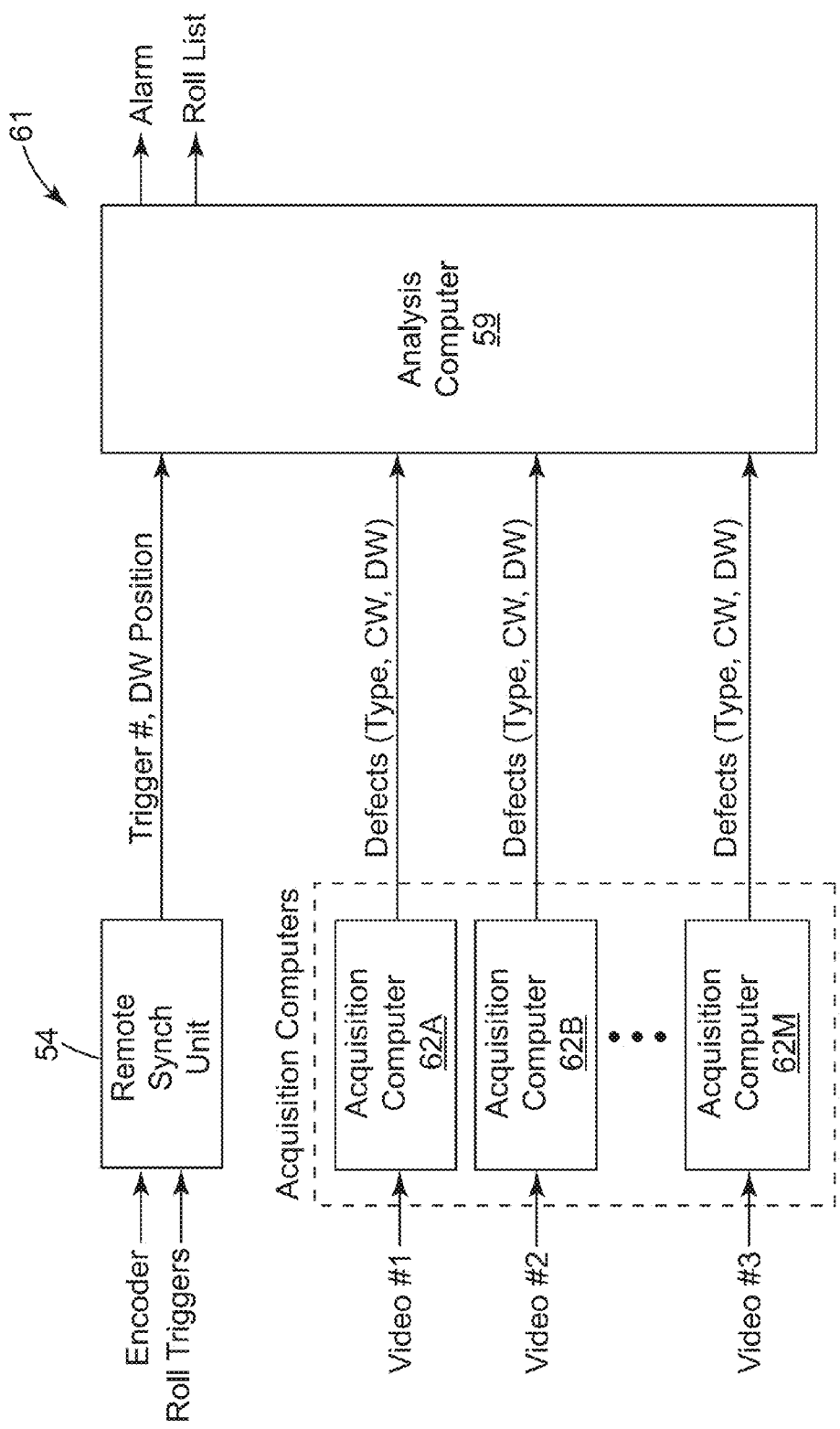
FIG. 5 is a block diagram illustrating a system that combines roll position data with inspection data to determine whether a roller is causing a repeat anomaly, and if so, which of the rollers is causing the repeat anomaly.

Controller 60 polls each of registers 58 at a high rate or is interrupt driven to retrieve the most recent counter data. Accordingly, the polling cycle of controller 60 is faster than the rotations of all of rollers 46. If, upon polling one of registers 58, e.g. register 58A, the counter data is the same as the previous poll, controller 60 may ignore the current counter data. However, if the counter data has changed, controller 60 may retrieve the counter data and transmit the counter data, along with the roller number, to analysis computer 59 (FIG. 5). That is, upon detecting a change to one data register 58, controller 60 of synchronization unit 54 outputs roll position data in the form a current encoder pulse count. Analysis computer 59 can harmonize this roll positional data for each of the rollers with inspection data, as described with respect to FIGS. 5 and 6, in order to determine whether any anomalies are repeat anomalies caused by one of rollers 46, as well as to determine which of rollers 46 is causing the repeat anomaly. Analysis computer 59 may output data to a display to indicate which of rollers 46 caused each set of repeated anomalies. For example, analysis computer 59 may output a graphical representation of portions of the web as well as an indication of the repeated anomalies and the identified roller that caused the repeated anomalies. In addition, analysis computer 59 may output and store data in a database (e.g., database 32) associating the repeated anomalies with the identified roller causing the repeated anomaly.

FIG. 5 is a block diagram illustrating a system 61 in which an analysis computer 59 combines the roll position data from one or more remote synchronization units (e.g., remote synchronization unit 54 of FIGS. 3 and 4) with inspection data to determine whether one of rollers of interest (e.g., any of rollers 46) is causing a repeat anomaly, and if so, which of the rollers is causing the repeat anomaly. Analysis computer 59 may be coupled to one or more web inspections components, as shown by way of example with respect to analysis computer 28, acquisition computers 27 and image acquisition devices 26 of FIG. 2. The use of inspection systems to inspect webs for the presence of anomalies is described in greater detail in co-pending applications "Multi-Unit Process Spatial Synchronization" to Floeder et al., Ser. No. 11/828,369 (now U.S. Pat. No. 8,175,739 B2), filed Jul. 26, 2007, assigned to the assignee of the present application, and "Apparatus and Method for the Automated Marking of Defects on Webs of Material" to Floeder et al., Ser. No. 10/826,995, filed Apr. 19, 2004, assigned to the assignee of the present application, the entire contents of which are hereby incorporated by reference.

In one embodiment, analysis computer 59 may be a server-class computer. In other embodiments, analysis computer 59 may be a distributed computing system or other computing system capable of handling the high amounts of data required for processing the inspection and position information.

As described above, controller 60 of remote synchronization unit 54 transmits roll position data upon detecting a rotation of one of the rollers 46, and the roll position data may be in the form of a roller identification (i.e., a trigger number) and the current encoder position recorded representing the downweb position (DW position) for a given complete rotation of that roller. In some embodiments, encoder 52 may transmit positional pulses both to remote synchronization unit 54 and to the inspection systems to allow correlation within the spatial domain of the web segments of the rolls and detected anomalies. In other embodiments, two distinct encoders may be used to provide positional reference information that is reconciled by analysis computer 59. In still other embodiments, a different means of tracking distance down the web, such as fiducial marks, may be employed by the inspection system. Techniques for using fiducial marks with a web are discussed in co-pending patent application "Fiducial Marking for Multi-Unit Process Spatial Synchronization," Ser. No. 11/828,376 (US 20090028417 A1—now abandoned), to Floeder et al., assigned to the assignee of the present application, filed Jul. 26, 2007, the entire contents of which are hereby incorporated by reference.

In any case, analysis computer 59 correlates the roll position data from remote synchronization unit 54 with positional data of anomalies on the web as determined by the inspection system. Video or other image data may be passed from the inspection sensors to acquisition computers 62A-62M ("acquisition computers 62"). These computers represent software and/or hardware capable of acquiring and processing inspection data for detection of various types of anomalies on the web, e.g. scratches, spots, drips, spills, or other types of anomalies. For example, acquisition computers 62 may be software modules executing on analysis computer 59 or analysis computer 29 of FIG. 2. Alternatively, acquisition computers 62 may be discrete units separate from the analysis computer. In either case, when one of acquisition computers 62 detects an anomaly, for example, when acquisition computers 62A detects an anomaly, sensor 62A outputs anomaly data specifying the type of anomaly, the cross-web position of the anomaly, and the down-web position of the anomaly.

Analysis computer 59 processes the anomaly data and the roll position data to determine whether any anomalies repeatedly occur at substantially the same cross-web position and substantially the same downweb offset within multiple web segments for the same roller. For example, if one of rollers 46 causes a repeated anomaly, the repeated anomaly occurs at substantially the same cross-web position and will repeat with a spacing of the circumference of the corresponding roller, i.e. the circumference of the roller causing the repeated anomaly. In this manner, analysis computer 59 may determine that repeated anomalies are occurring. Moreover, correlating the downweb positions of the repeated anomalies with the downweb positions of the web segments for the different rollers, analysis computer 59 is able to identify which of rollers 46 is causing each of the repeated anomalies.

Figure 6:
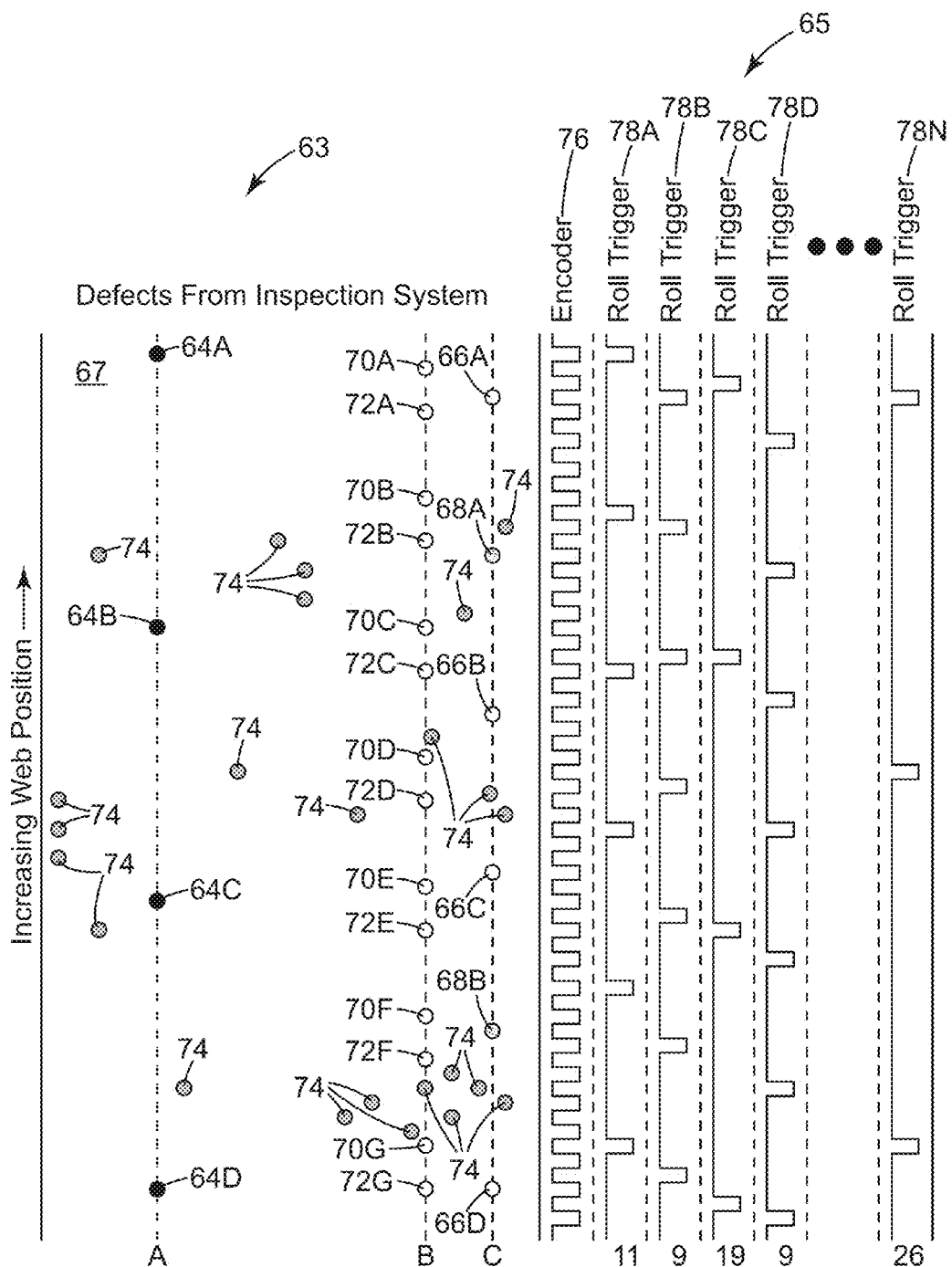
FIG. 6 is a block diagram illustrating an example set of anomaly data and corresponding position data from the rollers.

FIG. 6 is a block diagram illustrating an example set of anomaly data 63 and corresponding roll position data 65. Before processing by analysis computer 59, all anomalies may appear to be the same, that is, random and repeated anomalies may be visually indistinguishable. However, after analysis, analysis computer 59 distinguishes repeated anomalies from random anomalies 74 from repeated anomalies 64, 66, 70, and 72 and may correlate the repeated anomalies with causing rollers using signals 76.

Encoder 52 and synchronization mark readers 50 create a series of pulses that graphically depict the position of each of rollers 46 over time along the downweb length of web 67. Encoder pulses from encoder 52 and synchronization pulses from synchronization mark readers 50 are represented signals 76 and graphs 78A-78N ("graphs 78"), respectively. Based on the data, roll position data, analysis computer 59 determines the number of encoder pulses from encoder 52 that occur between synchronization pulses from one of synchronization mark readers 50. In the example of FIG. 6, roller 46A has 11 encoder pulses per rotation, roller 46C has 19 encoder pulses per rotation, and both rollers 46B and 46D have 9 encoder pulses per rotation.

Analysis computer 59 determines that anomalies 64A-64D ("anomalies 64") are repeat anomalies that occur at a similar cross-web position and that occur, based on their down-web position information, at periodic intervals within a coordinate system associated with the manufactured web. Analysis computer further determines that one of anomalies 64 occurs one encoder pulse after each synchronization pulse from roller 46C. That is, in this example the downweb positions of the anomalies are constant offsets from the start of new web segments for roller 46C. Therefore, analysis computer 59 determines that repeated anomalies 64 are caused by roller 46C. An operator may then inspect roller 46C at the cross-web position of repeated anomalies 64 and either repair or replace roller 46C.

Similarly, a set of anomalies 66A-66D ("anomalies 66") all occur at the same cross-web position. However, there are missing anomalies 68A and 68B that were expected to occur. It is possible that the offending roller did not cause an anomaly, or that the inspection system failed to detect an anomaly at one or both of positions 68A and 68B. In either case, however, analysis computer 59 may still determine the presence of a repeated anomaly. This is because, even with missing anomalies 68A and 68B, analysis computer 59 determines the presence of a repeated anomaly when a majority of the new web segments for a roller contain anomalies in the same cross-web position and substantially at the same distance from the synchronization pulses, i.e., the start of a new web segment for that roller. In this case, each of repeated anomalies 66 occur 7 encoder pulses after a majority of synchronization pulses of signal 78A. Therefore, analysis computer 59 may determine that roller 46A is causing a repeated anomaly.

The techniques described herein may even be used to detect repeated anomalies 70A-70G ("repeated anomalies 70") and repeated anomalies 72A-72G ("repeated anomalies 72") and to distinguish repeated anomalies 70 from repeated anomalies 72. Repeated anomalies 70 and repeated anomalies 72 each occur at the same cross-web position. Repeated anomalies 70 each occur 1 encoder pulse after a synchronization pulse of graph 78B and 4 encoder pulses after a synchronization pulse of graph 78D. Repeated anomalies 72 each occur 7 encoder pulses after a synchronization pulse of graph 78B and 1 encoder pulse after a synchronization pulse of graph 78D. Although it would appear that either of rollers 46B or 46D could be causing either of these repeated defects, analysis computer 59 may still determine which of repeated defects 70 and 72 are caused by rollers 46B and 46D, because the diameters of rollers 46B and 46D likely differ by some detectable amount. For ease of visualization and readability, a small number of encoder pulses is shown in the example of FIG. 6. However, in many embodiments, far more encoder pulses are used between synchronization pulses. In one embodiment, for example, as many as four million encoder pulses may occur between synchronization pulses. At this resolution, it is possible to detect even extremely small differences in position over time. Therefore, if two distinct rollers with nominally the same diameter are causing two sets of repeated defects in the same cross-web position, when related to the synchronization pulses for one of the two rollers, one set of anomalies will appear stationary while the other set will appear to be sliding. This is illustrated conceptually in FIGS. 7 and 8.

Figure 7:
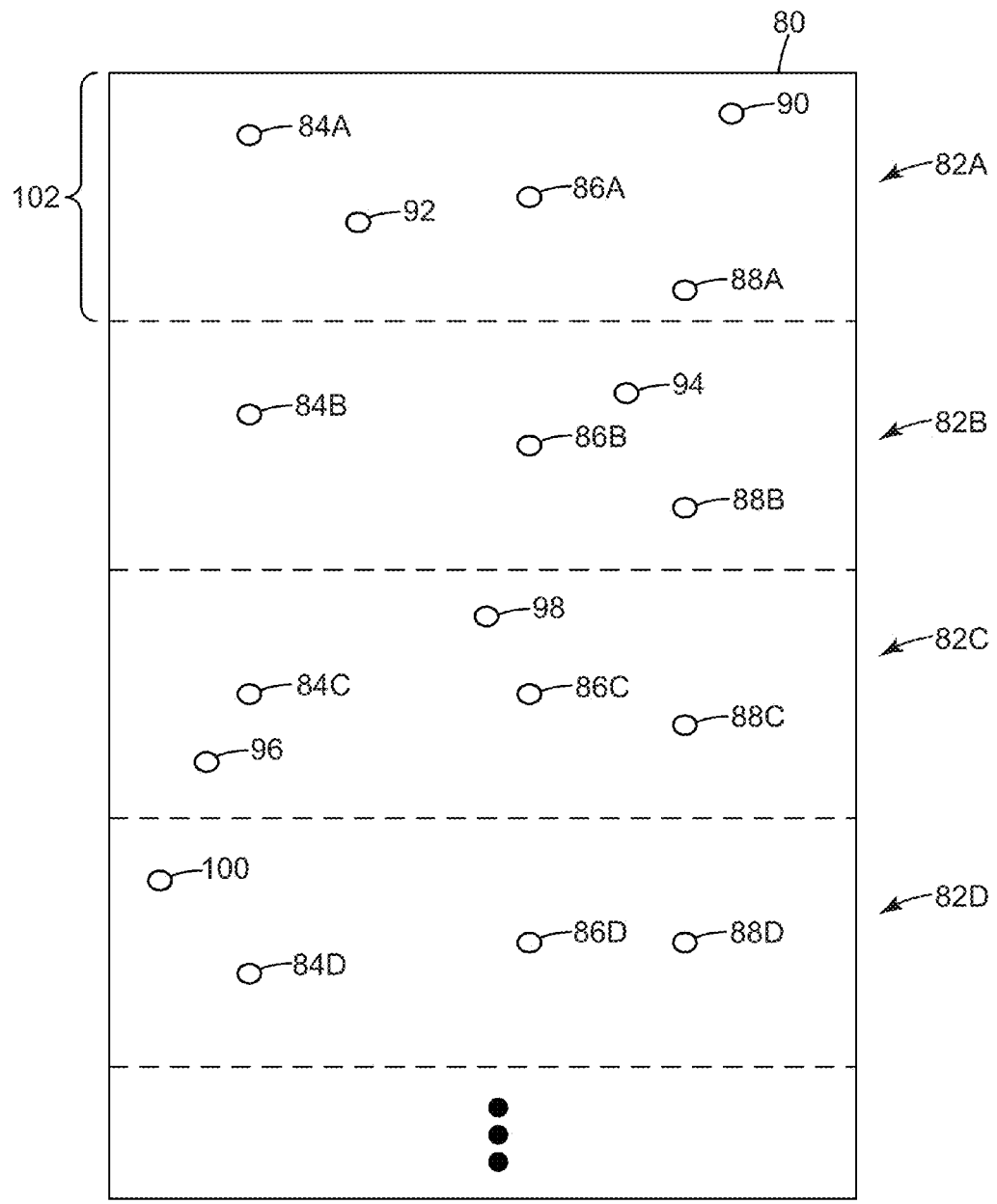
FIG. 7 is a block diagram illustrating an example web with several occurrences of random and repeated anomalies

FIG. 7 is a block diagram illustrating an example web 80 with several occurrences of random and repeated anomalies. Web 80 may correspond to, for example, web 44. In this example, web 80 may have traversed three idler rollers, e.g. idler rollers 46A, 46B, and 46C. Idler rollers 46A, 46B, and 46C may have the same nominal diameter of six inches, but the actual diameters may differ slightly for each of the rollers. Synchronization marks corresponding to idler rollers 46 are used to logically determine web segments for a given roller. In the example of FIG. 7, dashed lines are used to indicate the divisions between web segments 82A-82D (web segments 82), that is, the dashed lines represent synchronization pulses from one of the synchronization mark readers 50 for one of the rollers 46. Each dashed line occurs after a constant distance 102, which corresponds to one of the circumferences of idler rollers 46, i.e. the distance between synchronization pulses. In this case, for example, distance 102 may be 18.85 inches.

Because of this segmentation, it is possible to determine whether, for example, idler roller 46A is causing any of the anomalies on web 44. Web segment 82A includes anomalies 84A, 86A, 88A, 90, and 92. Web segment 82B includes anomalies 84B, 86B, 88B, and 94. Web segment 82C includes anomalies 84C, 86C, 88C, 96, and 98. Web segment 82D includes anomalies 84D, 86D, 88D, and 80. To determine whether any of these anomalies is a repeated anomaly caused by idler roller 46A, the analysis computer determines the distance between each anomaly and each synchronization pulse, i.e. the beginning of each web segment as represented by each dashed line. Although only four web segments 82 are shown in FIG. 7 for purposes of illustration, many more segments may be used for analysis. In one embodiment, for example, the analysis computer may analyze a hundred web segments before making decisions regarding repeated anomalies.

The analysis computer repeats this analysis for each of the rollers. That is, the analysis computer segments the web in a similar manner for each synchronization pulse, allowing the computer to identify the specific source of the repeated anomalies.

Figure 8:
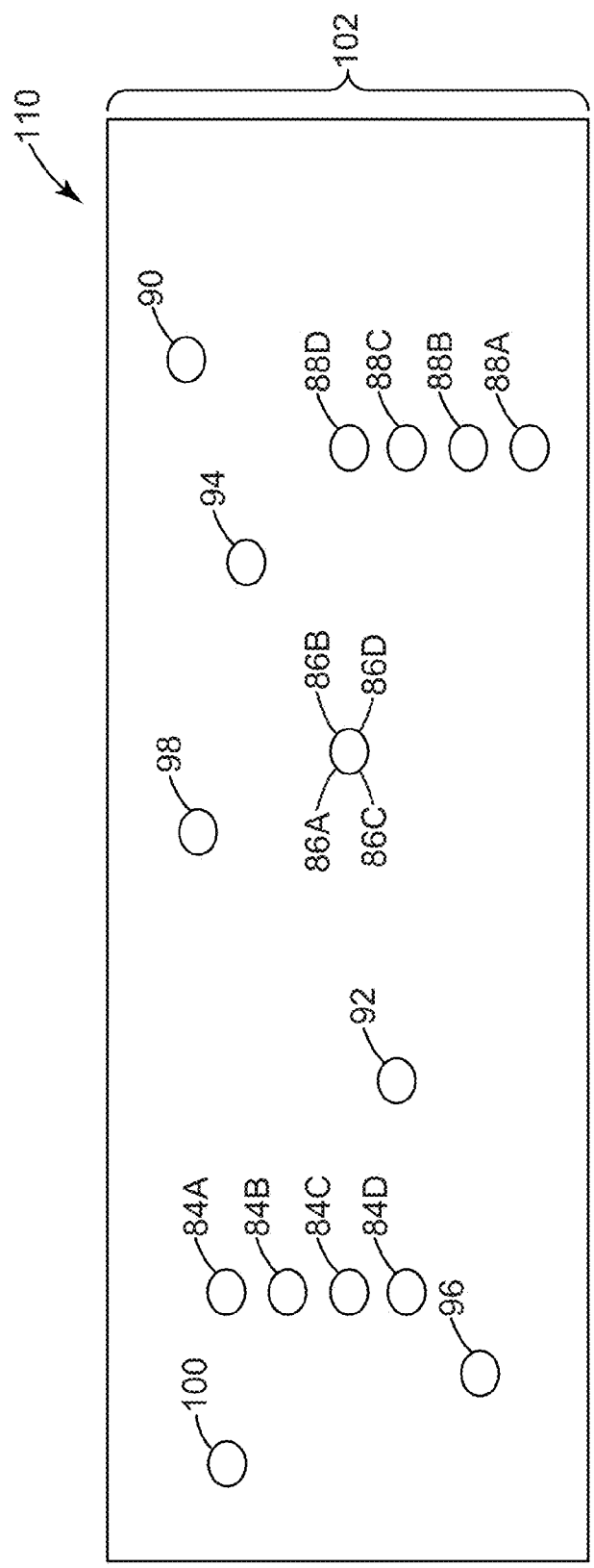
FIG. 8 is a block diagram illustrating an example composite map formed from the data of FIG. 7.

FIG. 8 is a block diagram illustrating an example composite map 110 formed from the data of FIG. 7 as segmented for a single roller. That is, composite map 110 has a total down-web length 102 (18.85 inches in this example), where each of the web segments are overlaid. As a result, composite map 110 includes the anomalies from each of the web segments 82 of web 80, and those anomalies have been spatially registered to the start of the web segment as defined by the synchronization pulses for that particular roller.

In composite map 110, anomalies 84, 86, and 88 each appear to be repeated anomalies. However, composite map 110 shows that repeated anomalies 84 shift in the down-web direction during different web segments. That is, anomalies 84 and 88 may be repeated anomalies, but they are not repeated at the interval of the circumference of idler roller 46A. Analysis computer 59 may determine this by determining that the distance from the synchronization pulse for this specific roller to each of anomalies 84 and 88 exceeds a threshold difference for each instance of anomalies 84 and 88.

In contrast, anomalies 86 are repeated anomalies and caused by the roller for which the data has been segmented because, as shown by composite map 110, they are spaced at substantially the same interval of the circumference of idler roller 46A. That is, for each instance of anomalies 86, the distance between the synchronization pulse and the instance of anomalies 86 is within a tolerance distance. The tolerance distance may, for example, be ±2 pulses depending on the positional resolution of the encoder. Therefore, the inspection system may determine that anomalies 86 are repeated anomalies caused by idler roller 46A. For example, anomalies 86 may be scratches on the bottom side of web 80 caused by a rough spot on idler roller 46A. Using this determination, an operator may attempt to repair idler roller 46A at this position to prevent idler roller 46A from causing more anomalies.

In some embodiments, the inspection system may be reprogrammed to disregard anomalies occurring at a similar position in later web segments, as these anomalies will very likely not actually cause a defect once web 80 is finally converted into products. That is, nearly all of anomalies caused by idlers or other rollers known to be located on a bottom side of the web may be cured at some point during the manufacturing of web 80.

The random anomalies 90, 92, 94, 96, 98, and 80 of web 80, however, probably occurred on the top side of web 80, and anomalies 90, 92, 94, 96, 98, and 80 will probably not be cured during the remainder of the manufacturing of web 80. Therefore, the inspection system may mark the positions of these anomalies in a database, such as database 32 of FIG. 2, or on the surface of the web, and the system may also note that these anomalies will likely cause defects once web 80 is converted into products.

Figure 9:
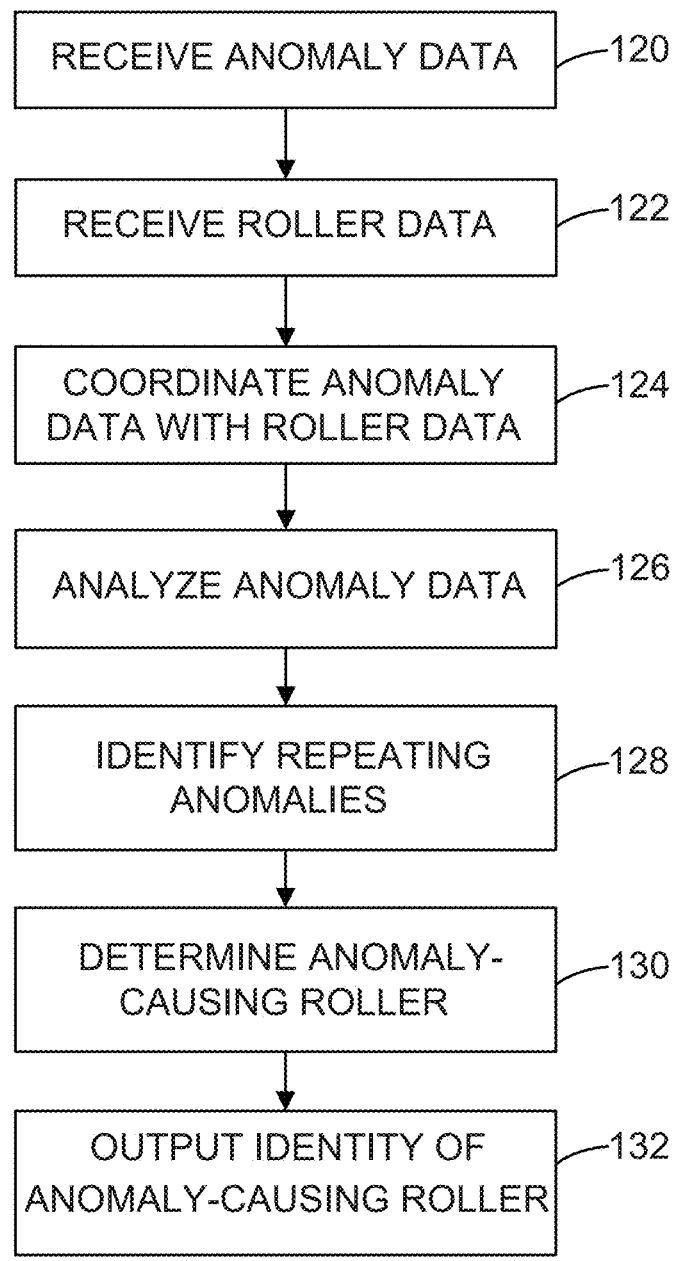
FIG. 9 is a flowchart illustrating an exemplary method for identifying a roller that is causing a repeated anomaly.

FIG. 9 is a flowchart illustrating an exemplary method for identifying a roller that is causing a repeated anomaly. The method is discussed with respect to analysis computer 59, although the method is not limited to performance by a single computer. Initially, analysis computer 59 receives anomaly data from sensors 62 (120). As discussed above, sensors 62 represent software and/or hardware capable of acquiring and processing inspection data for detection of various types of anomalies on the web, e.g. scratches, spots, drips, spills, or other types of anomalies. The anomaly data output by sensors 62 includes both the crossweb and downweb positions of the anomalies on a web, such as web 44 of FIG. 3. The anomaly data may further include anomaly type information that may identify what type of anomaly the identified anomaly is, such as a hole, a pit, a scratch, a discoloration, or other type of anomaly.

Analysis computer 59 also receives roller data (122). The roller data may include identifications of each roller, as well as data characterizing the occurrences of complete rotations of each roller. For example, the roller data may identify roller 46A using a unique identifier or label, which may be assigned by a user, and include trigger numbers (e.g., a sequence number) and a down web position for each instance when synchronization mark reader 50A read synchronization mark 47A.

Analysis computer may process the anomaly data to identify repeat anomalies, and may correlate the received anomaly data with the received roller data to register the anomalies to offending elements (124). Initially, analysis computer 59 processes the roller data to logically partition the web into a series of segments, and may repartition the web in a similar manner for each roller of interest. That is, for each roller of interest, the length of each segment in the series is defined by the distance between two sequential trigger signals from its corresponding one of synchronization mark readers 50. As a result, the length of each of the segments for that partitioning is substantially equal to the circumference of the corresponding one of rollers 46. For example, analysis computer 59 may logically partition the web into a set of segments for roller 46A. The down web distance between signals from synchronization mark reader 50A with respect to a coordinate system of the process line will, accordingly, be equal to the circumference of roller 46A. As described in greater detail below, the anomaly data for each of these logical segments for a given roll of interest may be analyzed to determine the presence of anomalies in substantially common positions within the segments, that is, anomalies that occur at a common cross-web location and a common down-web distance from the beginning of all or a threshold number of the logical segment. This threshold, in one embodiment, may be a majority of the segments. In some embodiments, the width of each segment may be the width of the web. In other embodiments, such as that described with respect to FIG. 10, the web may be subdivided into lanes in the cross-web direction, such that the width of the segments are defined by the width of the corresponding lane.

Based on the logical partitioning of the web for each of the rollers of interest, analysis computer 59 identifies positions of anomalies on each of the segments. In this manner, analysis computer 59 determines the positions of each anomaly relative to each rotation of each roller. Analysis computer 59 then analyzes the anomaly data (126) to determine the presence of repeating anomalies (128). Analysis computer 59 determines, for each roller, whether an anomaly is occurring in substantially the same position relative to the rotation of the roller. That is, analysis computer 59 determines whether any of the anomalies is in substantially the same position on the logical segments for any of the rollers. For example, analysis computer 59 may determine that an anomaly occurs 16 inches cross-web and five inches down-web for all or for a threshold number of the segments for a given partitioning.

By determining the presence of a repeating anomaly, analysis computer 59 may then identify the anomaly-causing roller of rollers 46 (130). For example, analysis computer 59 may determine that roller 46A is causing a repeated anomaly because the anomaly at issue occurs substantially the same cross web and down web location after each rotation of roller 46A. In response, analysis computer 59 may output the identity of the anomaly-causing roller (132). For example, analysis computer 59 may output the identity to a computer screen. Other means of identifying the anomaly-causing roller may also be used, such as, for example, causing a light on or near the offending roller to illuminate. As another example, analysis computer could illuminate a light-emitting diode (LED) that is associated with the offending roller, wherein each roller is associated with an LED and the LEDs may be positioned on a board to provide a central viewing location to an operator. Additionally, analysis computer 59 may further output the position of the anomaly to assist an operator in repair of the offending roller. The operator may determine the position of the synchronization mark on the roller and, using the position of the anomaly, inspect the roller at the position of the repeated anomaly to determine whether the repeated anomaly-causing element is repairable.

Figure 10:
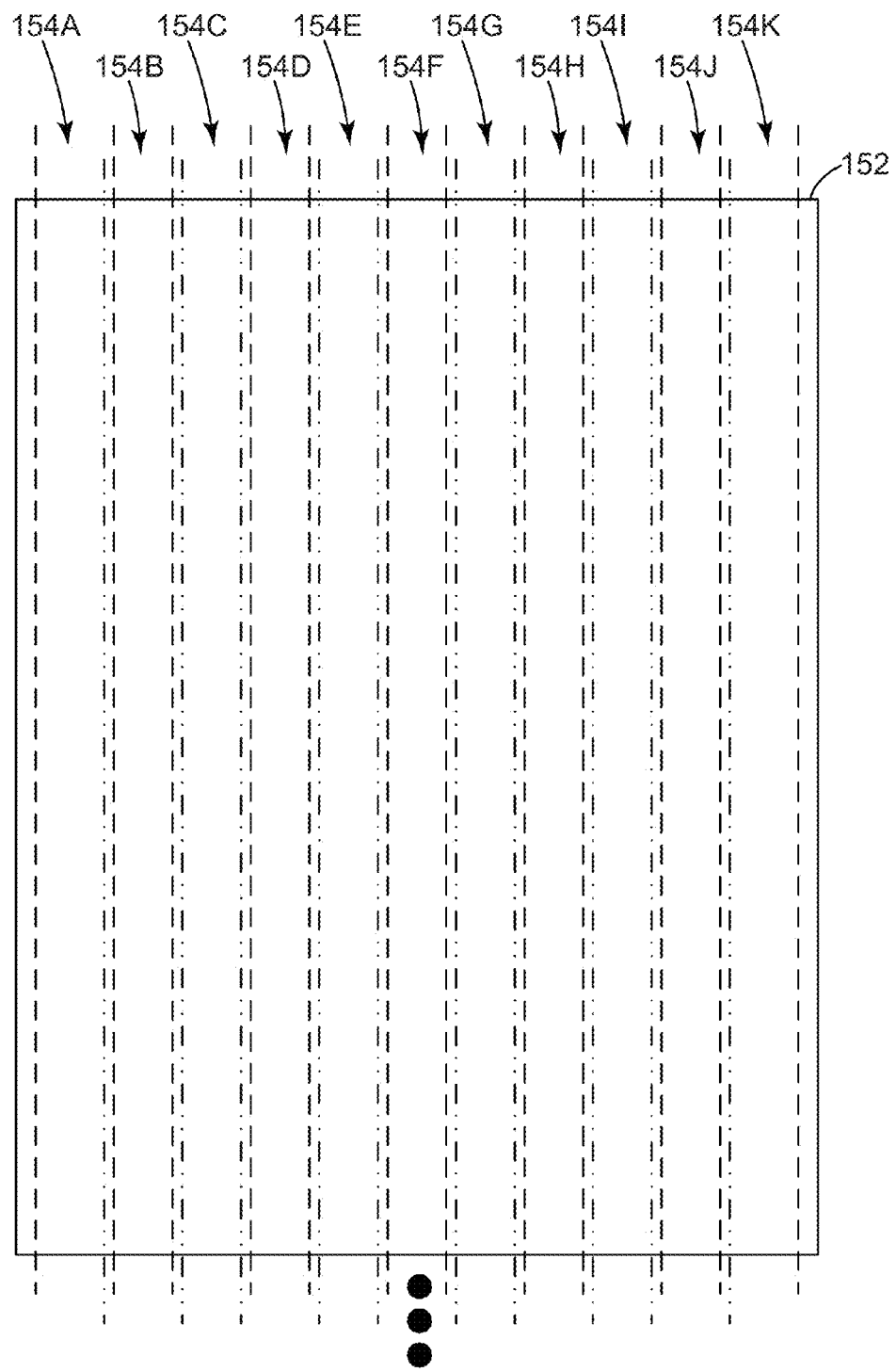
FIG. 10 is a block diagram illustrating an example web that is divided into lanes for analysis of each lane.

FIG. 10 is a block diagram illustrating an example web 152 that is logically divided into lanes 154A-154K ("lanes 154") for analysis of each lane. In one embodiment, in order to determine whether there is an occurrence of a repeating anomaly, web 152, which may represent web 67, for example, may be divided into lanes, such as lanes 154. An analysis system, such as the inspection system of FIG. 2, may inspect each of lanes 154 individually. Because repeated anomalies will occur in the same general cross-web position, division of web 152 into lanes 154 may increase the efficiency of data gathering. That is, each lane may be inspected individually without regard for anomalies occurring in the other lanes.

In the example embodiment of FIG. 10, web 152 has been divided into lanes 154A-154K. The number of lanes depicted is merely exemplary, and the choice of the number of lanes may be made as a result of the size of web 152, the number of inspection devices available, or other factors. Lanes 154A, 154C, 154E, 154I, and 154K are demarcated by dashed lines, whereas lanes 154B, 154D, 154F, 154H, and 154J are demarcated by dashed-dotted lines. In the example of FIG. 10, adjacent lanes overlap slightly so that an occurrence of a repeating anomaly along the edge of a lane will be detected as well as repeating anomalies occurring in the center of the lane. Lane widths as small as 5 mm have proven useful.

Image acquisition devices, such as image acquisition devices 26 of FIG. 2, may inspect web 152 at lanes 154. One of image acquisition devices 26 may inspect each of lanes 154. Analysis computers 27 may determine whether corresponding image acquisition devices 26 have detected an anomaly, as described with respect to FIG. 2. Moreover, analysis computer 59 of FIG. 5 may determine whether a repeated anomaly is occurring in any of lanes 154. In one embodiment, analysis computer 59 may use the algorithm described with respect to FIG. 11 to determine the presence of a repeating anomaly in one of lanes 154.

Because a repeating anomaly may occur in an overlap of lanes, such as in the overlapping region between lanes 154A and 154B, such an anomaly may be detected twice. The inspection system may use various factors to reconcile such a duplicate detection. For example, the inspection system may compare the cross-web position of the repeated anomalies, as well as the down-web position of each instance of the anomalies and the repeat interval between instances. When two repeated anomalies are discovered with the same cross-web position and instances of the anomalies occurring at the same down-web positions at the same interval, the system may discard one of the repeating anomalies so as not to trigger two alerts for the same repeating anomaly.

Figure 11:
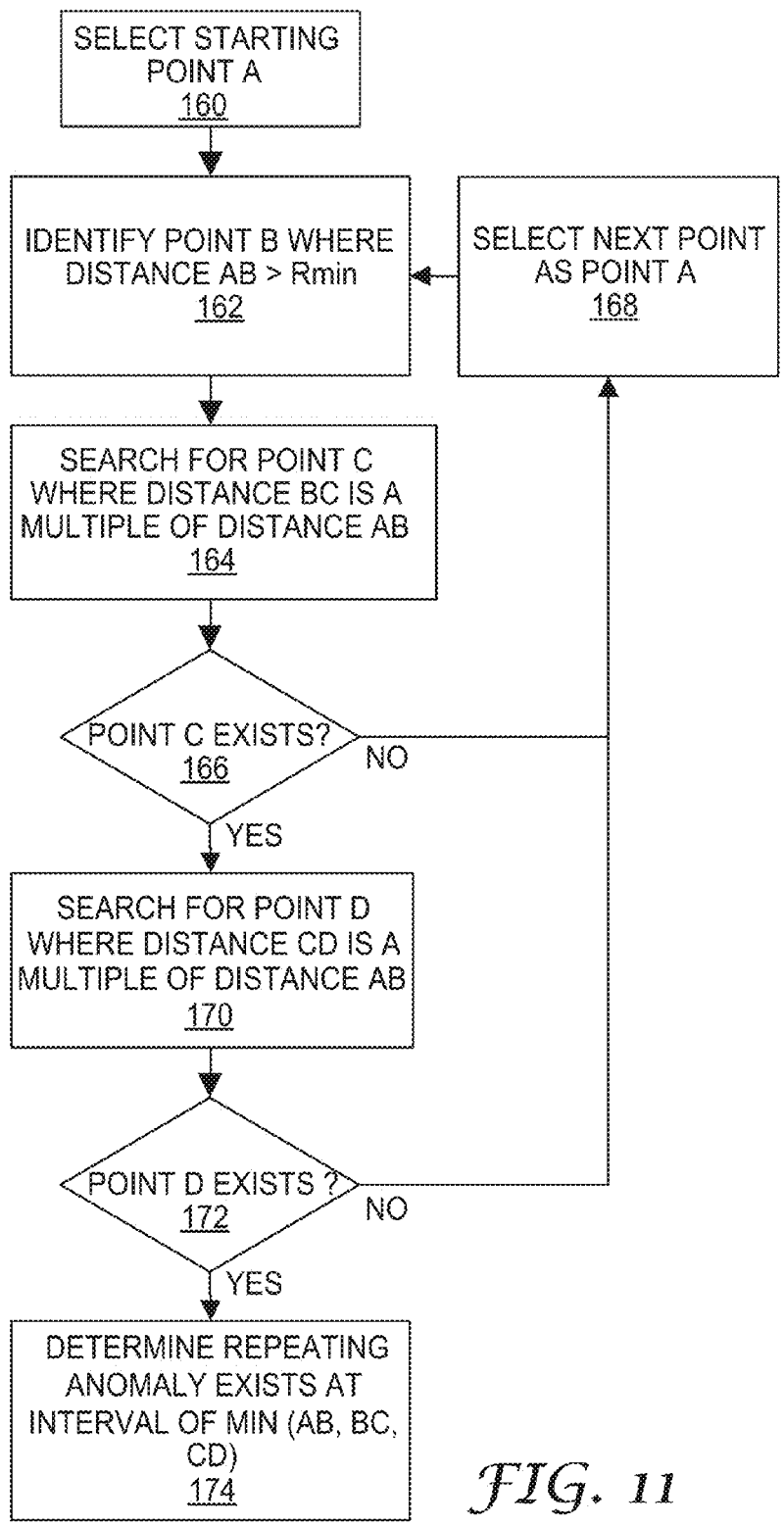
FIG. 11 is a flowchart illustrating an exemplary algorithm for determining the presence of a repeated anomaly.

FIG. 11 is a flowchart illustrating another exemplary algorithm for determining the presence of a repeated anomaly. The method of FIG. 11 may be used to effect the result of step 128 of FIG. 9 in one exemplary embodiment. In one embodiment, the method of FIG. 11 may be separately applied to data gathered from each of lanes 154 of FIG. 10, such as, for example, lane 154A.

Initially, analysis computer 59, in an example embodiment, determines a starting point A, which may be a first detected anomaly (160). As discussed above, a repeating anomaly is an anomaly that is caused by an element of a web production or manufacturing system, such as an idler roller. Therefore, there is a certain distance, herein referred to as "$R_{min}$," which is the minimum possible repeating distance for a repeated anomaly. For example, in the case of repeated anomalies caused by one or more of a plurality of idler rollers used within a web process, $R_{min}$ is the circumference of the smallest idler roller of interest. Accordingly, analysis computer 59 may search for a point B in lane 154A such that the cross-web position of points A and B are the same and the down-web distance between points A and B is at least $R_{min}$ (162).

Analysis computer 59 may then determine whether a point C exists in lane 154A such that the cross-web position of point C is the same as that of A and B and such that the down-web distance between points B and C is a certain multiple of the distance between points A and B (164). A repeated anomaly may not repeat in every expected instance. Several instances of the repeated anomaly may be skipped, as discussed with respect to FIG. 6. In determining whether point C is an instance of a repeated anomaly, therefore, the exemplary embodiment determines whether the distance between points B and C is a multiple of the distance between points A and B. In one exemplary embodiment, the multiple may be one of 1, ½, ⅓, 2, or 3. That is, based on the detection capability for a given application, an expert user can predefine the number of integer multiples to be used for identifying sparsely repeating defects. For example, for a given system with very high detection capability, the integer multiple may be 1 while a second system with lower detection capability may use a multiple of 5. The first examines only a single downweb distance from a given anomaly while the second examines multiples of 1, 2, 3, 4, 5 and ½, ⅓, ¼, and ⅕. Note, the computational complexity increases with increased multiples. In practice multiples of 3 may be generally sufficient.

If no point C can be found at a distance from point B that is, for example, 1, ½, ⅓, 2, or 3 times the distance between points A and B ("NO" branch of 166), analysis computer 59 may obtain a new starting point anomaly A (168) and attempt to determine whether the new starting point is part of a repeating anomaly. If analysis computer 59 does find such a point C, however, ("YES" branch of 166), analysis computer 59 may then search for a point D where the distance between points C and D is a multiple of the distance between points A and B (170). In one embodiment, the same set of potential multiples may be used as in step 164, e.g. 1, ½, ⅓, 2, and 3. Point D may be used to confirm that points A, B, and C are indeed part of a sequence of repeating anomalies.

If no point D is found ("NO" branch of 172), analysis computer 59 may again restart the process of selecting a new starting anomaly point A (168). No point D may be found if, for example, anomalies at points A, B, and C were not part of a repeating anomaly and the distances between points A and B and between points B and C were merely coincidental. However, if analysis computer 59 does find a point D ("YES" branch of 172), it is quite likely that points A, B, C, and D make up a column of repeated anomalies. Therefore, analysis computer 59 may determine a repeat distance as the minimum of the distances between points A and B, points B and C, and points C and D (174). Analysis computer 59 may then expect to discover anomalies repeated at the determined repeat distance from point D at the cross-web position of points A, B, C, and D. Analysis computer 59 may analyze each of lanes 154 to discover repeated anomalies in a similar manner.

After having determined a repeated anomaly, analysis computer 59 may determine the source roller of the repeated anomaly, per the method of FIG. 9. For example, analysis computer 59 may calculate an offset between one instance of a repeated anomaly and point A, i.e. the first recognized instance of the repeated anomaly. Analysis computer 59 may then use this offset to project an estimated position of the one of synchronization marks 47 corresponding to the one of rollers 46 under analysis. Analysis computer 59 may then determine whether the synchronization mark was recorded within a certain error tolerance of the estimated position. If the synchronization mark was recorded at the estimated position, or within a predetermined tolerance level of the estimated position, then the roller corresponding to the analyzed synchronization mark is the offending roller. However, if the synchronization mark was not recorded at the estimated position or within the tolerance level, the roller corresponding to the synchronization mark is not the roller causing the repeated anomaly.

The error tolerance applied by analysis computer 59 may be a function of the expected number of complete rotations separating the anomalies. For example, for two nearly identical rollers having diameters of 20.000 cm and 20.0001 cm, the down web distance separating two repeat intervals for the rollers will be approximately 62.800 cm and 62.803 cm, which may be too small to measure. However, after 50 expected complete rotations for the rollers, the down web positions of the end of the web segment will be 3140 cm and 3140.15 cm, yielding a positional difference of 0.15 cm, which is a measureable error tolerance applied by analysis computer 59.

As an example, the first position, i.e. the position of point A, for a repeated anomaly series may have been recorded at 0.4924 m and the $n^{th}$ instance of a repeated anomaly may have occurred at a down-web distance of 79.5302 m. The offset would then be 79.1008 m (79.5302 m−0.4924 m). The first synchronization mark of roller 46A (FIG. 3) may have been read by synchronization mark reader 50A at position 0.0012 m. Therefore, if roller 46A is causing the repeated anomalies, the position recorded for synchronization mark 47A nearest the $n^{th}$ anomaly in the series should be relatively near 79.1020 m (0.0012 m+79.1008 m). If the synchronization mark nearest the analyzed anomaly was actually recorded at 78.7508 m, the error would be 0.3512 m, which is significant enough to determine that roller 46A is not the roller causing the repeated anomaly. However, the first recorded synchronization mark for roller 46B may have been at 0.0001 m. Therefore, the position recorded for synchronization mark 47B may be expected at 79.1009 m (79.1008 m+0.0001 m). If the actual recorded position of synchronization mark 47B was 79.1018 m, then the error would only be 0.0009 m, which would indicate that roller 46B is causing the repeated anomaly.

Although discussed with respect to the use of lanes 154, the method described above is not limited to the use of lanes 154. For example, the method may be applied to a full web 152 that has not been divided into lanes 154. In another example embodiment, multiple analysis computers may be used, one analysis computer for each lane, rather than a single analysis computer 59. For example, acquisition computers 27 of FIG. 2 may be programmed to effect the method of FIG. 11 for corresponding lanes 154. Each of acquisition computers 27 may then upload the discovered repeated anomalies to analysis computer 59 for reconciliation. The method described above may be encoded into a computer-readable storage medium in the form of software instructions that cause a processor of a computer to perform the steps of the method.

Figure 12:
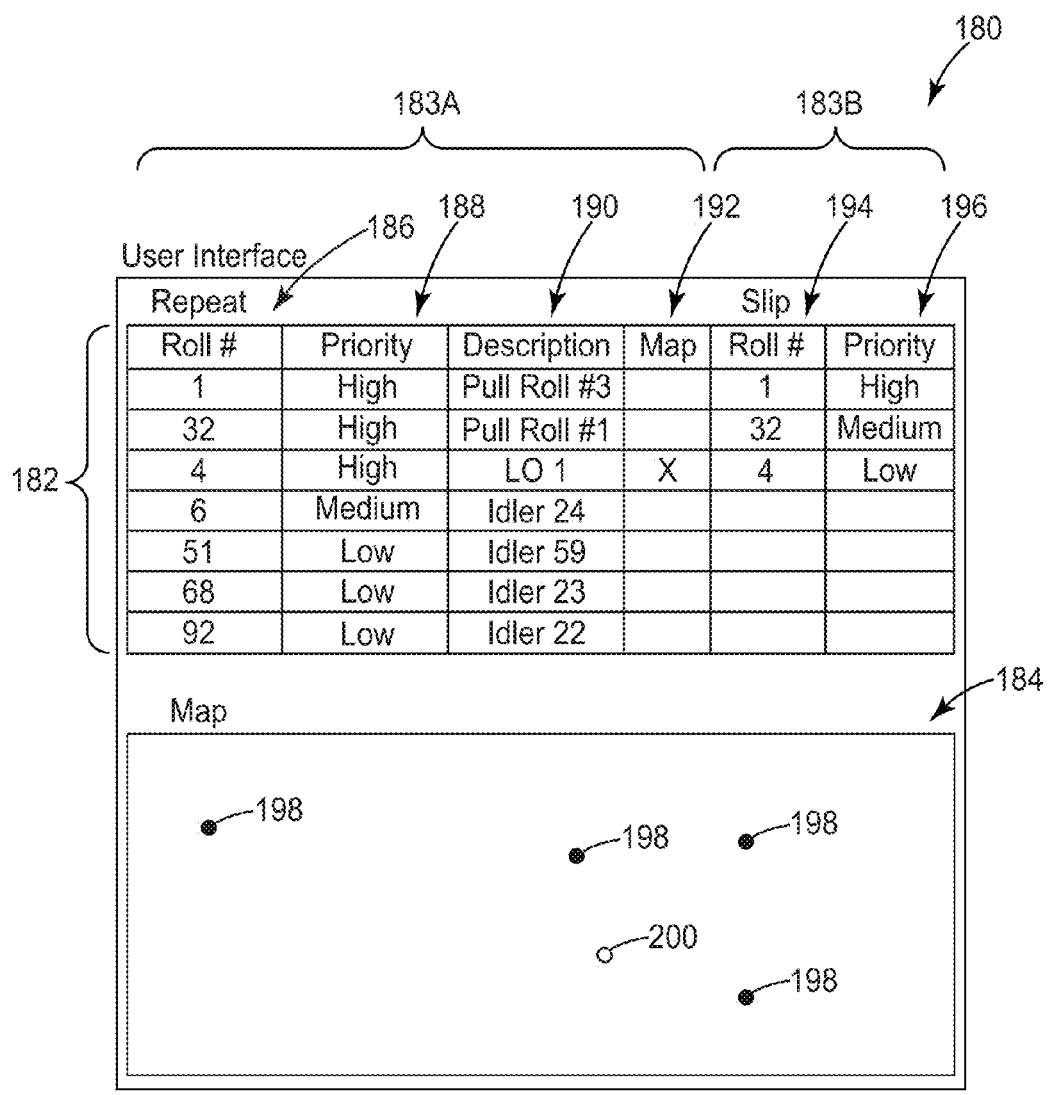
FIG. 12 is a block diagram illustrating an exemplary user interface.

FIG. 12 is a block diagram illustrating an exemplary user interface 180. User interface 180 may be implemented as a graphical user interface ("GUI") depicting a variety of information. For example, user interface 180 may include data output area 182. Data output area 182 may display various raw and/or summarized data for a user interacting with the system, for example, through analysis computer 59.

In the exemplary embodiment of FIG. 12, data output area 182 includes a "repeat" area 183A that displays information on detected repeated anomalies, as well as a "slip" area 183B that displays information regarding detected roll slip. Repeat area 183A includes roll identifier column 186, priority column 188, action description column 190, and map column 192. Entries in roll identifier column 186 identify the roll to which the entries in the row correspond. For example, the first entry in roll identifier column 186 is "1", indicating that the row includes information on the roll identified as "1".

Entries in priority column 188 indicate to a user how important or significant the detected repeated anomaly is. In the example of FIG. 12, the priority is illustrated as "high", "medium", or "low". Other embodiments may use different priority levels and indicators, such as "green", "yellow", or "red", or a numeric scale, e.g. 1-10.

Entries in action description column 190 indicate to a user the suggested or required action that the user should take. For example, the first entry in description column 190 is "pull roll #3". A user viewing this display should replace the roller identified with the number "3" with a new roller. Moreover, given a priority of "high" in priority column 188, a user should replace roll "3" as soon as possible.

Map column 192 allows a user to select a roller and view the composite map on map screen 184. For example, a user may use a mouse connected to analysis computer 59 to direct a pointer to one of the cells in column 192 and press a button to select the corresponding roller. In the example of FIG. 12, a user has selected roll "4". Accordingly, analysis computer 59 has displayed the composite map corresponding to roll "4" in map window 184. The composite map in window 184 may be similar to composite map 110 of FIG. 8. Analysis computer 59 may display map 184 in the same window as data output area 182 or as a distinct window. Analysis computer 59 may display random anomalies 198 and distinguish them from detected repeated anomalies 200 in map 184. For example, in one embodiment, random anomalies 198 may appear in one color, such as black, while repeated anomalies 200 may appear in a different color, such as red. In another embodiment, the number of occurrences of an anomaly in a certain position over a number of instances may dictate the color in which the anomalies are displayed in map 184. For example, map 184 may display a composite map over the last 20 instances of data gathered for roller "4". An anomaly occurring at a particular location on the composite map only once may be displayed in black. An anomaly occurring between 2 and 5 times in the same location on the composite map may be displayed in green. An anomaly occurring between 6 and 10 times may be displayed in yellow. An anomaly occurring 11 or more times may be displayed in red.

Slip area 183B displays information regarding whether rollers slip as the web traverses the manufacturing system. This slip may be caused, for example, when the web does not make constant contact with the roller. This may cause anomalies or defects to occur in the web when the web does come in contact with the roller. In any case, slip area 183B displays a roll identifier column 194 and a priority column 196. Roll identifier column 194 displays information that identifies the relevant roller. Priority column 196 indicates the priority, such as, the severity, of the roll slippage. Again, in other embodiments, other types of priorities could be used, such as color-coded priorities or numeric priorities.

In one embodiment, analysis computer 59 may automatically sort the data displayed in data output area 182 based on priority, from highest priority to lowest, based on the values in priority columns 188 and 196. In one embodiment, analysis computer 59 may automatically populate the user interface, that is, without the need for a user to "refresh" the data. In one embodiment, data output area 182 may display between 0 and 20 entries. In one embodiment, data output area 182 may include a scroll bar, tabs, or other means by which to display a large number of entries.

Figure 13:
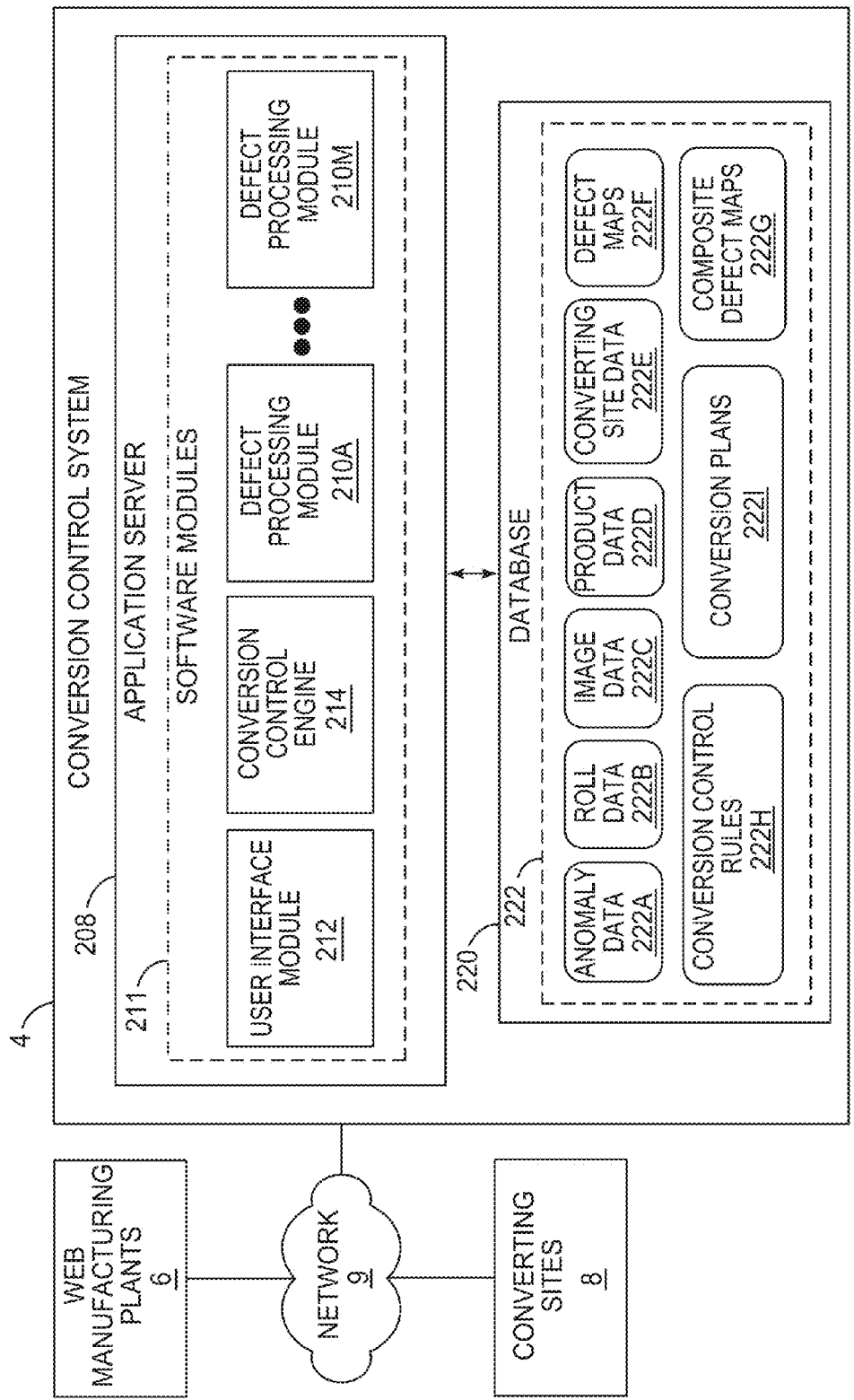
FIG. 13 is a block diagram illustrating an example embodiment of a conversion control system.

FIG. 13 is a block diagram illustrating an example embodiment of conversion control system 4 in further detail. In the example embodiment, application server 208 provides an operating environment for software modules 211. Software modules include a plurality of defect processing modules 210A-210M (application-specific defect detection recipes), a user interface module 212 and a conversion control engine 214.

Software modules 211 interact with database 220 to access data 222, which may include anomaly data 222A, roll data 222B, image data 222C, product data 222D, converting site data 222E, defect maps 222F, composite defect maps 222G, conversion control rules 222H, and conversion plans 222I.

Database 220 may be implemented in any of a number of different forms including a data storage file or one or more database management systems (DBMS) executing on one or more database servers. As one example, database 220 is implemented as a relational database provided by SQL Server™ from Microsoft Corporation.

Anomaly data 222A, roll data 222B, and image data 222C represent the roll information, anomaly information and respective anomaly images received from web manufacturing plants 6 (FIG. 1). Product data 222D represents data associated with products 12 (FIG. 1). More specifically, product data 222D defines each type of product 12 producible by each converting site 8. For each product 12, product data 222D specifies one or more defect processing modules 60 that are required to determine whether a given web roll 10 satisfies the quality requirements for the particular product. In other words, product data 222D specifies one or more defect processing modules 60 that are to be used to analyze anomaly data 222A and image data 222C for each product 12.

In addition, product data 222D stores other information related to products 12 that may be utilized by conversion control system 4 when selecting converting sites 8 and generating conversions plans for web rolls 10. For example, product data 222D may further include data specifying an estimated revenue per unit for each of products 12. Product data 222D may also include data specifying an estimated income per unit for each of products 12, an estimated conversion time to convert a web roll to each product, a current level of industry demand for each of product or other data that may be useful in selecting conversion plans.

Converting site data 222E represents data associated with converting sites 8. For example, converting site data 222E may stores site location, number of process lines and a current available capacity of each process line for each of converting sites 8. Converting site data 222E may store other data, including but not limited to, data specifying a current level of inventory for each product 12 at each converting site 8, shipments costs associated with shipping a web roll to each converting site, shipment options available for each converting site, current order information from customers 14 received by each converting site, data specifying new or preferred customers for each converting site, and other data that may be useful in selecting conversion plans.

As described in further detail below, conversion control engine 214 selects and applies one or more defect processing modules 60 to output defect maps 222F that specify which anomalies are considered actual defects for the different products 12. In other words, each defect map 72F corresponds to a particular web roll 10 and a specific product 12. Each defect map 72F specifies the particular defect locations of a particular web roll 10 based on the product-specific requirements of the corresponding product 12. In some cases, a defect map 72F may represent the aggregate defects determined by a plurality of defect processing modules 60 when generating a series of intermediate defect maps. For example, a defect map 72F may represent a union of the anomalies classified as defects by the two or more defect processing modules 60. Similarly, other operations may be defined such as an intersection of anomalies classified as defects by multiple recipes, or removal from the aggregate defects those defects identified by a particular recipe.

Moreover, when generating a particular defect map 72F, conversion control engine 214 may be configured to select and apply different defect processing modules 60 to those anomalies identified as repeating and those anomalies identified as random. For example, the techniques recognize that it may be advantageous to apply different thresholds or criteria to repeating anomalies as opposed to non-repeating or random anomalies in the same web, and the different thresholds or criteria may be implemented as different defect processing modules 60, i.e., recipes. In other words, when determining which anomalies in a web qualify as defects for a given potential product, conversion control engine 214 may apply a first set of one or more defect processing modules 60 to the repeating anomalies and a second set of defect processing modules 60 to random anomalies. The defect detection recipes of the sets may differ in terms of algorithm and anomaly characteristics considered or may consider the same anomaly characteristics and differ only in terms of sensitivity.

Conversion control engine 64 analyzes the generated defect maps 222F in accordance with conversion control rules 222H to select the ultimate conversion used for each of the web rolls 10. For example, conversion control engine 64 may analyze defect maps 222F to determine which of products 12 would allow a particular web roll 10 to achieve a maximum yield (i.e., utilization) of the web. Conversion control rules 222H specify one or more parameters for consideration by conversion control engine 64 when processing defect maps 222F, such as usage of web material, the number of units that would be produced by each of web rolls 10 for the different products 12, an estimated amount of revenue or profit that would be produced by the web roll for each potential product 12, a process time that would be required to convert the web for each of the different products, a current machine capacity for each process line within converting sites 10, current levels of demand for each of products 12 and other parameters.

During this process, conversion control engine 64 may determine that a particular web roll 10 may be best utilized (e.g., may achieve maximum yield) if converted into multiple products 12. In other words, conversion control engine 64 may determine that a first portion of the web may be best utilized when converted to a first product, and a second portion for a different product. In this case, conversion control engine 64 generates a "composite" defect map 72G that specifies the defect locations within each portion of the web based on the corresponding product to which the portion is to be converted. Conversion control engine 64 may create the composite defect maps by splicing portions of two or more defect maps 222F to form a complete, composite defect map for the entire web.

Upon selecting a particular product or set of products for a given web roll 10, conversion control engine 214 generates a respective conversion plan 72I. Each conversion plan 72I provides precise instructions for processing the respective web roll. More specifically, each conversion plan 222I defines configurations for processing lanes to physically slice the web into individual product sheets. Conversion control system 4 outputs shipment instructions directing the shipment of each web roll 10 to a respective destination converting site 8. Further, conversion control system 4 communicates conversion plans via network 9 to the appropriate converting sites 8 for use in converting the web rolls into the selected products.

User interface module 212 provides an interface by which a user can configure the parameters used by conversion control engine 214 and view defect maps 72F, 72G. For example, as illustrated below, user interface module 212 allows the user to direct conversion control engine 214 to consider one or more of a maximum web utilization, number of units produced, estimated revenue, estimated profit, machine capacity, current levels of demand and/or other parameters. Moreover, by interacting with user interface module 212, the user may specify which combination of one or more defect processing modules 60 are to be applied when generating a defect map 72F as well as the operations, e.g., union, intersection, addition, subtraction, are to be applied when combining the intermediate defect maps produced by the recipes. Further, user interface 212 allows the operator to view the estimated web utilization, number of units produced, estimated revenue, estimated profit, machine capacity, current levels of demand and/or other parameters that would be achieved based on the specified combination of recipes. In this way, the user may elect to reconfigure tune the recipes to achieve desired results and maintain customer satisfaction.

Figure 14:
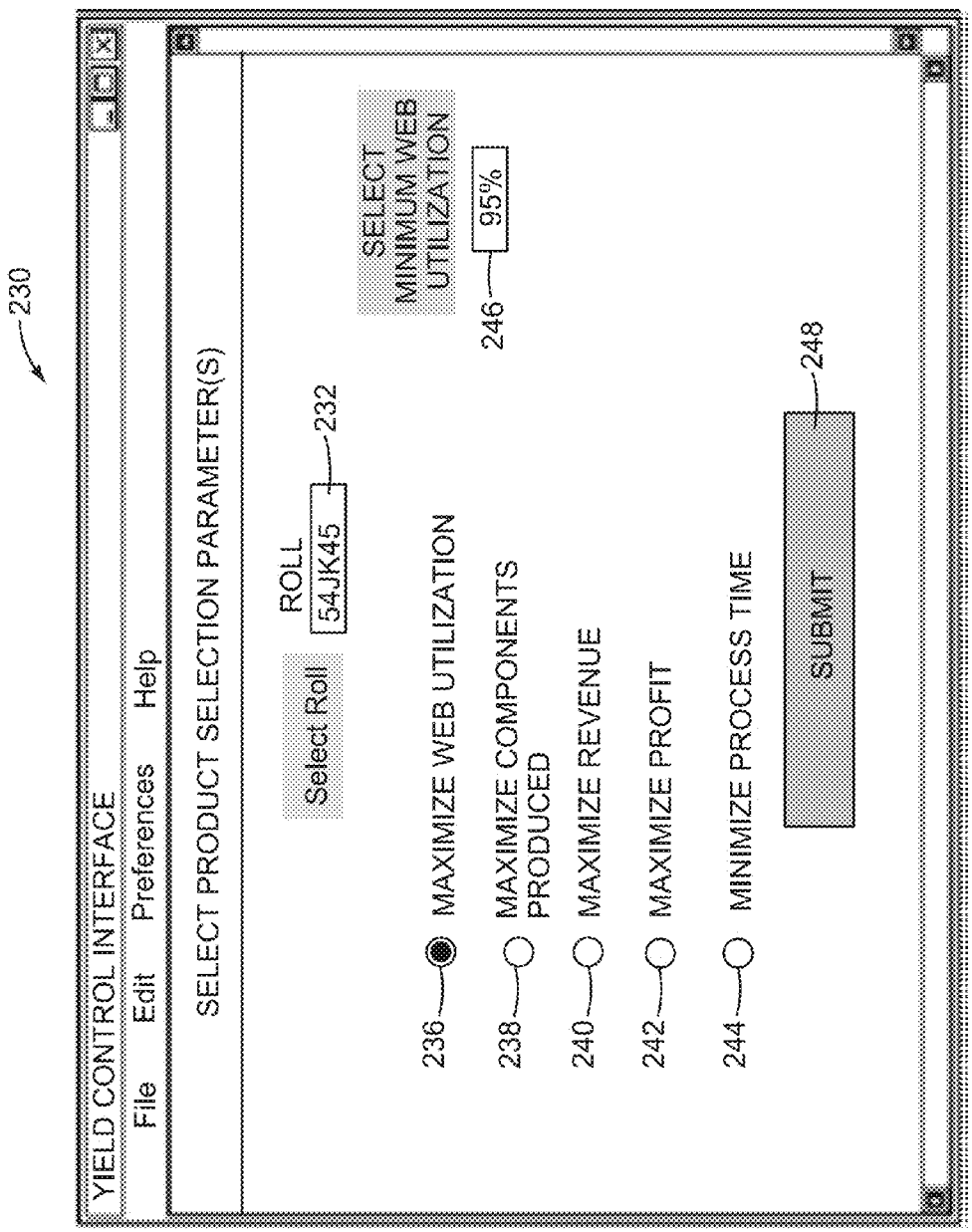
FIG. 14 is an example user interface presented by a user interface module with which a user interacts to configure the conversion control system.

FIG. 14 is an example interface module 230 presented by user interface module 212 with which a user interacts to configure conversion control engine 214. Exemplary interface 230 includes input mechanism 232 by which the user enters a unique identifier for a web roll. Other mechanisms for selecting a roll may be used, such as a drop-down menu, search function, selectable list of recently manufactured rolls or the like.

In addition, interface module 230 provides a plurality of input mechanisms 236-244 by which the user can select one or more product selection parameters for consideration by conversion control engine 214 when generating a recommended conversion plan. In this example, interface module 230 includes a first input selection mechanism 236 to direct conversion control engine 214 to select a conversion plan that seeks to optimize the web utilization for the selected web roll. Input mechanism 238 directs conversion control engine 214 to maximize the number of components produced from selected web roll. Similarly, input mechanisms 240, 242 direct conversion control engine 214 to maximize the revenue and profit generated from selected web roll, respectfully. Input mechanism 244 directs conversion control engine 214 to select a conversion plan that minimizes the process time for selected web roll. Upon selection of one or more parameters, the user selects SUBMIT button 248, which directs conversion control system 4 to process the selected web roll with defect processing modules 210, followed by analysis and conversion plan selection by conversion control engine 214.

In this manner, interface module 230 provides a simplistic illustration of how a user may configure conversion control engine 214 based on one or more parameters. Interface module 230 may require the user to select one and only one of the input mechanisms 236-244. In certain embodiments, interface module 230 includes an input mechanism 96 that allows the user to define a minimum web utilization. This may be advantageous in situations where the user selects a primary parameter, such as profit, to be maximized, but desires a baseline utilization to be met.

Figure 15:
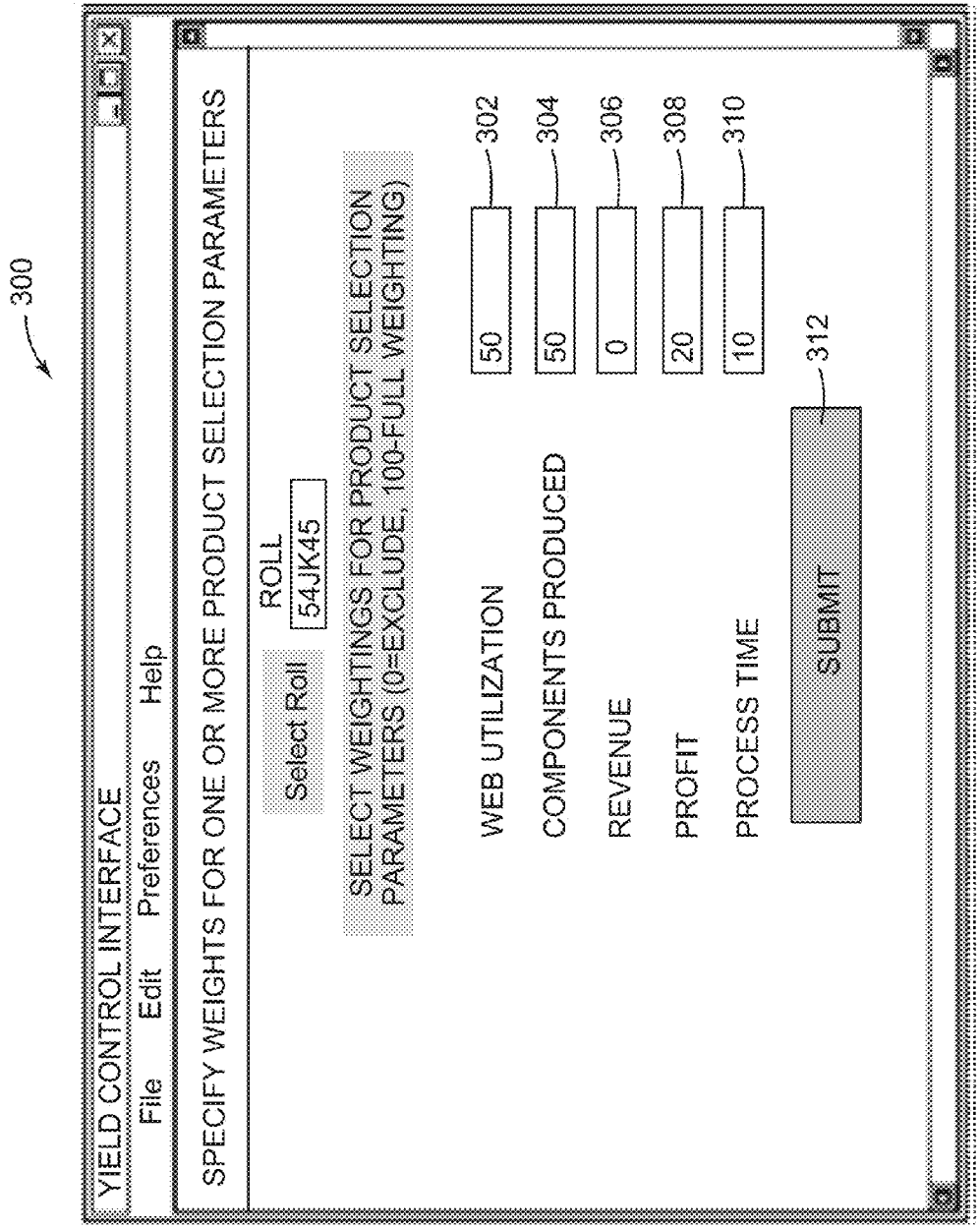
FIG. 15 provides another exemplary user interface presented by the user interface module.

FIG. 15 provides another exemplary user interface 300 presented by user interface module 212. In this embodiment, exemplary interface 300 includes input mechanisms 302-310 by which the user enters respective weighting functions for each parameter. Specifically, input mechanism 302 allows the user to enter a weighting function ranging from 0 to 100 for each parameter, where 0 directs conversion control engine 214 to exclude the parameter and 100 represents the highest possible weighting.

Defect processing modules 210 analyze the anomaly data for the selected web roll when the user selects SUBMIT button 312, followed by analysis and conversion plan selection by conversion control engine 214.

When selecting a conversion plan for a given web roll 10, conversion control engine 214 may analyze defect maps 222F for each potential product 12 for each of the parameters having non-zero weightings. In the example of FIG. 6, conversion control engine 214 analyzes the defect maps 222F and product data 222D to compute web utilization, number of components produced, profit generated and process time for each potential product. As described in further detail below, conversion control engine 214 may then normalize the computed results of each parameter for each product, and then compute weighted values from the normalized results. Finally, conversion control engine 214 selects a conversion plan as a function of (e.g., a sum) of the weighted values. Other technique may be utilized in which conversion control system 4 utilizes multiple parameters when selecting a conversion plan for a web roll 10.

Figure 16:
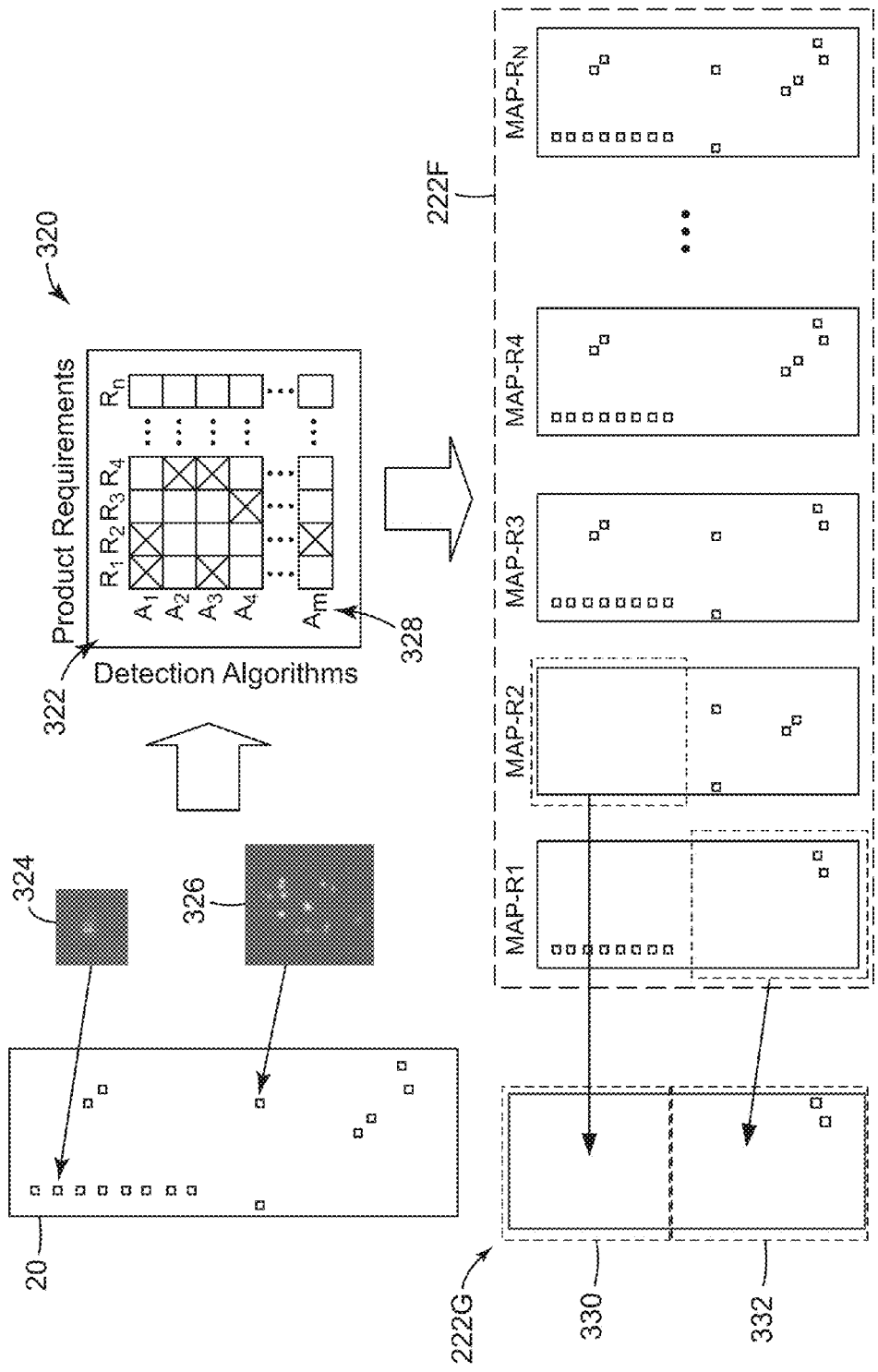
FIG. 16 is a flow diagram that illustrates exemplary processing of anomaly information by the conversion control system.

FIG. 16 is a flow diagram that illustrates the processing of anomaly information by conversion control system 4 in further detail. In particular, FIG. 16 illustrates the processing of anomaly data 222A and image data 222C by defect processing modules 210.

Conversion control system 4 receives the image and anomaly data, such as images 324, 326, that were extracted initially from a web 20 by an analysis computer 28 located at a web manufacturing plant 6 using a simple first detection algorithm.

As illustrated in FIG. 16, defect processing modules 210 apply "M" different algorithms (designated $A_1$-$A_m$ 328 in FIG. 7) as needed for up to N different requirements 320 for products 12. Cross-reference table 322 is used to illustrate the mapping between requirements 320 and defect processing modules 210. Specifically, cross-reference table 322 shows which defect processing modules 210 are utilized in determining whether each anomaly is a defect or a false positive for a given requirement 320.

In some embodiments, a larger number of rather simpler algorithms are conveniently used in parallel. For example, it is often convenient that at least one of the subsequent defect processing modules 210 apply an algorithm that includes comparing each anomaly against a combination threshold-pixel size criterion. In actual practice with, for example, optical films, an anomaly having only a subtle difference in brightness value from a target is unacceptable if the area is large, and an anomaly having a great difference in brightness from a target value is unacceptable even if the area is very small. Moreover, the threshold-pixel size criterion may be tuned to be different for repeat anomalies versus random anomalies. For example, a relatively higher combination threshold-pixel size criterion may be required to qualify as a defect for a random anomaly versus an anomaly that has been determined to be one of a set of repeated anomalies. As such, the recipe for repeat anomalies may define a lower pixel size-brightness threshold combination required to qualify as a defect when compared to a recipe that considers only random anomalies.

In addition, the algorithms applied by defect processing modules 210 can incorporate very complex image processing and defect extraction including, but not limited to, neighborhood averaging, neighborhood ranking, contrast expansion, various monadic and dyadic image manipulations, digital filtering such as Laplacian filters, Sobel operators, high-pass filtering and low-pass filtering, texture analysis, fractal analysis, frequency processing such as Fourier transforms and wavelet transforms, convolutions, morphological processing, thresholding, connected component analyses, blob processing, blob classifications, or combinations thereof. Other algorithms may be applied based on the specific web and defect types to achieve a desired accuracy level of defect detection.

Each of the N product requirements 320 can be accomplished using selected combinations of individual defect processing algorithms 328, also referred to herein as recipes. The algorithms may use very simple threshold and minimum blob processing or more complex algorithms such as spatial filters, morphological operations, frequency filters, wavelet processing, or any other known image processing algorithms. In this exemplary cross-reference table 322, product requirement $R_1$ uses a combination of algorithms $A_2$, $A_4$, and $A_M$, each applied to every anomaly image to determine which anomalies are actual defects for $R_1$. In most convenient embodiments, a simple OR logic is employed, i.e. if any of $A_2$, $A_4$, and $A_M$ report the anomaly as an actual defect, that portion of web 20 does not satisfy product requirement $R_1$. For specialized applications, the logic through which the reports of the subsequent algorithms 328 are combined into a determination of whether a product requirement 320 is satisfied may be more complex than a simple OR logic. Similarly, product requirement $R_2$ uses $A_2$, $A_3$, and $A_4$, etc. Thus, the anomalies that are identified as defects for $R_2$ may be similar to or significantly different than defects for $R_1$.

As discussed above, individual defect processing algorithms 328 may be customized to analyze repeating anomalies or random anomalies. For example, a set of defect processing algorithms 328 may be configured to produce a resultant set of defects using only anomalies that are considered repeating anomalies as an input set to the algorithms. Similarly, another set of defect processing algorithms may be configured to produce a result set of defects using only anomalies that are considered to be random as an input set to the algorithms. In this way, specific levels and thresholds of the criteria, such as anomaly brightness, area, length, width, and other characteristics, analyzed by the defect detection algorithms may be tailored based on whether the anomalies are repeat anomalies or random anomalies.

After determining which anomalies are considered actual defects by using cross-reference table 322, conversion control engine 214 formulates defect maps 222F of actual defect locations corresponding to the various product requirements for the roll. In some situations, conversion control engine 214 may generate one or more composite defect maps 222G by splicing one or more portions of defect maps 222F. In this illustrated example, conversion control engine 214 generates a composite map 222G having a first portion 330 spliced from a defect map for a first product requirement (MAP-R1) and a second portion 332 from a defect map for a second product requirement (MAP-R2). In this manner, conversion control engine 214 may determine that a web may be best utilized if certain portions of the web are converted into different products. Once this has been done, it is often possible to discard the subimage information to minimize the needed storage media.

Further details of image processing and subsequent application of the anomaly detection algorithms applied by defect processing modules 210 are described by commonly assigned and co-pending Ser. No. 10/669,197 (now U.S. Pat. No. 7,027,934 B2), entitled "APPARATUS AND METHOD FOR AUTOMATED WEB INSPECTION," filed Apr. 24, 2003, the entire contents of which are incorporated herein by reference.

FIGS. 17-24 are flowcharts illustrating various exemplary embodiments in which conversion control engine 214 applies conversion rules 222H to generate conversion plans 222I based on one or more user-configurable parameters, such as usage of web material, number of units produced, revenue, profit, process time, machine capacity, product demand and other parameters.

Figure 17:
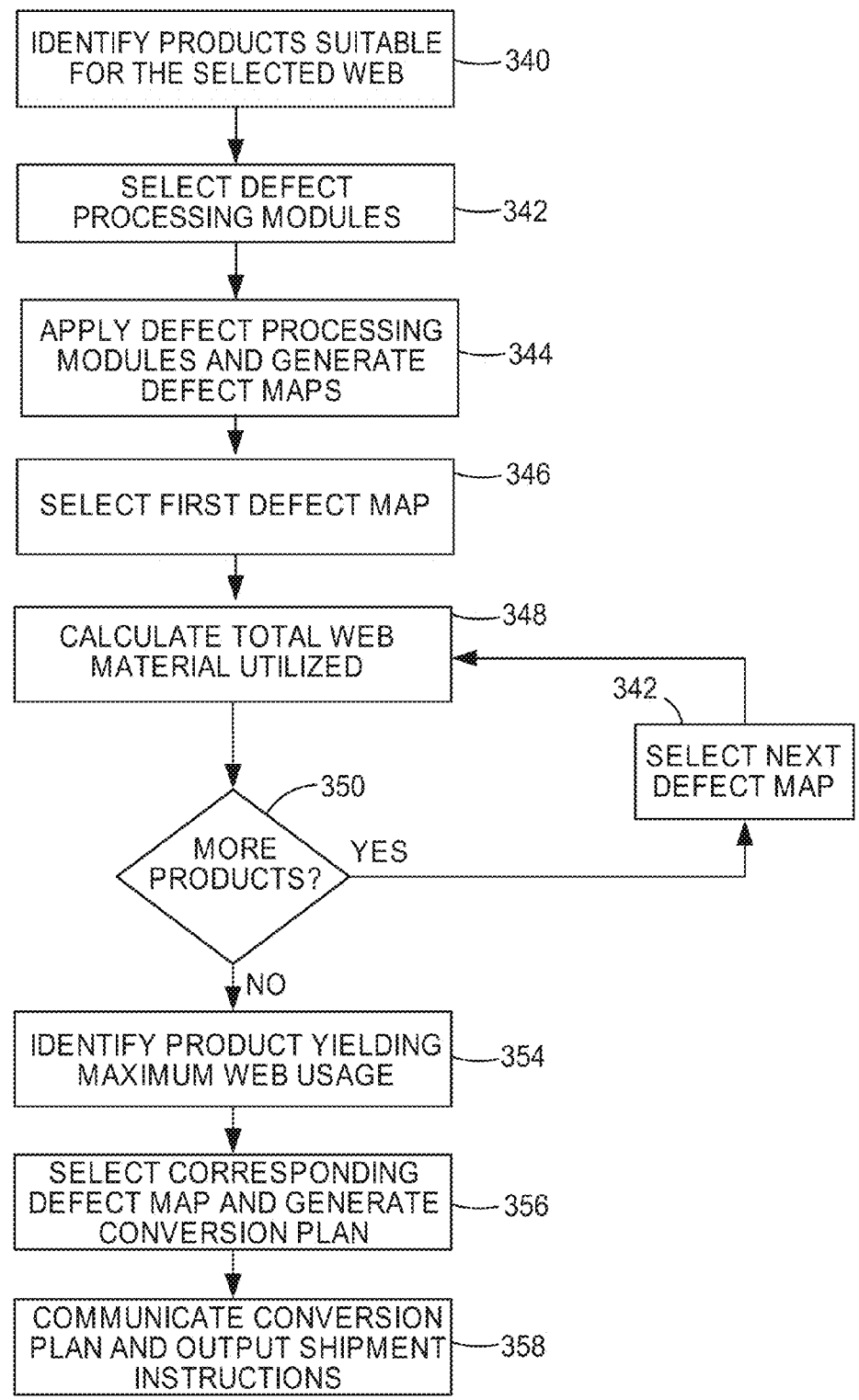
FIG. 17 is a flowchart illustrating one exemplary method in which a conversion control engine generates a conversion plan for a given web roll to maximize web utilization.

FIG. 17 is a flowchart illustrating one exemplary method in which conversion control engine 214 selects a conversion plan 222I for a given web roll 10 to maximize web utilization. Initially, conversion control engine 214 identifies a set of potential products 12 into which the web roll 10 may be converted (340). As described above, if the web roll has been or is currently being shipped to a particular converting site 8, conversion control engine 214 selects one or more of the products associated with the specific converting site for which the web roll is suitable. Alternatively, if the web roll being considered has not been shipped, conversion control system 4 may select all of products 12 for which the web roll is suitable.

Conversion control engine 214 accesses product data 222D of database 222 to identify the product requirements for the identified set of suitable products, and selects one or more of the defect processing modules 210 based on the identified requirements (342). As discussed above, at this time conversion control engine 214 may multiple application-specific defect detection recipes, including a first set of recipes for repeating anomalies and a second set of different recipes for random anomalies within anomaly data 222A for the given web roll 10.

Next, conversion control engine 214 invokes the selected defect processing modules 210, which apply respective defect detection algorithms to anomaly data 222A and image data 222C received from a web manufacturing plant 6 to formulate defect information for each of the product requirements. Conversion control engine 214 generates defect maps 222F based on the defects identified by defect processing modules 210 (344).

In the example of FIG. 17, conversion control engine 214 selects a first one of the defect maps (346), and analyzes the map to calculate a yield for the web, either in percentage of material utilized, actual area utilized or some other convenient metric (348). Conversion control engine 214 repeats this process for each defect map (350, 352).

Conversion control engine 214 then selects the product that would result in the maximum yield for the web roll (354). Conversion control engine 214 identifies the defect map associated with the selected product, and outputs a recommended conversion plan 222I in accordance with the selected defect map for review by the operator (356). In this way, conversion control engine 214 may process a plurality of defect maps, including aggregate defect maps generated using defect detection recipes having different sensitivity to repeating defects and non-repeating defects, when selecting the product that would result in the maximum yield, potentially without potentially sacrificing customer satisfaction. For example, in some situations, a more stringent recipe for classifying repeat anomalies as defects may be preferred as a customer may be more sensitive to repeat defects in the final product. In this case, application of a more stringent application-specific defect detection recipe applied only to the repeating anomalies may result in an improved level of customer satisfaction. The process allows an operator to select and modify the sensitivity of the different sets of application defect detection recipes so as to achieve substantially the same level of customer satisfaction yet realize an increase in conversion yield for the web. For example, a less stringent recipe applied only to random (non-repeating) anomalies utilized in combination with a recipe applied only to repeating defect with an unchanged, or only a moderately increased sensitivity, may ultimately achieve an increased conversion yield, as shown by conversion control engine 214, yet maintain substantially the same level of customer satisfaction as would be otherwise achieved without differentiating between repeating and non-repeating anomalies. Example differences in sensitivity include a 5% relative difference, a 10% relative difference, a 20% relative difference and a 30% relative difference in, for example, a pixel size, brightness or other characteristic for repeat and random anomalies.

Conversion control engine 214 may further communicate the conversion plan to the appropriate converting site 8, and output (e.g., display or print) shipment instructions for shipping the particular web roll 10 to the converting site (358).

Figure 18:
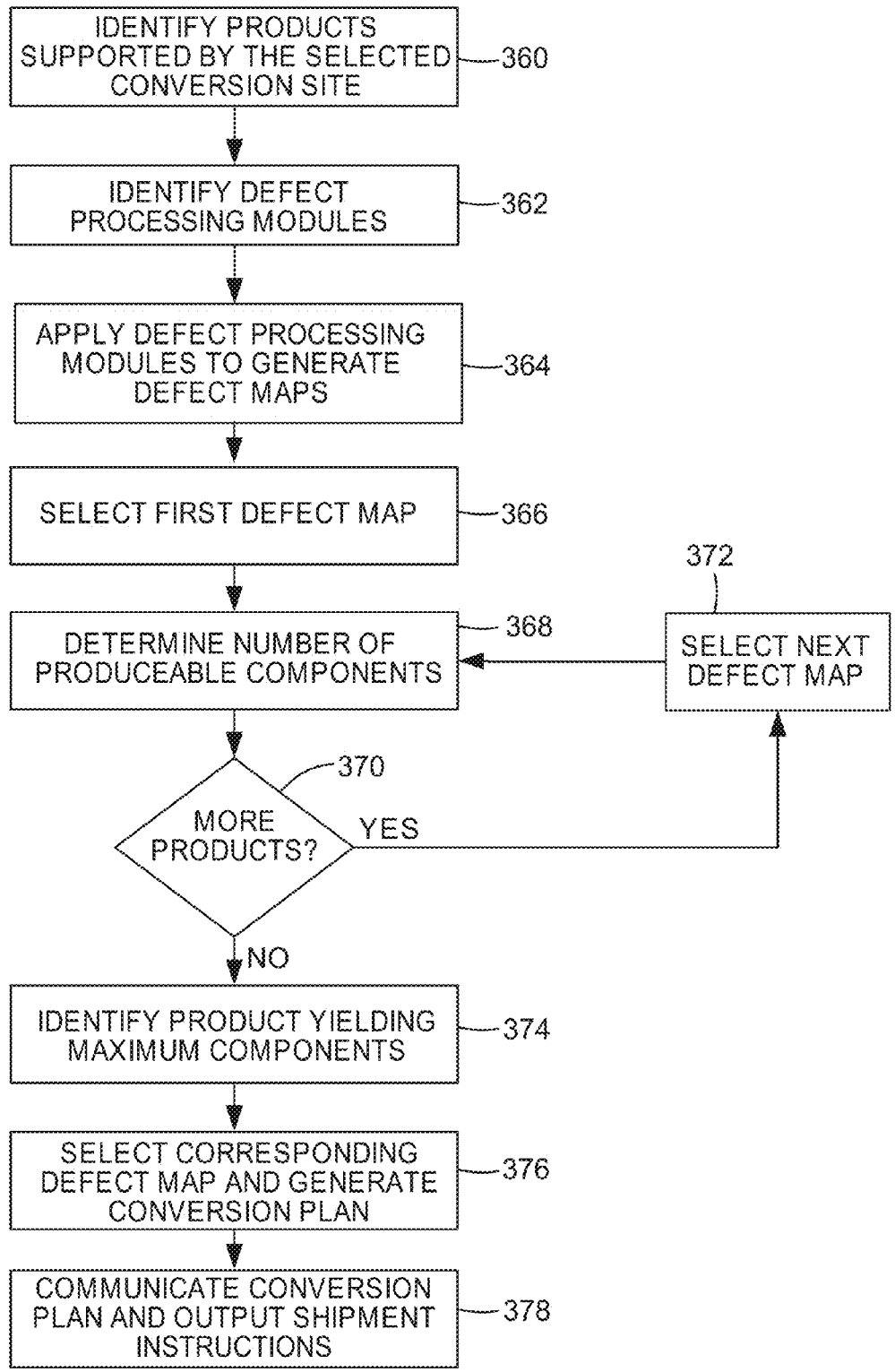
FIG. 18 is a flowchart illustrating an exemplary method in which the conversion control engine generates a conversion plan to maximize the number of components produced from the web roll.

FIG. 18 is a flowchart illustrating an exemplary method in which conversion control engine 214 generates a conversion plan 222I for a given web roll 10 to maximize the number of components produced from the web roll. As described above, conversion control engine 214 identifies a set of potential products 12 into which the web roll 10 may be converted, and selectively invokes one or more of the defect processing modules 210 to apply defect detection algorithms and generates defect maps 222F for the web roll (360-364).

In the example method of FIG. 18, conversion control engine 214 selects a first one of the defect maps (366), and analyzes the map to calculate a total number of components that could be produced for the respective product (368). Conversion control engine 214 repeats this process for each defect map (370, 372).

Conversion control engine 214 then selects the product that would result in the maximum number of components produced by the web roll (374). For example, based on the specific locations of the defects, few components may be realizable for a larger sized product (e.g., a film for a computer screen) versus a smaller sized product (e.g., a film for a mobile phone display).

Conversion control engine 214 generates a conversion plan 222I based on the selected product, communicates the conversion plan to the appropriate converting site 8, and outputs (e.g., display or print) shipment instructions for shipping the particular web roll 10 to the converting site (376-378).

Figure 19:
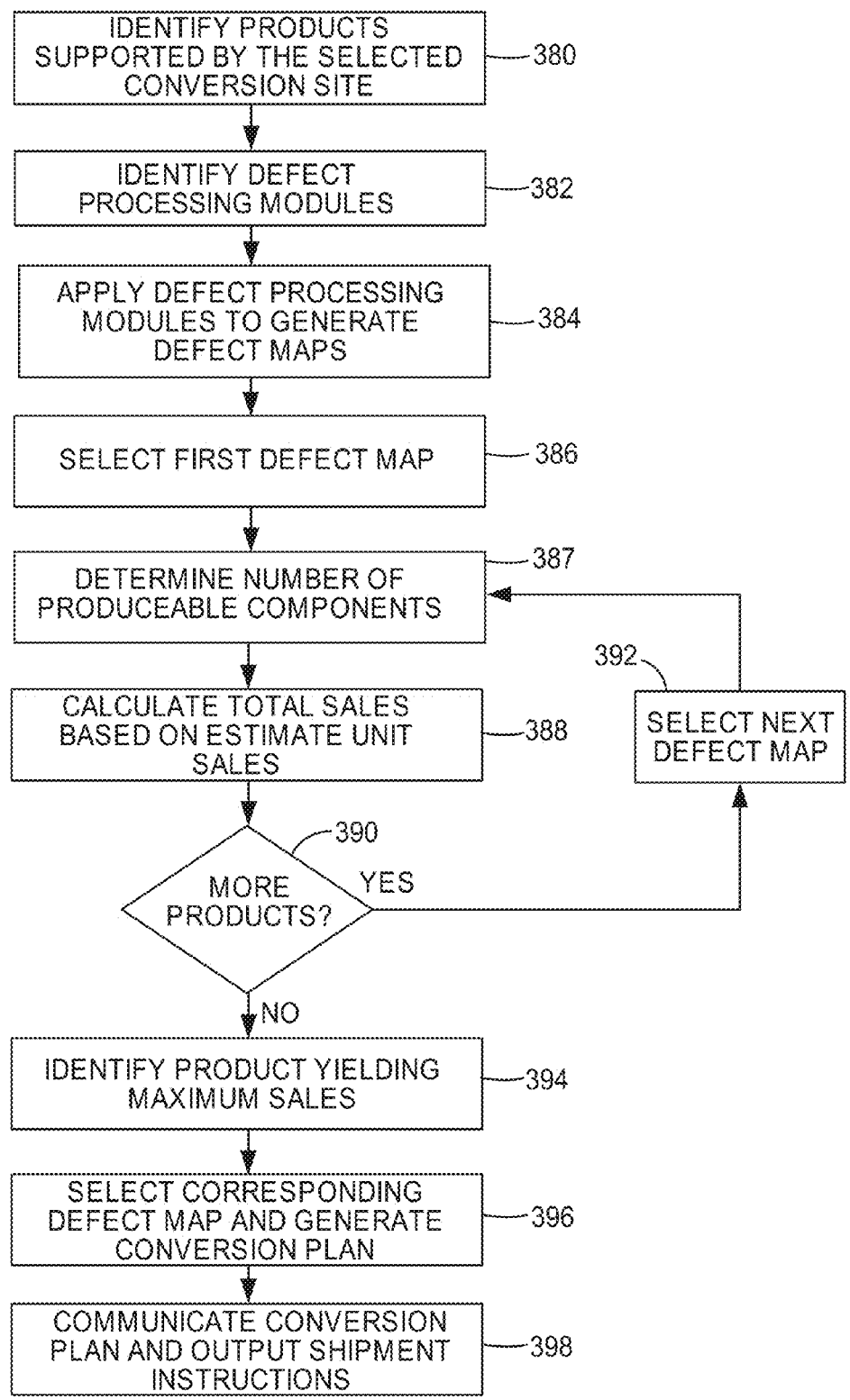
FIG. 19 is a flowchart illustrating an exemplary method in which the conversion control engine generates a conversion plan for a given web roll to maximize a total unit sales volume realized from the web roll.

FIG. 19 is a flowchart illustrating an exemplary method in which conversion control engine 214 generates a conversion plan 222I for a given web roll 10 to maximize a total unit sales volume realized from the web roll. As described above, conversion control engine 214 identifies a set of potential products 12 into which the web roll 10 may be converted, and selectively invokes one or more of the defect processing modules 210 to apply defect detection algorithms and generates defect maps 222F for the web roll (380-384).

Next, conversion control engine 214 selects a first one of the defect maps (386), and analyzes the map to calculate a total number of components that could be produced for the respective product (387). Next, conversion control engine 214 accesses product data 222D to retrieve an estimated sale price per unit for the particular product. Based on the estimated sale price, conversion control engine 214 calculates a total estimated sales (e.g., in dollars) that would be generated from the web roll if the web roll were converted into the product (38). Conversion control engine 214 repeats this process for each defect map (390, 392).

Conversion control engine 214 then selects the product that would result in the maximum amount of realized sales, i.e., revenue, for the web roll (394). For example, certain components may better capture a premium price than other components due to market factors. In this exemplary embodiment, conversion control engine 214 may select a product that does not achieve a maximum utilization of the web roll, but nevertheless is expected to generate higher sales relative to the other suitable products.

Conversion control engine 214 generates a conversion plan 222I based on the selected product, communicates the conversion plan to the appropriate converting site 8, and outputs (e.g., display or print) shipment instructions for shipping the particular web roll 10 to the converting site (396-398).

Figure 20:
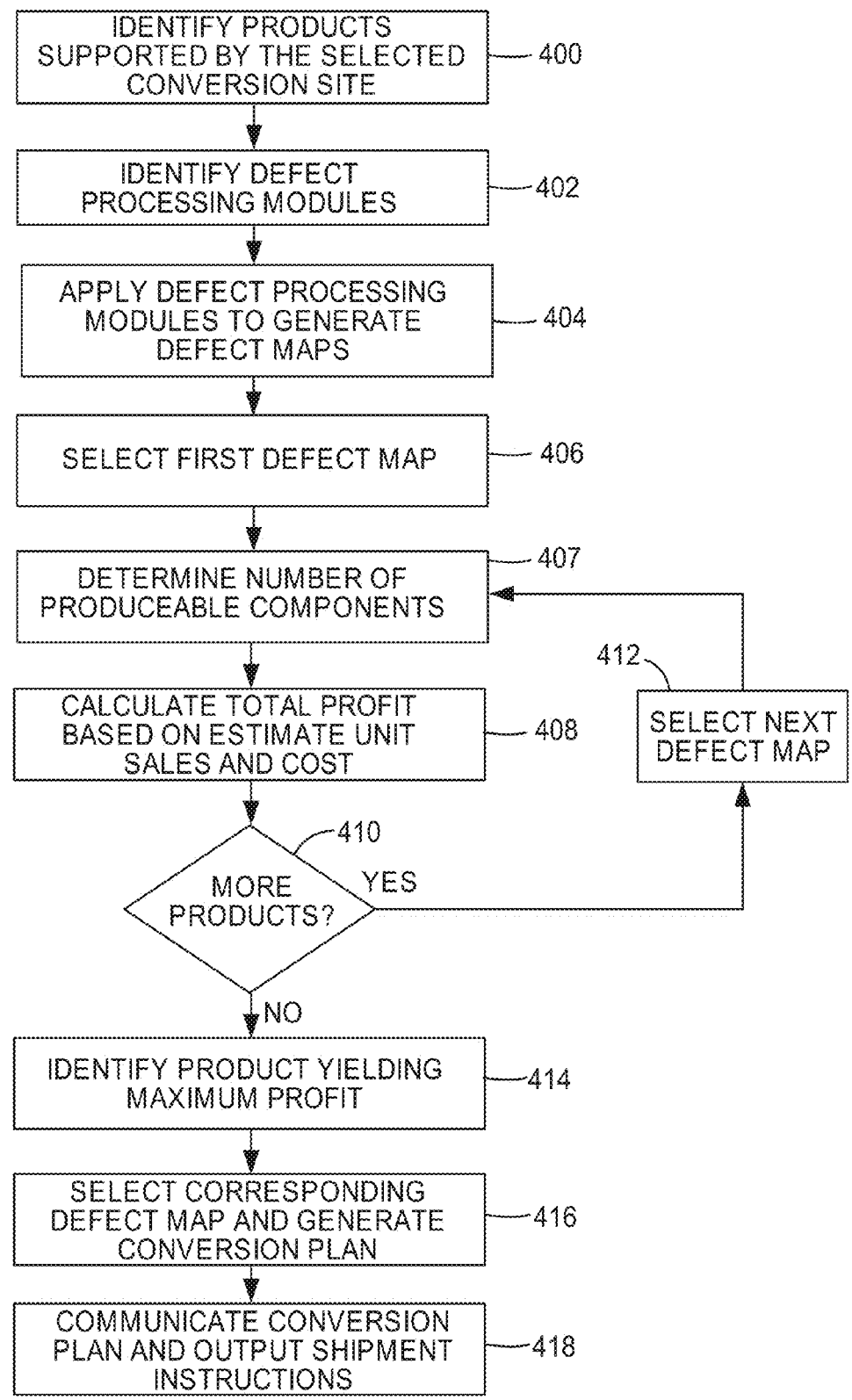
FIG. 20 is a flowchart illustrating an exemplary method in which the conversion control engine generates a conversion plan to maximize a total profit realized from the web roll.

FIG. 20 is a flowchart illustrating an exemplary method in which conversion control engine 214 generates a conversion plan 222I for a given web roll 10 to maximize a total profit realized from the web roll. As described above, conversion control engine 214 identifies a set of potential products 12 into which the web roll 10 may be converted, and selectively invokes one or more of the defect processing modules 210 to apply defect detection algorithms and generates defect maps 222F for the web roll (400-404).

Conversion control engine 214 then selects a first one of the defect maps (276), and analyzes the map to calculate a total number of components that could be produced for the respective product (407). Next, conversion control engine 214 accesses product data 222D to retrieve an estimated sales price and estimated cost per unit for the particular product. Based on the estimated sales price and cost, conversion control engine 214 calculates a total estimated profit realized from the web roll if the web roll were converted into the product (408). Conversion control engine 214 repeats this process for each defect map (410, 412).

Conversion control engine 214 then selects the product that would result in the maximum amount of profit realized for the web roll (414). Conversion control engine 214 generates a conversion plan 222I based on the selected product, communicates the conversion plan to the appropriate converting site 8, and outputs (e.g., display or print) shipment instructions for shipping the particular web roll 10 to the converting site (416-418).

Figure 21:
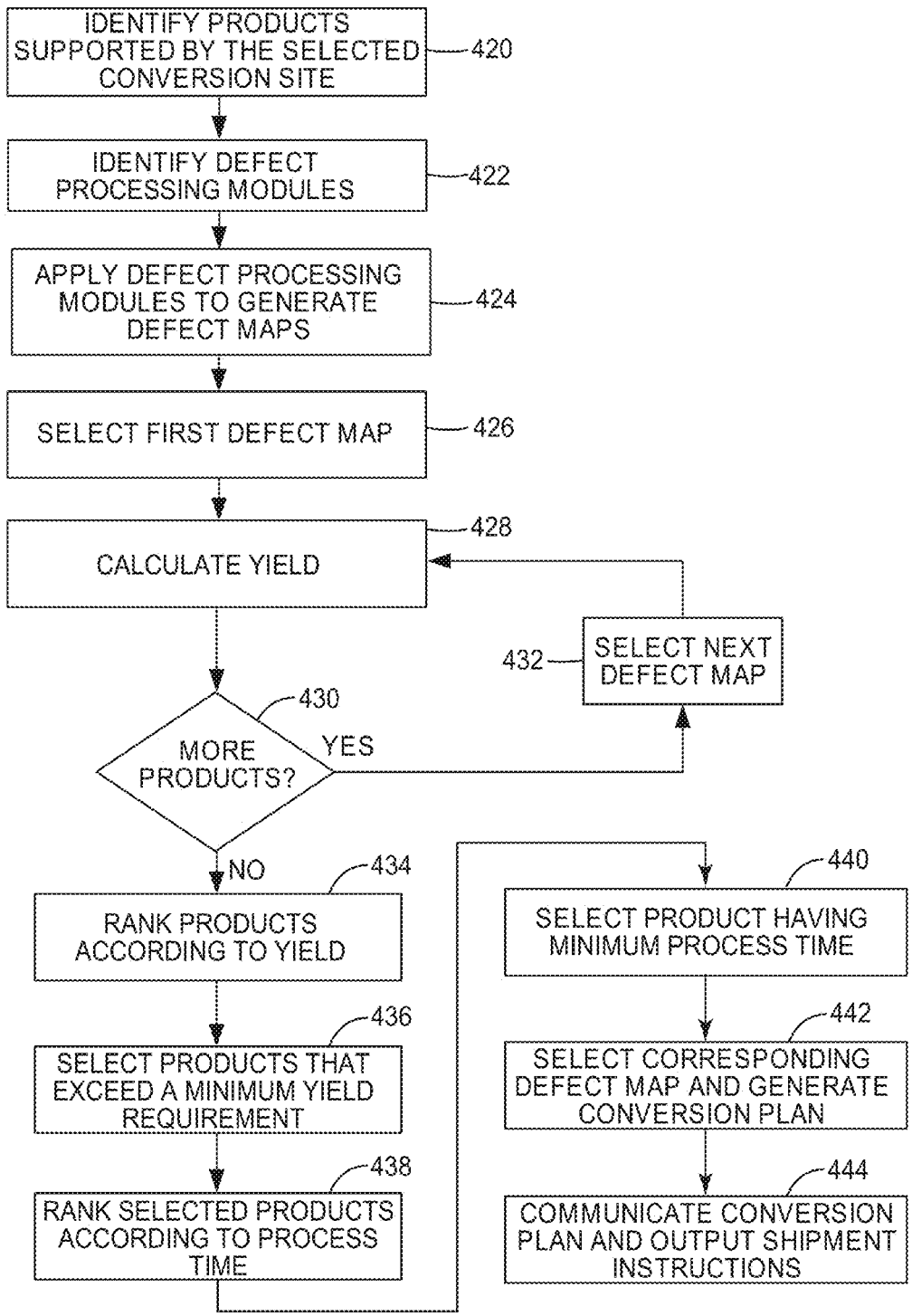
FIG. 21 is a flowchart illustrating an exemplary method in which the conversion control engine generates a conversion plan to minimize process time for a web roll yet achieve a defined minimum yield.

FIG. 21 is a flowchart illustrating an exemplary method in which conversion control engine 214 generates a conversion plan 222I for a given web roll 10 to minimize process time yet achieve a required minimum yield. As described above, conversion control engine 214 identifies a set of potential products 12 into which the web roll 10 may be converted, and selectively invokes one or more of the defect processing modules 210 to apply defect detection algorithms and generates defect maps 222F for the web roll (420-424).

Next, conversion control engine 214 selects a first one of the defect maps (306), and analyzes the map to calculate a yield that would be produced for the respective product, either as a percentage of material utilized, actual area utilized or some other convenient metric (428). Conversion control engine 214 repeats this process for each defect map (430, 432).

Conversion control engine 214 then ranks the products according to the estimated yield (434), and selects a subset of the products including only those products that would achieve a defined minimum yield (436). Next, conversion control engine 214 ranks the subset of products according to a process time, as specified in product data 222D (438). Conversion control engine 214 then selects the product from the subset of products that has the lowest estimated process time (440). Conversion control engine 214 generates a conversion plan 222I based on the selected product, communicates the conversion plan to the appropriate converting site 8, and outputs (e.g., display or print) shipment instructions for shipping the particular web roll 10 to the converting site (442-444). In this manner, conversion control engine 214 defines a conversion plan 222I for web roll 10 to achieve an acceptable yield level while minimizing conversion time (i.e., maximizing throughput) of the web at converting sites 8.

Figure 22:
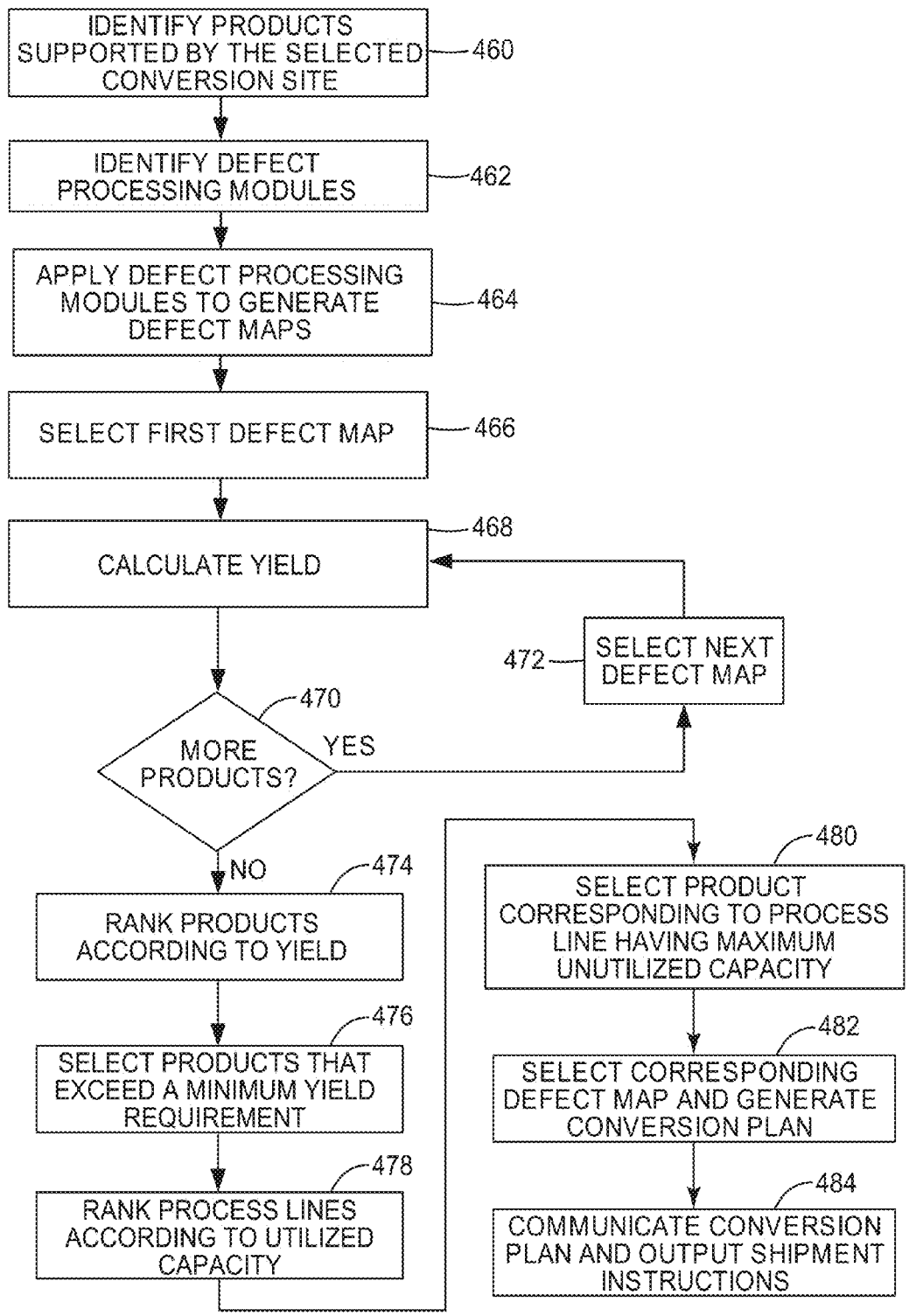
FIG. 22 is a flowchart illustrating an exemplary method in which the conversion control engine generates a conversion plan to maximize utilization of process lines at one or more converting sites, yet achieve a defined minimum yield for the web roll.

FIG. 22 is a flowchart illustrating an exemplary method in which conversion control engine 214 generates a conversion plan 222I for a given web roll 10 to maximize utilization of process lines at converting sites 8, yet achieve a required minimum yield for the web roll. As described above, conversion control engine 214 identifies a set of potential products 12 into which the web roll 10 may be converted, and selectively invokes one or more of the defect processing modules 210 to apply defect detection algorithms and generates defect maps 222F for the web roll (460-464).

Next, conversion control engine 214 selects a first one of the defect maps (346), and analyzes the map to calculate a yield that would be produced for the respective product, either as a percentage of material utilized, actual area utilized or some other convenient metric (468). Conversion control engine 214 repeats this process for each defect map (470, 472).

Conversion control engine 214 then ranks the products according to the estimated yield (474), and selects a subset of the products including only those products that would achieve a defined minimum yield (476). Next, conversion control engine 214 accesses converting site data 222E to determine a set of process lines of converting sites 8 suitable for converting the subset of products. Conversion control engine 214 ranks the identified process lines according to current unutilized capacity (478). Conversion control engine 214 then selects the product from the subset of products that corresponds to the process line having the highest unutilized capacity (480). Conversion control engine 214 generates a conversion plan 222I based on the selected product, communicates the conversion plan to the appropriate converting site 8, and outputs (e.g., display or print) shipment instructions for shipping the particular web roll 10 to the converting site (482-484). In this manner, conversion control engine 214 defines a conversion plan 222I for web roll 10 to achieve an acceptable yield level while maximizing the utilization of the process lines of converting sites 8.

Figure 23:
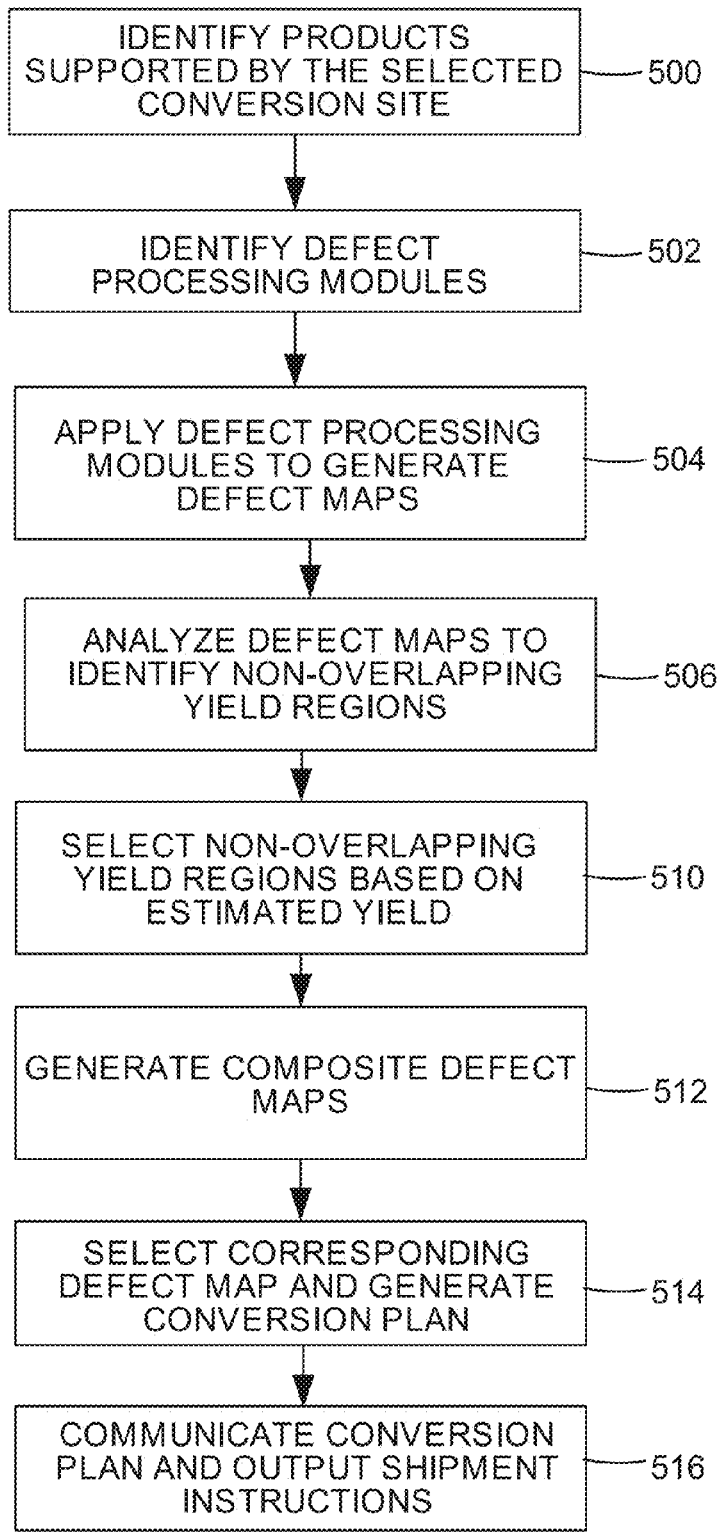
FIG. 23 is a flowchart illustrating an exemplary method in which the conversion control engine generates a conversion plan based on a composite defect map to convert the web roll into two or more products to maximize utilization of the web roll.

FIG. 23 is a flowchart illustrating an exemplary method in which conversion control engine 214 generates a conversion plan 222I for a given web roll 10 based on a composite defect map to convert the web roll into two or more products to maximize utilization of the web roll. As described above, conversion control engine 214 identifies a set of potential products 12 into which the web roll 10 may be converted, and selectively invokes one or more of the defect processing modules 210 to apply defect detection algorithms and generates defect maps 222F for the web roll (500-504).

Next, conversion control engine 214 analyzes the defect maps to define regions of the maps based on yield (506). For example, as illustrated in FIG. 7, based on the analysis, conversion control engine 214 may define a first region of one of the defect maps that would result in a relatively high yield for a first product, and a second non-overlapping region of a different product map that would result in a high yield for a second product.

Conversion control engine 214 ranks and selects the non-overlapping regions based on estimated yield (510), and generates a composite defect map 222G by splicing the non-overlapping regions to form the composite defect map (512). In this manner, conversion control engine 214 may determine that a web may be best utilized if certain portions of the web are converted into different products.

Conversion control engine 214 generates a conversion plan 222I based on the composite defect map, communicates the conversion plan to the appropriate converting site 8, and outputs (e.g., display or print) shipment instructions for shipping the particular web roll 10 to the converting site (514-516). In this manner, conversion control engine 214 defines a conversion plan 222I for web roll 10 to convert the web roll into two or more products to maximize utilization of the web roll.

Figure 24:
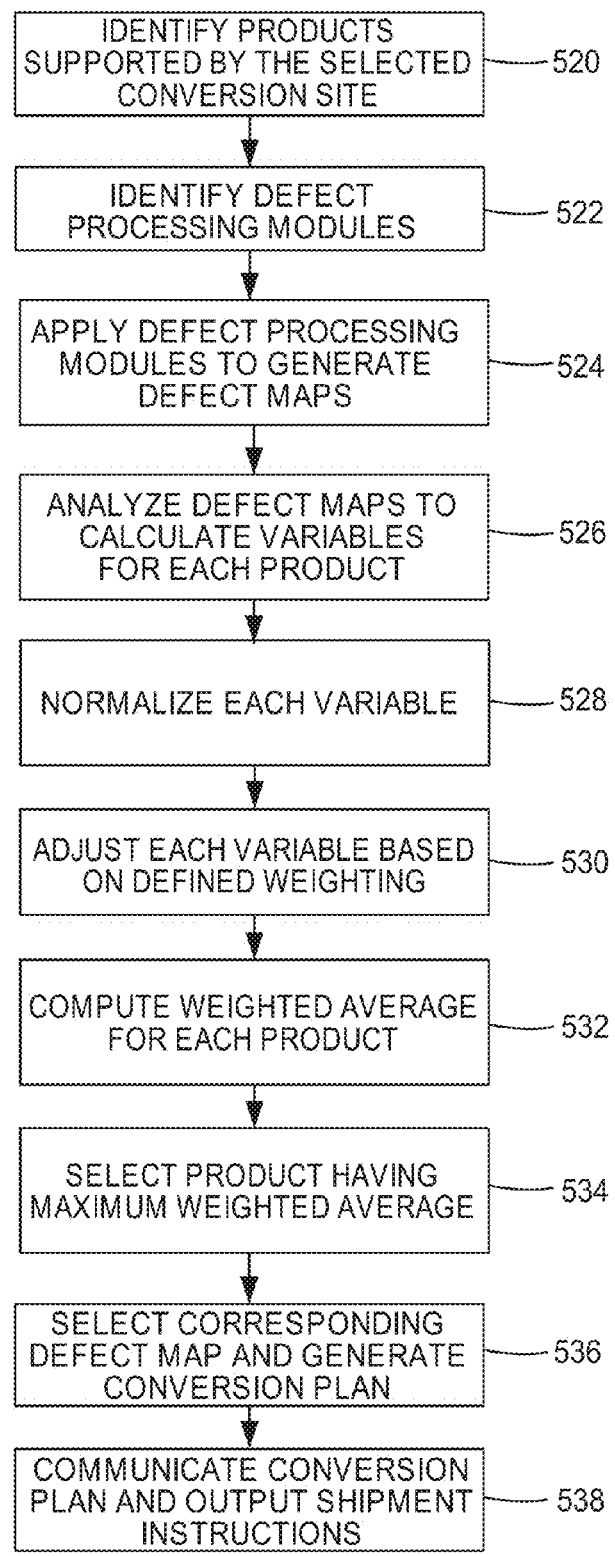
FIG. 24 is a flowchart illustrating an exemplary method in which the conversion control engine generates a conversion plan for a given web roll based on a weighted average of a plurality of configurable parameters.

FIG. 24 is a flowchart illustrating an exemplary method in which conversion control engine 214 generates a conversion plan 222I for a given web roll 10 based on a weighted average of a plurality of configurable parameters. Conversion control engine 214 identifies a set of potential products 12 into which the web roll 10 may be converted, and selectively invokes one or more of the defect processing modules 210 to apply defect detection algorithms and generates defect maps 222F for the web roll (520-524).

Next, conversion control engine 214 employs any of the described techniques to calculate the specified parameters, e.g., web utilization, component yield, profit, sales, process capacity, process time or other parameters for each of the products (526). Conversion control engine 214 then normalizes each of the parameters to a common range, such as 0 to 100 (528).

Conversion control engine 214 then adjusts each of the parameters in accordance with a user-configurable weighting, as shown in FIG. 6 (530), and computes a total weighted average for each product (532). Conversion control engine 214 selects the product corresponding to the maximum weighted average of the parameters (534), generates a conversion plan 222I for the selected product based on the respective defect map (536).

Conversion control engine 214 communicates the conversion plan to the appropriate converting site 8, and outputs (e.g., display or print) shipment instructions for shipping the particular web roll 10 to the converting site (538). In this manner, conversion control engine 214 may consider multiple parameters when defining a conversion plan 222I for converting the web roll into products based on stored image anomaly information.

Figure 25:
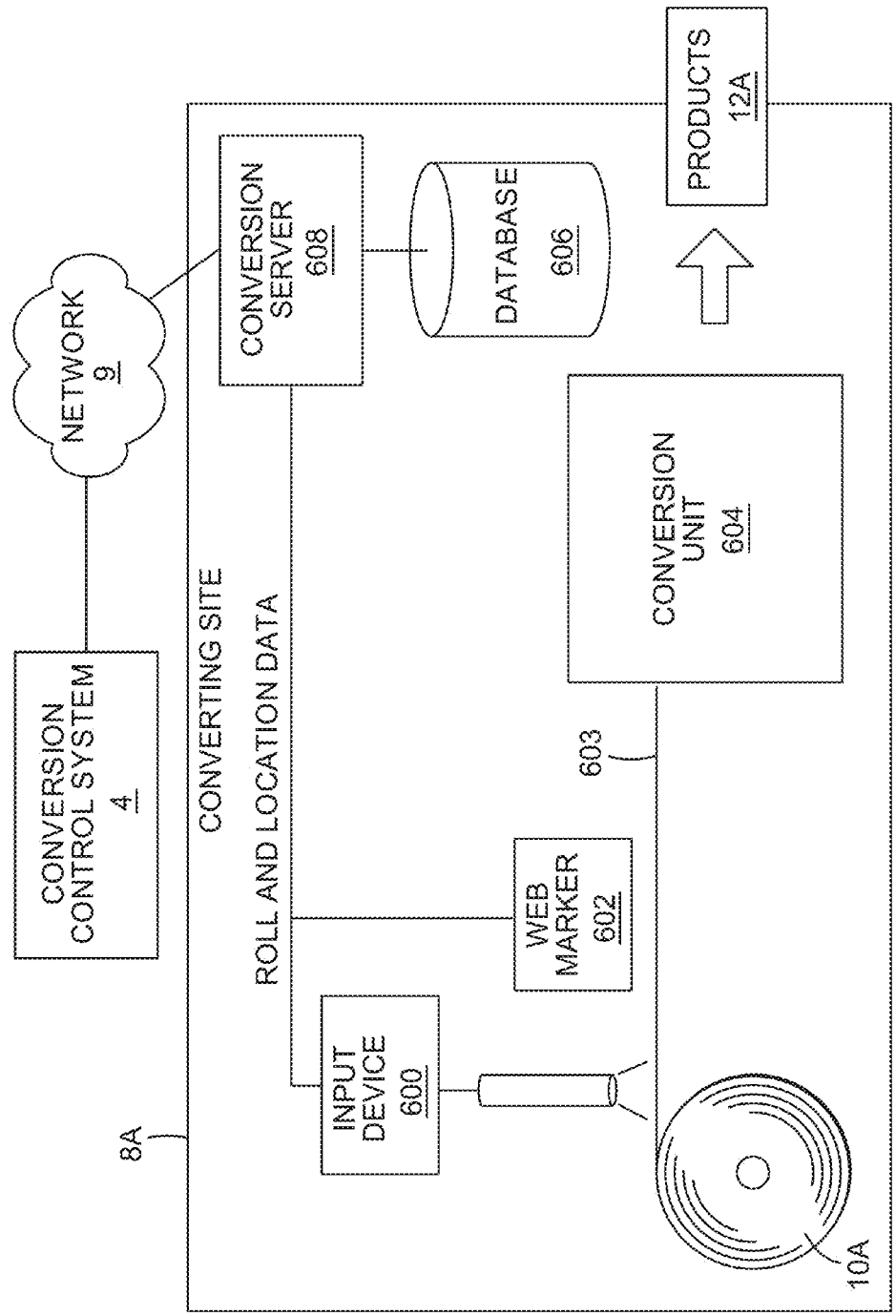
FIG. 25 is a block diagram illustrating one embodiment of a converting site.

FIG. 25 is a block diagram illustrating one embodiment of a converting site 8A. In this exemplary embodiment, converting site 8A includes a web roll 10A that has been loaded and readied for conversion.

Conversion server 608 receives conversion maps from conversion control system 4, and stores the conversion maps in database 606. A barcode is read from roll 10A, which informs conversion server 608 of the particular web 603, allowing the conversion server to access database 606 and retrieve the corresponding conversion map. The barcode may be read by input device 600 when web 603 is placed in motion or via a hand-held barcode device prior to loading.

Conversion server 608 displays a conversion plan, thereby allowing workers to configure conversion unit 604. Specifically, conversion unit 604 is configured to physically cut web 603 into numerous individual sheets (i.e., products 12A) in accordance with the conversion plan.

As web 603 passes through the system during the marking operation, input device 500 reads fiducial marks and associated barcodes are regularly sensed. The combination of barcode and fiducial mark enables one to precisely register the physical position of web 603 to the defects identified in the conversion plan. Regular re-registration ensures ongoing registration accuracy. One skilled in the art is capable of establishing the re-registration through conventional physical coordinate transformation techniques. Once web 603 is registered to the conversion map, the physical position of specific defects is known.

When defects pass under web marker 602, marks are applied to web 603 to visually identify the defects. Specifically, conversion server 608 outputs a series of commands to a web marker 602, which then applies locating marks to the web 603. In many applications of the present invention, web marker 602 places the locating marks on or adjacent to the defects within web 603 in accordance with the respective conversion plan. However, in some specialized applications the locating marks are spaced in a predetermined way from the anomalies whose position they identify. Web marker 602 may include, for example, a series of ink jet modules, each having a series of jet nozzles.

The type of mark and the exact position of the mark on or near the defect may be selected based upon the web material, defect classification, web processing required to address the defect, and the intended end use application of the web. In the case of the arrayed ink marker, markers are fired preferentially depending on their cross-web position as defects pass the unit in the down-web direction. With this method, marking accuracies of less than 1 mm have been regularly achieved on high-speed webs with production rates greater than 150 ft/minute. However, higher speed webs in excess of 1000 meter/minute are within the capability of the invention.

Conversion server 608 may pause the conversion of web 603 at any point in accordance with the conversion plan to allow reconfiguration of conversion unit 604. For example, in the even web 603 is to be converted to different products, conversion server 608 halts the conversion process after the first product is produced to allow conversion unit 604 to be reconfigured for the subsequent product. Positioning of cutting devices and other mechanisms, for example, may be reconfigured as needed to produce the second product.

Figure 26:
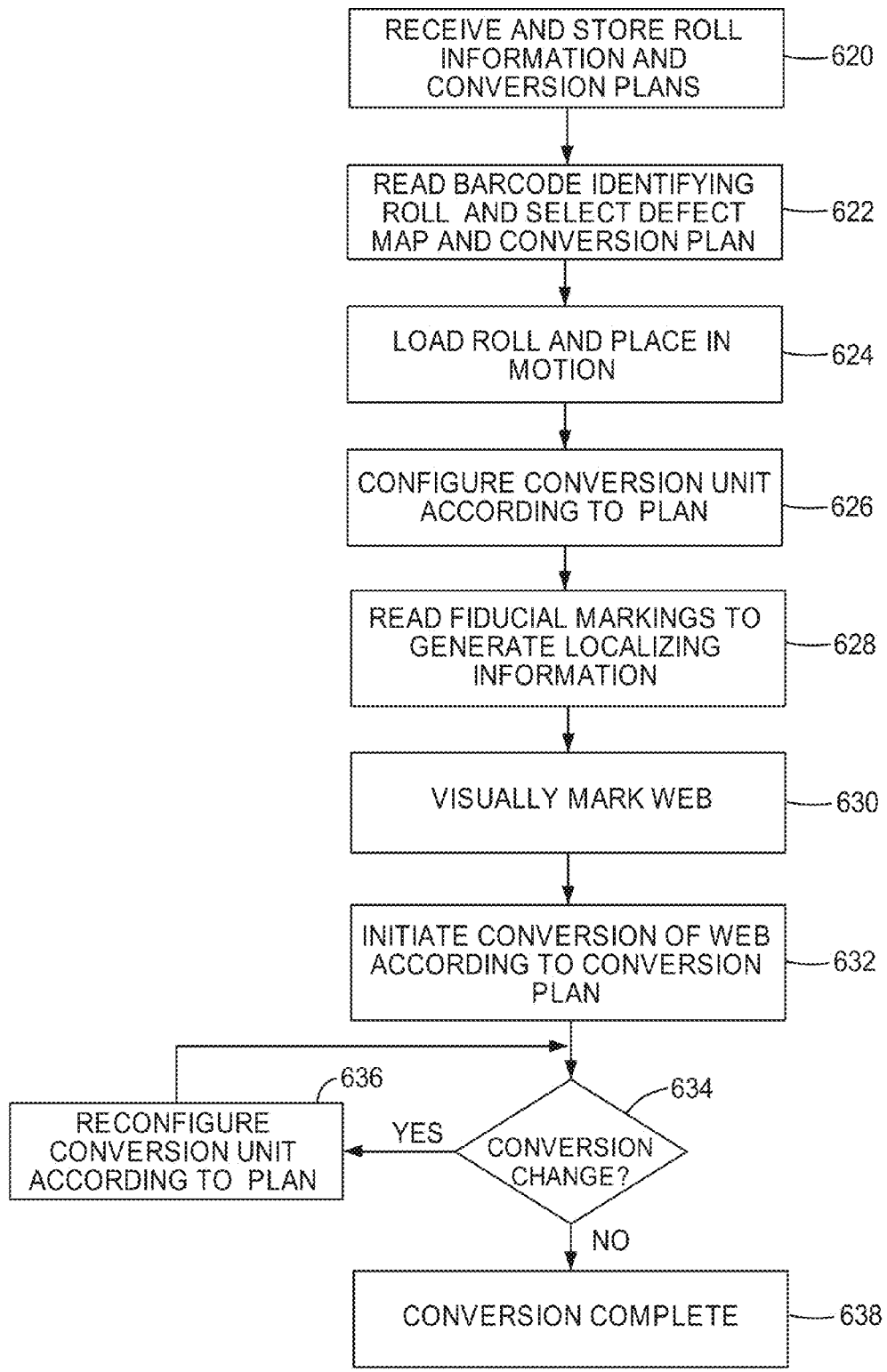
FIG. 26 is a flowchart illustrating exemplary operation of the converting site in processing a web in accordance with a conversion plan to achieve a maximum yield or other configurable parameter.

FIG. 26 is a flowchart illustrating exemplary operation of a converting site, such as converting site 8A, in processing a web in accordance with conversion plans to achieve, for example, a maximum yield or other configurable parameter.

Initially, conversion server 608 receives and stores roll information and conversion plans from conversion control system 4 (620). This may happen prior to or after receiving web rolls. For example, conversion server 608 may receive roll information and a conversion plan for a particular web roll weeks before the physical web roll arrives at the converting sites. Alternatively, conversion server 608 may receive roll information and a conversion plan for a web roll already stored within inventory at the converting site.

Next, conversion server 608 receives barcode information, for a particular web roll to be converted, causing conversion server 608 to access database 606 and retrieve the corresponding conversion map (622). As noted above, the barcode may be read prior to loading (e.g., by a hand-held barcode device) or via input device 600 after web 603 is loaded and readied for conversion.

Conversion server 608 displays a conversion plan, thereby allowing workers to configure conversion unit 604 to physically cut web 603 into numerous individual sheets (i.e., products 12A) in accordance with the conversion plan (526). Alternatively, conversion unit 604 may be configured in an automated or semi-automated manner in accordance with the conversion plan.

Once conversion unit 604 is configured, web 603 is set in motion and input device 500 reads fiducial marks and associated barcodes (528), and web marker 602 may be utilized to visually mark web 603 in order to assist in the visual recognition of defective products (630). Conversion unit 604 converts the received web 603 to form products 12A (632).

At any point within the conversion plan, conversion server 608 may determine that a reconfiguration is required by the plan (634). If so, conversion server 608 directs the reconfiguration of conversion unit 604 (636). This process continues until all of web 603 is converted to one or more products 12A in accordance with the conversion plan (638).

Figure 27:
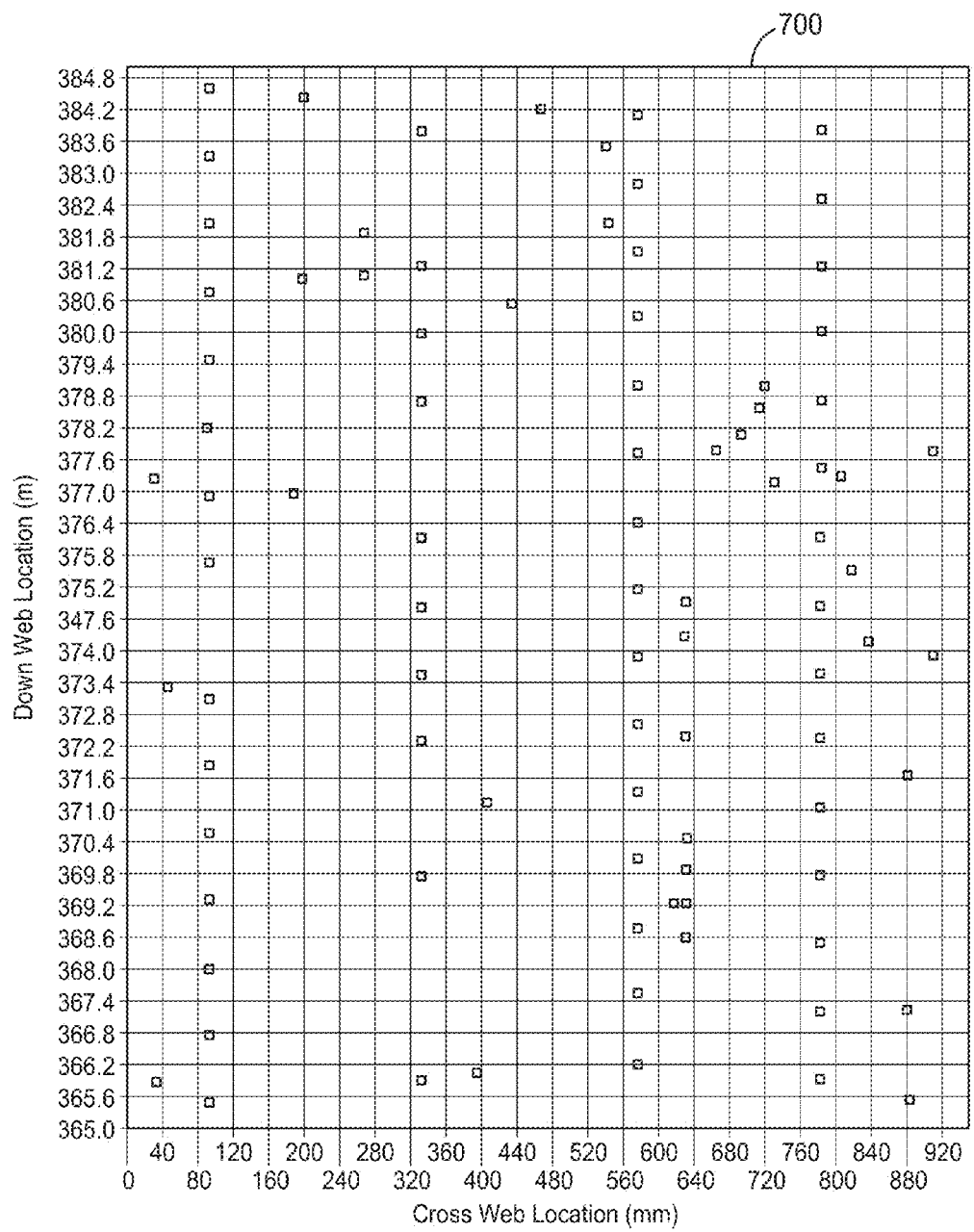
FIGS. 27-29 illustrate example defect maps.

FIG. 27 illustrates an example defect map 700 generated by application of a first recipe to actual anomaly data for a section of an exemplary web roll. In this example, the first recipe has been configured to consider all anomalies, i.e., both repeating anomalies and non-repeating anomalies. Moreover, the first recipe has been configured to apply a first level of sensitivity when classifying the anomalies as defects. As shown in FIG. 27, defect map includes occurrences of both random and repeated anomalies that have been determined to be defects based on the first level of severity.

Figure 28:
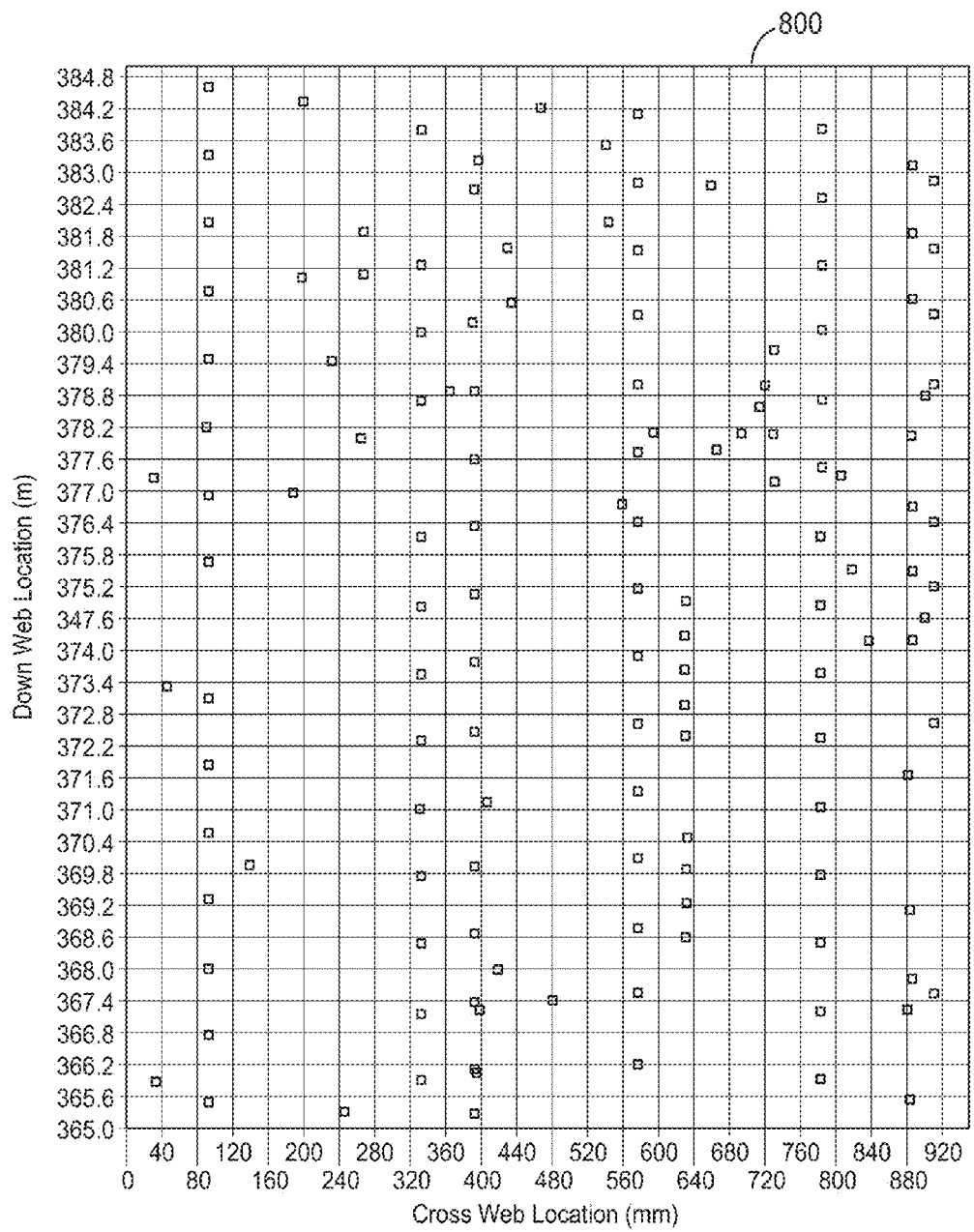

FIG. 28 illustrates a second example defect map 800 generated by application of a second recipe to the same anomaly data for the section of the example web roll. In this example, the second recipe has been configured to consider all anomalies, i.e., both repeating anomalies and non-repeating anomalies but has been configured to apply a second level of sensitivity that is higher than the level of sensitivity applied by the first recipe. As shown in FIG. 28, defect map 800 includes increased occurrences of both random and repeated anomalies that have been determined to be defects based on the second level of severity. As such, the second recipe may be used instead of the first recipe in certain situations to potentially achieve an increased level of customer satisfaction at the expense of considerable loss in web utilization.

Figure 29:
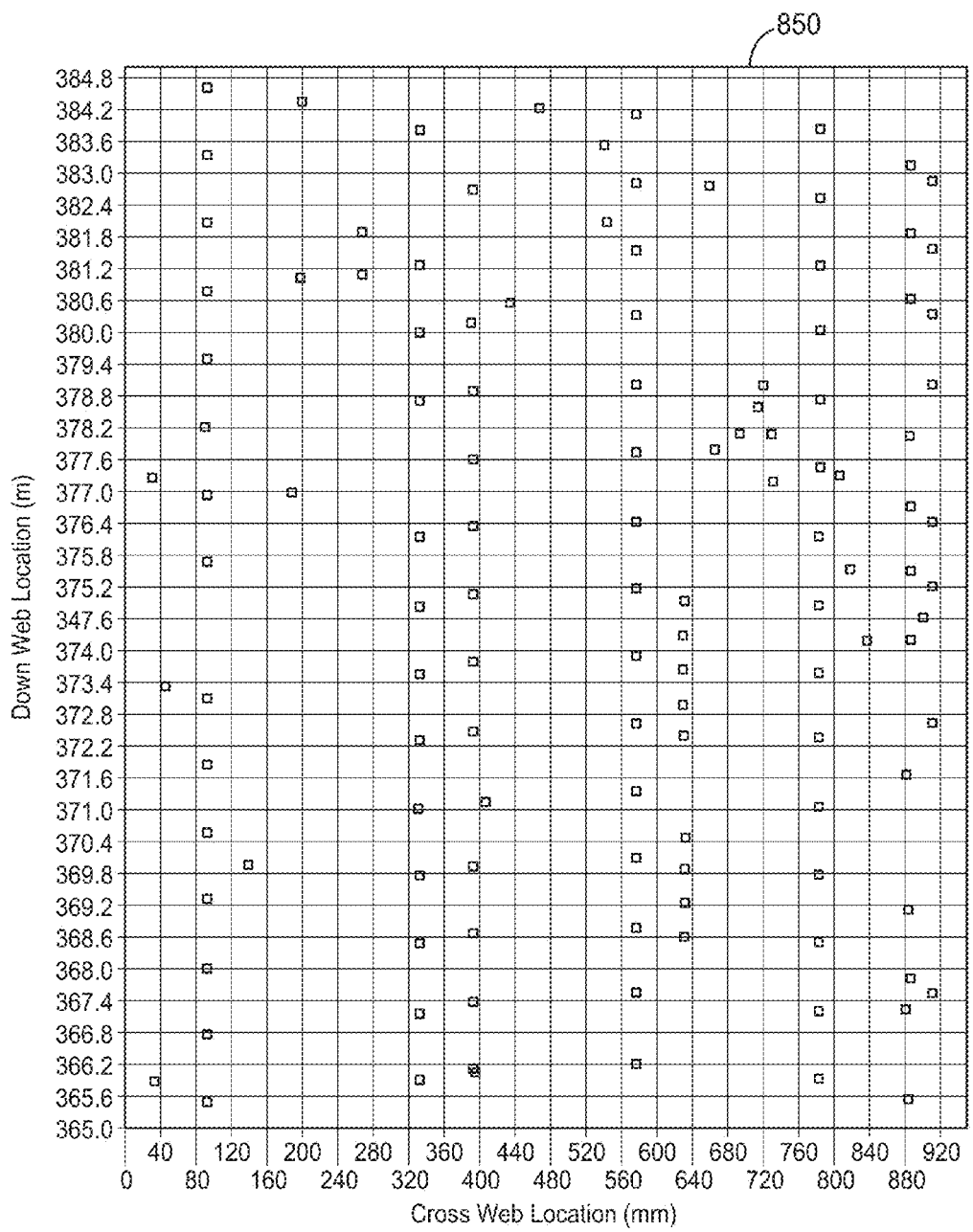

FIG. 29 illustrates a third defect map 850 generated by application of a third recipe configured to the same anomaly data for the section of the example web roll. In this example, third first recipe (i.e., the less sensitive recipe) has been configured to consider for defects only those anomalies that have been determined to be non-repeating, i.e., random. Further, the second recipe (i.e., the higher sensitive recipe) has been configured to consider for defects only those anomalies determined to be repeating anomalies. As can be seen in FIG. 29 in view of FIGS. 27, 28, defect map 850 includes an increased number of defects relative to uniform application of the less sensitive first recipe (defect map 700 of FIG. 27) but a reduced number of defects relative to uniform application of the higher sensitive recipe (defect map 800 of FIG. 28). As such, the third recipe (i.e., the modified combination) may be used instead of uniform application of the more sensitive second recipe in certain situations to potentially achieve an increased level of web utilization without substantially impacting customer satisfaction.

Table 1 below shows actual data upon application of the recipes to the entire length of the example web roll. In this case, the number of anomalies that qualify as defects with the third recipe, i.e., the modified combination of the first recipe as applied to random anomalies and the second recipe as applied to repeat anomalies, is much less than with uniform application of the second recipe. That is, in this experiment, the third recipe detects 765 more defects than the less sensitive first recipe, but 1501 less defects than the more sensitive second recipe. Thus, one can realize the benefit of the more sensitive second recipe with respect to repeating anomalies, which tend to have an increased impact on customer satisfaction, while accepting approximately only one-third of the additional defect burden over the less sensitive first recipe. In this case, that would amount to a 0.27% yield increase if the web were converted into display products for small handheld devices and a 6.02% yield increase if it were converted into display products for larger-sized notebooks.

TABLE 1

|  | Defects | Handheld Yield (56 mm × 42 mm) | Notebook Yield (356 mm × 200 mm) |
| --- | --- | --- | --- |
| First Recipe | 5015 | 98.80% | 72.10% |
| Second Recipe | 7281 | 98.43% | 62.54% |
| Third Recipe | 5780 | 98.70% | 68.56% |
| Absolute improvement | 1501 | 0.27% | 6.02% |
| % of Recipe Gap | 66.24% | 72.97% | 62.97% |

Figure 30:
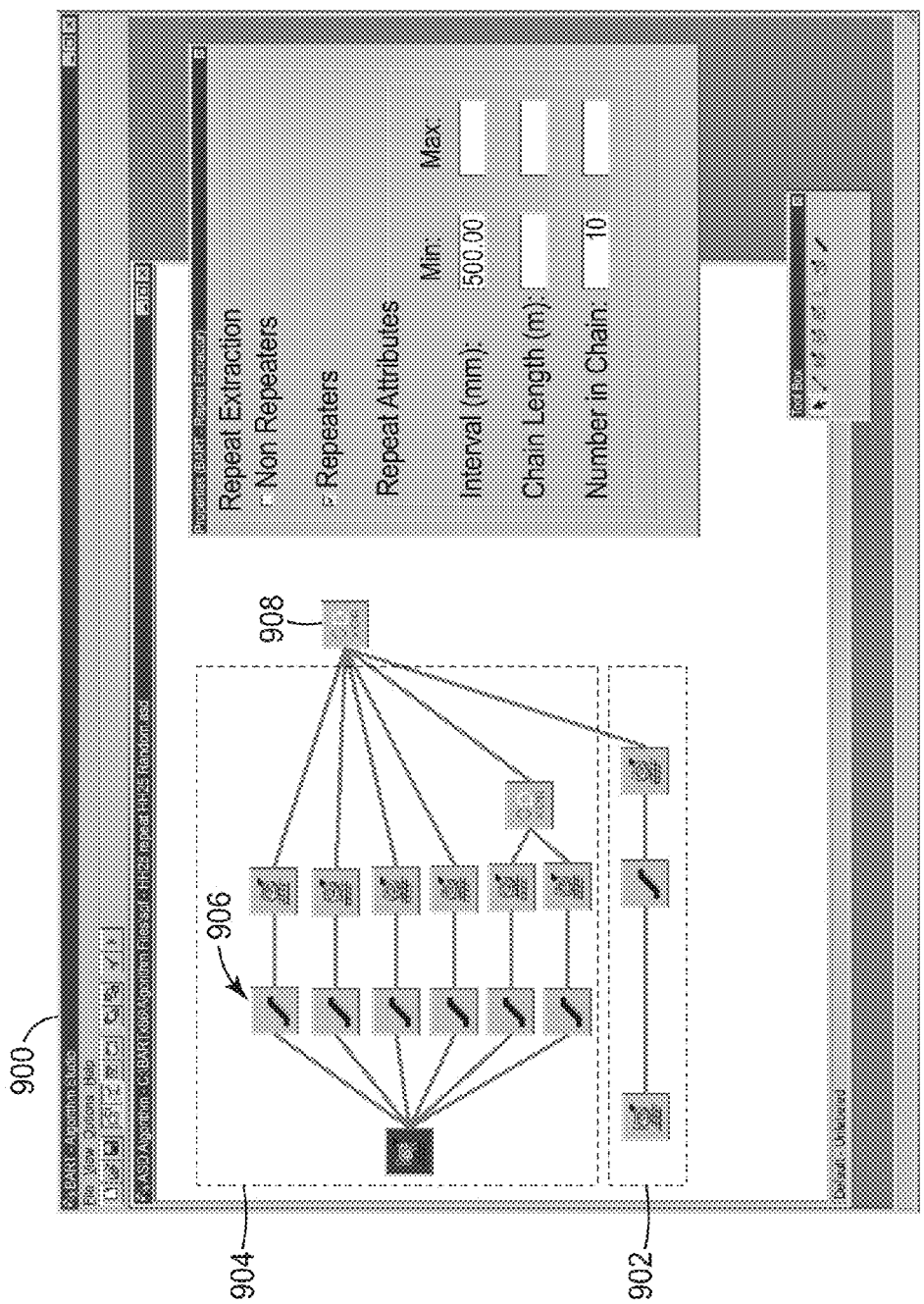
FIG. 30 illustrates an example user interface by which an operator configures application of different application-specific defect detection recipes for repeating and random anomalies, including combinations thereof.

FIG. 30 illustrates an example user interface 900 by which an operator defines first recipe 902 for application to random anomalies and a second recipe 904 for application to repeat anomalies, where the second recipe applies a plurality of different image processing operations 906 when analyzing image data for a given anomaly. In this manner, second recipe 904 may be more sensitive or "strict" with respect to classifying anomalies as defects, as discussed above. In this example, the user has configured second recipe 904 to only detect repeating defects having greater than a 500 mm repeat distance and a chain length of greater or equal to 10 instances. In addition the operator has defined in effect a third recipe that combines the results of recipes 902, 904 using a union operation 908.

Various embodiments of the invention have been described. These and other embodiments are within the scope of the following claims.

The invention claimed is:

1. A method comprising:
 imaging a sequential portion of a web to provide digital information;
 processing the digital information with at least one initial algorithm to identify regions on the web containing anomalies;
 identifying positions of the anomalies on the web;
 identifying, based on the positions of the anomalies on the web, a set of the anomalies as repeated anomalies and the remaining anomalies as random anomalies;
 analyzing, by at least one processor, the digital information for the repeated anomalies with a first defect detection algorithm to determine, based on a first set of characteristics, which of the repeated anomalies represent actual defects for a product;
 analyzing, by the at least one processor, the digital information for the random anomalies with a second, different defect detection algorithm to determine, based on a second set of characteristics, which of the random anomalies represent actual defects for the product, wherein at least one characteristic is included in both the first set of characteristics and the second set of characteristics, wherein the first defect detection algorithm is configured to apply a first threshold to the at least one characteristic to determine which of the repeated anomalies represent actual defects and the second detection algorithm is configured to apply a second threshold to the at least one characteristic to determine which of the random anomalies represent actual defects, and wherein the first threshold is lower than the second threshold; and
 converting the web into at least two sheets based on the determined actual defects for the product.

2. The method of claim 1, wherein the first defect detection algorithm is configured to apply the first threshold to the at least one characteristic to determine which of the repeated anomalies represent actual defects by applying an increased sensitivity to the at least one characteristic to determine which of the repeated anomalies represent actual defects, and wherein the second, different detection algorithm is configured to apply the second threshold to the at least one characteristic to determine which of the random anomalies represent actual defects by applying a decreased sensitivity to the at least one characteristic to determine which of the random anomalies represent actual defects.

3. The method of claim 1, further comprising:
 extracting a portion of the digital information for each of the identified regions,
 wherein analyzing, by the at least one processor, the digital information for the repeated anomalies with the first defect detection algorithm to determine, based on the first set of characteristics, which of the repeated anomalies represent actual defects for the product and analyzing, by the at least one processor, the digital information for the random anomalies with the second, different defect detection algorithm to determine, based on the second set of characteristics, which of the random anomalies represent actual defects for the product comprises analyzing the extracted portions of the digital information with the first defect detection algorithm and the second, different defect detection algorithm to determine the actual defects in the web.

4. The method of claim 3, further comprising storing or buffering the extracted portions of the digital information prior to analyzing.

5. The method of claim 4, wherein the stored or buffered portions are analyzed after the imaging has been performed on the entire web.

6. The method of claim 1, wherein processing the digital information with the at least one initial algorithm comprises thresholding the digital information and forming a blob list.

7. The method of claim 1, wherein the first defect detection algorithm and the second, different defect detection algorithm each include one or more of neighborhood averaging, neighborhood ranking, contrast expansion, various monadic and dyadic image manipulations, digital filtering, texture analysis, fractal analysis, frequency processing, convolutions, morphological processing, thresholding, connected component analyses, blob processing or blob classifications.

8. The method of claim 1, wherein the first defect detection algorithm and the second, different defect detection algorithm each includes a plurality of image processing steps, wherein the plurality of image processing steps for each algorithm include at least comparing each anomaly against a combination threshold-pixel size criterion.

9. The method of claim 8, wherein the combination threshold-pixel size criterion for the first defect detection algorithm defines a pixel size that is smaller than a pixel size defined by the combination threshold-pixel size criterion for the second, different defect detection algorithm.

10. The method of claim 8, wherein the combination threshold-pixel size criterion for the first defect detection algorithm defines a pixel size that is larger than a pixel size defined by the combination threshold-pixel size criterion for the second, different defect detection algorithm.

11. The method of claim 8, wherein an anomaly is identified as an actual defect if any one of the combination threshold-pixel size criteria is satisfied.

12. The method of claim 1, further comprising:
 receiving roll synchronization signals from a plurality of sensors of a web manufacturing system, wherein each of the sensors corresponds to a different roller of the web manufacturing system, and wherein each of the roll synchronization signals indicates that the corresponding roller has completed a full rotation during manufacturing of the web.

13. The method of claim 1, wherein the first threshold and the second threshold are determined based on a recipe for the product.

14. A system comprising:
 an encoder on at least one roller that outputs a position signal indicative of a down-web distance of a web;
 an imaging device that images a sequential portion of the web to provide digital information;
 an analysis computer that processes the digital information with at least one initial algorithm to identify regions on the web containing anomalies, wherein the analysis computer processes the anomaly data to determine the positions of the anomalies on the web based on the position signal and identifies a set of the anomalies as repeated anomalies and the remaining anomalies as random anomalies; and a conversion control system that:
analyzes the digital information for the repeated anomalies with a first defect detection algorithm to determine, based on a first set of characteristics, which of the repeated anomalies represent actual defects for a product and analyzes the digital information for the random anomalies with a second, different defect detection algorithm to determine, based on a second set of characteristics, which of the random anomalies represent actual defects for the product, wherein at least one characteristic is included in both the first set of characteristics and the second set of characteristics, wherein the first defect detection algorithm is configured to apply a first threshold to the at least one characteristic to determine which of the repeated anomalies represent actual defects and the second detection algorithm is configured to apply a second threshold to the at least one characteristic to determine which of the random anomalies represent actual defects, and wherein the first threshold is lower than the second threshold, and converts the web into the product based on the determined actual defects for the product.

15. The system of claim 14, wherein the roller comprises a plurality of rollers in contact with the web during manufacturing, wherein two or more rollers of the plurality of rollers each include a synchronization mark to indicate when the corresponding roller has completed a full rotation, further comprising:

a plurality of synchronization mark readers that read the synchronization marks of the plurality of rollers and output roll synchronization signals, wherein each of the roll synchronization signals indicates that the corresponding roller has completed a full rotation during manufacturing of the web; and a synchronization unit that receives the position signal from the encoder and the plurality of roll synchronization signals from the plurality of synchronization mark readers, wherein the synchronization unit converts the occurrence of each of the roll synchronization signals into down-web positions within a coordinate system associated with a web process line, wherein the analysis computer outputs an indication of which of the rollers caused the repeated anomalies by correlating the positions of the repeated anomalies with the down-web positions of the roll synchronization signals.

16. The system of claim 14, wherein the first defect detection algorithm is configured to apply the first threshold to the at least one characteristic to determine which of the repeated anomalies represent actual defects by applying an increased sensitivity to the at least one characteristic to determine which of the repeated anomalies represent actual defects, and the second, different defect detection algorithm is configured to apply the second threshold to the at least one characteristic to determine which of the random anomalies represent actual defects by applying a decreased sensitivity to the at least one characteristic to determine which of the random anomalies represent actual defects.

17. The system of claim 14, wherein the analysis computer extracts a portion of the digital information for each of the identified regions, and the conversion control system analyzes the extracted portions of the digital information with the first defect detection algorithm and the second, different defect detection algorithm to determine the actual defects in the web.

18. The system of claim 14, wherein the analysis computer further stores or buffers the extracted portions of the digital information prior to analyzing the extracted portions of the digital information.

19. The system of claim 18, wherein the analysis computer analyzes the stored or buffered portions after the imaging device has imaged the entire web.

20. The system of claim 14, wherein the analysis computer processes the digital information with the initial algorithm by at least thresholding the digital information and forming a blob list.

21. The system of claim 14, wherein the first defect detection algorithm and the second, different defect detection algorithm each include one or more of neighborhood averaging, neighborhood ranking, contrast expansion, various monadic and dyadic image manipulations, digital filtering, texture analysis, fractal analysis, frequency processing, convolutions, morphological processing, thresholding, connected component analyses, blob processing or blob classifications.

22. The system of claim 14, wherein the first defect detection algorithm and the second, different defect detection algorithm each includes a plurality of image processing steps, wherein the plurality of steps for each algorithm include at least comparing each anomaly against a combination threshold-pixel size criterion.

23. The system of claim 22, wherein the combination threshold-pixel size criterion for the first defect detection algorithm defines a pixel size that is smaller than a pixel size defined by the combination threshold-pixel size criterion for the second, different defect detection algorithm.

24. The system of claim 22, wherein the combination threshold-pixel size criterion for the first defect detection algorithm defines a pixel size that is larger than a pixel size defined by the combination threshold-pixel size criterion for the second, different defect detection algorithm.

25. The system of claim 22, wherein an anomaly is identified as an actual defect if any one of the combination threshold-pixel size criteria is satisfied.

26. The system of claim 14, wherein the first threshold and the second threshold are determined based on a recipe for the product.

27. A computer-readable storage medium comprising instructions for causing a programmable processor to:

receive digital data from a web inspection system that identifies positions of anomalies on the web;

process the digital information with at least one initial algorithm to identify regions on the web containing the anomalies;

based on the positions of the anomalies on the web, identify a set of the anomalies as repeated anomalies and the remaining anomalies as random anomalies;

analyze the digital information for the repeated anomalies with a first defect detection algorithm to determine, based on a first set of characteristics, which of the repeated anomalies represent actual defects for a product;

analyze the digital information for the random anomalies with a second, different defect detection algorithm to determine, based on a second set of characteristics, which of the random anomalies represent actual defects for the product, wherein at least one characteristic is included in both the first set of characteristics and the second set of characteristics, wherein the first defect detection algorithm is configured to apply a first threshold to the at least one characteristic to determine which of the repeated anomalies represent actual defects and the second detection algorithm is configured to apply a second threshold to the at least one characteristic to determine which of the random anomalies represent actual defects, wherein the first threshold is lower than the second threshold; and output a defect map to control conversion of the web to products, where the defect map specifies the positions of the actual defects.

28. The computer-readable storage medium of claim 27, wherein the first threshold and the second threshold are determined based on a recipe for the product.

* * * * *